(12) United States Patent
Virca et al.

(10) Patent No.: US 10,363,252 B2
(45) Date of Patent: *Jul. 30, 2019

(54) TREATMENT OF PROSTATE CANCER USING HEDGEHOG PATHWAY INHIBITORS

(71) Applicant: HEDGEPATH PHARMACEUTICALS, INC., Tampa, FL (US)

(72) Inventors: Nicholas J. Virca, Tampa, FL (US); Francis E. O'Donnell, Jr., Longboat Key, FL (US)

(73) Assignee: HEDGEPATH PHARMACEUTICALS, INC., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/966,844

(22) Filed: Apr. 30, 2018

(65) Prior Publication Data

US 2018/0243296 A1 Aug. 30, 2018

Related U.S. Application Data

(63) Continuation of application No. 15/420,283, filed on Jan. 31, 2017, now Pat. No. 9,968,600, which is a
(Continued)

(51) Int. Cl.
*A61K 31/496* (2006.01)
*A61K 31/00* (2006.01)
(Continued)

(52) U.S. Cl.
CPC .......... *A61K 31/496* (2013.01); *A61K 9/0053* (2013.01); *A61K 9/4866* (2013.01);
(Continued)

(58) Field of Classification Search
CPC .... A61K 31/365; A61K 31/415; A61K 31/44; A61K 31/496; A61K 31/497
See application file for complete search history.

(56) References Cited

U.S. PATENT DOCUMENTS 6,238,876 B1 5/2001 Altaba
6,881,745 B2 4/2005 Hayes et al.
(Continued)

FOREIGN PATENT DOCUMENTS

CN 102319260 1/2012
JP 2008-502585 1/2008
(Continued)

OTHER PUBLICATIONS

Aftab BT et al., "Itraconazole Inhibits Angiogenesis and Tumor Growth in Non-Small Cell Lung Cancer" *Cancer Research*, 2011, 71(21):6764-6772.
(Continued)

*Primary Examiner* — Savitha M Rao
(74) *Attorney, Agent, or Firm* — Saliwanchik, Lloyd & Eisenschenk

(57) ABSTRACT

The present invention concerns methods for treating a proliferation disorder, such as prostate cancer, basal cell carcinoma, lung cancer, and other cancers, using an inhibitor of the Hedgehog pathway (HhP); and methods for monitoring subjects undergoing such treatments based on biomarkers and other criteria predictive of efficacy.

20 Claims, 3 Drawing Sheets

Related U.S. Application Data continuation of application No. 14/947,345, filed on Nov. 20, 2015, now abandoned, which is a continuation of application No. 14/173,588, filed on Feb. 5, 2014, now Pat. No. 9,192,609.

(60) Provisional application No. 61/831,823, filed on Jun. 6, 2013, provisional application No. 61/813,122, filed on Apr. 17, 2013.

(51) Int. Cl.
| | |
|---|---|
| A61K 31/497 | (2006.01) |
| A61K 31/415 | (2006.01) |
| A61K 45/06 | (2006.01) |
| A61K 31/519 | (2006.01) |
| A61K 31/58 | (2006.01) |
| A61K 33/24 | (2019.01) |
| A61K 9/00 | (2006.01) |
| G01N 33/574 | (2006.01) |
| A61K 9/48 | (2006.01) |

(52) U.S. Cl.
CPC ............ *A61K 31/519* (2013.01); *A61K 31/58* (2013.01); *A61K 33/24* (2013.01); *A61K 45/06* (2013.01); *G01N 33/57484* (2013.01); *G01N 2333/96455* (2013.01)

(56) References Cited

U.S. PATENT DOCUMENTS

| | | | |
|---|---|---|---|
| 7,230,004 | B2 | 6/2007 | Adams et al. |
| 8,653,083 | B2 | 2/2014 | Beachy et al. |
| 8,771,739 | B2 | 7/2014 | Hayes et al. |
| 8,921,374 | B2 | 12/2014 | Mudge et al. |
| 8,980,930 | B2 | 3/2015 | Liu et al. |
| 9,095,589 | B2 | 8/2015 | Liu et al. |
| 9,272,046 | B2 | 3/2016 | Mudge et al. |
| 9,346,791 | B2 | 5/2016 | Liu et al. |
| 9,650,365 | B2 | 5/2017 | Hadden et al. |
| 9,839,636 | B2 | 12/2017 | Hadden et al. |
| 2002/0006931 | A1 | 1/2002 | Beachy et al. |
| 2003/0022819 | A1 | 1/2003 | Ling et al. |
| 2003/0225104 | A1 | 12/2003 | Hayes et al. |
| 2007/0021493 | A1 | 1/2007 | Guicherit et al. |
| 2007/0060546 | A1 | 3/2007 | Ruat et al. |
| 2007/0231828 | A1 | 10/2007 | Beachy et al. |
| 2008/0019961 | A1 | 1/2008 | Wicha et al. |
| 2008/0260835 | A1 | 10/2008 | Hayes et al. |
| 2008/0287420 | A1 | 11/2008 | Castro et al. |
| 2008/0293754 | A1 | 11/2008 | Austad et al. |
| 2008/0293755 | A1 | 11/2008 | Castro et al. |
| 2009/0203713 | A1 | 8/2009 | Beachy et al. |
| 2010/0080855 | A1 | 4/2010 | Beachy et al. |
| 2010/0093625 | A1 | 4/2010 | Tarasova et al. |
| 2010/0286114 | A1 | 11/2010 | Thomas et al. |
| 2011/0183948 | A1 | 7/2011 | Levine et al. |
| 2012/0083419 | A1 | 4/2012 | Altaba et al. |
| 2013/0109700 | A1 | 5/2013 | Epstein, Jr. et al. |
| 2014/0336111 | A1 | 11/2014 | Gebhardt |
| 2016/0130258 | A1 | 5/2016 | Lairson et al. |
| 2017/0119740 | A1 | 5/2017 | Beachy et al. |

FOREIGN PATENT DOCUMENTS

| | | |
|---|---|---|
| JP | 2009-506054 | 2/2009 |
| JP | 2011-516426 | 5/2011 |
| JP | 2011-520921 | 7/2011 |
| WO | WO 2001/19800 | 3/2001 |
| WO | WO 2001/26644 | 4/2001 |
| WO | WO 2001/27135 | 4/2001 |
| WO | WO 01/47492 | 7/2001 |
| WO | WO 2001/49279 | 7/2001 |
| WO | WO 2001/74344 | 10/2001 |
| WO | WO 2003/011219 | 2/2003 |
| WO | WO 2003/088970 | 10/2003 |
| WO | WO 2004/020599 | 3/2004 |
| WO | WO 2005/042700 | 5/2004 |
| WO | WO 2005/013800 | 2/2005 |
| WO | WO 2005/032343 | 4/2005 |
| WO | WO 2005/033288 | 4/2005 |
| WO | WO 2005/041865 | 5/2005 |
| WO | WO 2006/028958 | 3/2006 |
| WO | WO 2006/050351 | 5/2006 |
| WO | WO 2006/078283 | 7/2006 |
| WO | WO 2007/024971 | 3/2007 |
| WO | WO 2007/054623 | 5/2007 |
| WO | WO 2007/059157 | 5/2007 |
| WO | WO 2007/120827 | 10/2007 |
| WO | WO 2007/131201 | 11/2007 |
| WO | WO 2008/070357 | 6/2008 |
| WO | WO 2008/110611 | 9/2008 |
| WO | WO 2008/112913 | 9/2008 |
| WO | WO 2008/124132 | 10/2008 |
| WO | WO 2008/131354 | 10/2008 |
| WO | WO 2009/121042 | 10/2009 |
| WO | WO 2009/140675 | 11/2009 |
| WO | WO 2011/088404 | 7/2011 |
| WO | WO 2013/036866 | 3/2013 |
| WO | WO 2013/192566 | 12/2013 |

OTHER PUBLICATIONS

"11 percent of men in America with Metastatic prostate cancer get no anti-cancer therapy" *The "New" Prostate Cancer InfoLink*, posted Aug. 7, 2012, by Sitemaster; http://prostatecancerinfolink.net/2012/08/07/11-percent-of-men-in-america-with-metastatic-prostate-cancer-get-no-anti-cancer-therapy/.

"A Guide for Employers: Using Comparative Effectiveness Research: Treatments for Clinically Localized Prostate Cancer" *National Business Group on Health*, Jun. 2011, 1-7.

"About Squamous Cell Carcinoma" *Memorial Sloan Kettering Cancer Center*, Printed Mar. 18, 2014; http://www.mskcc.org/cancer-care/adult/squamous-cell-carcinoma/about-squamous-cell-carcinoma.

"Another step in the projected marketing battle: abiraterone vs. MDV3100" posted on Mar. 23, 2012 by "Sitemaster"; *The "New" Prostate Cancer Infolink*, http://prostatecancerinfolink.net/2012/03/23/another-step-in-the-projected-marketing-battle-abiraterone-vs-mdv3100/.

"Curis Operable BCC Human Data: Early Results and Further Commentary" *Seeking Alpha*, Posted Apr. 15, 2012; http://seekingalpha.com/article/497881-curis-operable-bcc-human-data-early-results-and-further-commentary.

"Exploring new pathways to cancer therapy" HedgePath Pharmaceuticals, Inc., Biotech Showcase Presentation, presented Jan. 14, 2014 at the Bio Conference in San Francisco, CA.

"Genentech Submits New Drug Application to FDA for Vismodegib for Rare Form of Advanced Skin Cancer" *Genentech*, posted Sep. 12, 2011; http://www.gene.com/media/press-releases/13587/2011-09-12/genentech-submits-new-drug-application-t.

"Hopkins Prostate Cancer Experts Available" http://www.hopkinsmedicine.org/news/media/releases/hopkins_prostate_cancer_experts_available, Sep. 14, 2010.

"Issues Concerning the Development of Products for the Treatment of Patients with Non-Metastic Castration-Resistant Prostate Cancer" *FDA ODAC Briefing Document*, Sep. 14, 2011, 1-9.

"Lung Cancer: CCO Independent Conference Coverage of the 2013 American Society of Clinical Oncology Meeting" *Clinical Care Options Oncology*, May 31-Jun. 4, 2013, Chicago, Illinois. [uploaded in 4 parts].

"Medivation and Astellas Announce Submission of New Drug Application for Enzalutamide for the Treatment of Castration-Resistant Prostate Cancer in Patients Previously Treated With Chemotherapy" *Medivation*, posted May 21, 2012; http://investors.medivation.com/releasedetail.cfm?releaseid=675497.

"Second Study confirms data on PSADT and survival post-surgery" The "New" Prostate Cancer InfoLink, posted Dec. 29, 2010 by

(56) References Cited

OTHER PUBLICATIONS

Sitemaster; http://prostatecancerinfolink.net/2010/12/29/second-study-confirms-data-on-psadt-and-survival-post-surgery/.
"Snapshot: Prostate Cancer—Global Drug Forecasts and Treatment Analysis" Pharmaceutical-technology.com, posted Aug. 1, 2011; http://www.pharmaceutical-technology.com/features/feature125729/.
"What is Gorlin Syndrome" Genetics Home Reference, reviewed Oct. 2012; http://ghr.nlm.nih.gov/condition/gorlin-syndrome.
"Zytiga, Xtandi to dominate prostate cancer market" BioSpectrum, posted Dec. 12, 2012; http://www.biospectrumasia.com/biospectrum/news/123103/ zytiga-xtandi-dominate-prostrate-cancer-market#. Uyij_vmtFmM.
Abrahamsson PA, "Options for Increasing Prostate-specific Antigent After Radical Prostatectomy" Prostate Cancer, 2007, 19-20.
Antonarakis E et al., "Survival in men with nonmetastatic prostate cancer treated with hormone therapy: a quantitative systematic review" Journal of Clinical Oncology, 2007, 25(31):4998-5008.
Antonarakis ES and Armstrong AJ, "Changing Paradigms in the Management of Metastatic Castration-Resistant Prostate Cancer" Pharmacy Practice News, Clinical, Educational Review, Nov. 2011, pp. 30-45.
Antonarakis ES and Armstrong AJ, "Emerging therapeutic approaches in the management of metastic castration-resistant prostate cancer" Prostate Cancer and Prostatic Diseases, 2011, 14:206-218.
Antonarakis ES et al., "Repurposing Itraconazole as a Treatment for Advanced Prostate Cancer: A Noncomparative Randomized Phase II Trial in Men With Metastic Castration-Resistant Prostate Cancer" The Oncologist, 2013, 18:163-173.
Armstrong AJ and Beer TM, "Treatment of Castration-Resistant Prostate Cancer: Current Options and Novel Therapies" Cancernetwork / Oncology, posted Apr. 26, 2012; http://www.cancernetwork.com/prostate-cancer/treatment-castration-resistant-prostate-cancer-current-options-and-novel-therapies.
Aszterbaum M et al., "Identification of Mutations in the Human Patched Gene in Sporadic Basal Cell Carcinomas and in Patients with the Basal Cell Nevus Syndrome" The Society for Investigative Dermatology, Inc., 1998, 110(6):885-888.
Atwood SX et al., "Hedgehog pathway inhibition and the race against tumor evolution" Journal of Cell Biology, 2012, 199(2):193-197.
Auclerc G et al., "Management of Advanced Prostate Cancer" The Oncologist, 2000, 5:36-44.
Azvolinsky A, "Novel Drug, MDV3100, Will Likely Have a Major Role in Prostate Cancer Treatment" Oncology, Feb. 15, 2012; http://www.cancernetwork.com/prostate-cancer/novel-drug-mdv3100-will-likely-have-major-role-prostate-cancer-treatment.
Bae SK et al., "Increased Oral Bioavailability of Itraconazole and Its Active Metabolite, 7-Hydroxyitraconazole, When Coadministered With a Vitamin C Beverage in Healthy Participants" Journal of Clinical Pharmacology, 2011, 51:444-451.
Bankhead C "Antifungal May Help in Prostate Cancer", Published Apr. 6, 2012, www.medpagetoday.com/MeetingCoverage/AACR/32064.
Baxter JM, "Facial basal Cell Carcinoma" BMJ, 2012, 345:e5342.
Beach DF and Somer R, "Novel Approach to Gorlin Syndrome: A Patient Treated With Oral Capecitabine" Journal of Clinical Oncology: Diagnosis in Oncology, 2011, 29(14):e397-e401.
Beasley D, "FDA approves Medivation prostate cancer drug" Reuters, posted Aug. 31, 2012; http://www.reuters.com/article/2012/08/31/us-medivation-astellas-idUSBRE87U0Y520120831.
Beasley D, "Peregrine drug doubles lunch cancer survival in trial" Reuters, posted Sep. 7, 2012; http://www.reuters.com/article/2012/09/07/us-peregrine-lungcancer-idUSBRE8860Y620120907.
Beltran H et al., "New Therapies for Castration-Resistant Prostate Cancer: Efficacy and Safety" European Association of Urology, 2011, 60:279-290.
Boschert S, "GDC-0449 and Itraconazole Look Promising for Basal Cell" Internal Medicine News: digital network, Sep. 10, 2010.
Boschert S, "Two Promising Drugs Identified for Basal Cell Carcinomas" Internal Medicine News: digital network, Sep. 10, 2010.
Breneiser J, "The Road to GDC" The Quarterly Advocate, BCCNS Life Support Network, Newsletter, Jun. 2010, pp. 1-12.
Castro-Puyana M et al., "Separation and quantitation of the four stereoismers of itraconazole in pharmaceutical formulations by electrokinetic chromatography" Electrophoresis, 2006, 27(4):887-895.
Chang Als and Oro AE, "Initial Assessment of Tumor Regrowth After Vismodegib in Advanced Basal Cell Carcinoma" Research Letters, Nov. 2012 Online First, 148(11):1-2.
Chen M et al., "Hedgehog/Gli supports androgen signaling in androgen deprived and androgen independent prostate cancer cells" Molecular Cancer, 2010, 9:89.
Chong CR et al., "Inhibition of Angiogenesis by the Antifungal Drug Itraconazole" ACS Chemical Biology, 2007, 2(4):263-270.
Chrvala CA, "The Changing Landscape of Treatment Options for Metastatic Castrate-Resistant Prostate Cancer" P&T, 2012, 37(8):453-463.
Cirrone F and Harris CS, "Vismodegib and the Hedgehog Pathway: A New Treatment for Basal Cell Carcinoma" Clinical Therapeutics, 34(10), 2012:2039-2050.
ClinicalTrials.gov, "A Dose Finding and Safety Study of Oral LEQ506 in Patients With Advanced Solid Tumors" National Institute of Health Clinical Trial Identifier No. NCT01106508; Last updated: May 10, 2013.
ClinicalTrials.gov, "A Drug Interaction Study of GDC-0032 Co-administered With Rifampin or Itraconazole in Healthy Volunteers" National Institute of Health Clinical Trial Identifier No. NCT01814709; Last updated: Mar. 4, 2014.
ClinicalTrials.gov, "A Drug-Drug Interaction Study of the Effect of Rabeprazole, Itraconazole or Fluconazole on the Pharmacokinetics of Vismodegib" National Institute of Health Clinical Trial Identifier No. NCT01772290; Last updated: Mar. 4, 2014.
ClinicalTrials.gov, "A Phase 1 Study of BMS-833923 (XL139) in Subjects With Advanced or Metastatic Cancer" National Institute of Health Clinical Trial Identifier No. NCT00670189; Last updated: Aug. 22, 2013.
ClinicalTrials.gov, "A Phase 1 Study of BMS-833923 (XL139) in Subjects With Advanced or Metastatic Cancer" National Institute of Health Clinical Trial Identifier No. NCT00998166; Last updated: Sep. 10, 2013.
ClinicalTrials.gov, "A Phase II Study of Efficacy and Safety in Patients With Locally Advanced or Metastatic Basal Cell Carcinoma (BOLT)" National Institute of Health Clinical Trial Identifier No. NCT01327053; Last updated: Jun. 3, 2013.
ClinicalTrials.gov, "A Phase II Study of Itraconazole in Biochemical Relapse" National Institute of Health Clinical Trial Identifier No. NCT01787331; Last updated: Dec. 19, 2013.
ClinicalTrials.gov, "A Pilot Trial of Itraconazole Pharmacokinetics in Patients With Metastatic Breast Cancer" National Institute of Health Clinical Trial Identifier No. NCT00798135; Last updated: Aug. 7, 2013.
ClinicalTrials.gov, "A Randomized Phase II Study of Itraconazole and Pemetrexed in Patients With Previously Treated Non-Squamous Non-Small Cell Lung Cancer" National Institute of Health Clinical Trial Identifier No. NCT00769600; Last updated: Mar. 18, 2013.
ClinicalTrials.gov, "A Randomized Phase II Study of SUBATM-itraconazole in Patients With Untreated Squamous NSCLC." National Institute of Health Clinical Trial Identifier No. NCT01752023; Last updated: Oct. 10, 2013.
ClinicalTrials.gov, "A Study Evaluating the Efficacy and Safety of Vismodegib (GDC-0449, Hedgehog Pathway Inhibitor) in Patients With Advanced Basal Cell Carcinoma" National Institute of Health Clinical Trial Identifier No. NCT00833417; Last updated: Mar. 1, 2013.
ClinicalTrials.gov, "A Study Evaluating the Efficacy and Safety of Vismodegib (GDC-0449) in Operable Basal Cell Carcinoma (BCC)" National Institute of Health Clinical Trial Identifier No. NCT01201915; Last updated: Feb. 24, 2014.
ClinicalTrials.gov, "A Study of GDC-0449 (Hedgehog Pathway Inhibitor) in Patients Treated With GDC-0449 in a Previous Genentech-

(56) References Cited

OTHER PUBLICATIONS

Sponsored Phase I or II Cancer Study" National Institute of Health Clinical Trial Identifier No. NCT00959647; Last updated: Mar. 4, 2014.

ClinicalTrials.gov, "A Study of Hedgehog Pathway Inhibitor GDC-0449 in Patients With Locally Advanced or Metastatic Solid Tumors That Are Refractory to Standard Therapy or for Whom No Standard Therapy Exists" National Institute of Health Clinical Trial Identifier No. NCT00968981; Last updated: Aug. 11, 2011.

ClinicalTrials.gov, "A Study of PF-04449913 in Select Hematologic Malignancies" National Institute of Health Clinical Trial Identifier No. NCT00953758; Last updated: Dec. 8, 2013.

ClinicalTrials.gov, "A Study of Vismodegib (GDC-0449) in Patients With Locally Advanced or Metastatic Basal Cell Carcinoma" National Institute of Health Clinical Trial Identifier No. NCT01160250; Last updated: Jan. 7, 2013.

ClinicalTrials.gov, "Dose Finding and Safety of Oral LDE225 in Patients With Advanced Solid Tumors" National Institute of Health Clinical Trial Identifier No. NCT00880308; Last updated: Mar. 7, 2013.

ClinicalTrials.gov, "Efficacy, Safety and Pharmacokinetics of Oral LDE225 in Treatment of Patients With Nevoid Basal Cell Carcinoma Syndrome (NBCCS BCC)" National Institute of Health Clinical Trial Identifier No. NCT01350115; Last updated: Jun. 26, 2013.

ClinicalTrials.gov, "IPI-926 Extension Protocol for Continuation of Treatment With IPI-926" National Institute of Health Clinical Trial Identifier No. NCT01609179; Last updated: Nov. 13, 2012.

ClinicalTrials.gov, "Pilot Biomarker Trial to Evaluate the Efficacy of Itraconazole in Patients w/ Basal Cell Carcinomas" National Institute of Health Clinical Trial Identifier No. NCT01108094; Last updated: Jul. 11, 2012.

ClinicalTrials.gov, "STEVIE: A Study of Vismodegib in Patients With Locally Advanced or Metastatic Basal Cell Carcinoma" National Institute of Health Clinical Trial Identifier No. NCT01367665; Last updated: Mar. 3, 2014.

ClinicalTrials.gov, "Study Evaluating the Efficacy of Oral Vismodegib in Various Histologic Subtypes" National Institute of Health Clinical Trial Identifier No. NCT01700049; Last updated: Feb. 19, 2014.

ClinicalTrials.gov, "Study of Itraconazole in Castration Resistant Prostate Cancer (CRPC) Post Docetaxel Chemotherapy" National Institute of Health Clinical Trial Identifier No. NCT01450683; Last updated: Jul. 17, 2012.

ClinicalTrials.gov, "The Purpose of This Study is to Determine the Efficacy and Safety of a Systemic Hedgehog Pathway Antagonist (GDC-0449) in Patients With Basal Cell Nevus Syndrome (BCNS)" National Institute of Health Clinical Trial Identifier No. NCT00957229; Last updated: Feb. 19, 2013.

ClinicalTrials.gov, "To Evaluate the Safety, Local Tolerability, PK and PD of LDE225 on Sporadic Superficial and Nodular Skin Basal Cell Carcinomas(sBCC)" National Institute of Health Clinical Trial Identifier No. NCT01033019; Last updated: Apr. 28, 2012.

ClinicalTrials.gov, "Trial Comparing the Effects of Intermittent Vismodegib Versus Photodynamic Therapy in Patients With Multiple Basal Cell Carcinomas" National Institute of Health Clinical Trial Identifier No. NCT01556009; Last updated: Jul. 30, 2013.

ClinicalTrials.gov, "Vismodegib for Treatment of Basal Cell Carcinoma (Erivedge)" National Institute of Health Clinical Trial Identifier No. NCT01543581; Last updated: Apr. 17, 2012.

ClinicalTrials.gov, "Vismodegib in Treating Patients With Basal Cell Carcinoma" National Institute of Health Clinical Trial Identifier No. NCT01631331; Last updated: Aug. 28, 2013.

Colmont CS et al., "CD200-expressing human basal cell carcinoma cells initiate tumor growth" *PNAS*, approved Nov. 29, 2012, www.pnas.org/cgi/doi/10.1073/pnas.1211655110, pp. 1-6.

Cooney E, "New Potential targets discovered for treating squamous cell lung cancers" Broad Communications, Sep. 9, 2012; http://www.broadinstitute.org/news/4323.

Cucchi D et al., "Hedgehog signaling pathway and its targets for treatment in basal cell carcinoma" *Journal of Experimental Pharmacology*, 2012, 4:173-185.

Curis, "Curis Announces Approval of Erivedge(R) in Australia", posted May 10, 2013; http://files.shareholder.com/downloads/ABEA-5QPVEJ/3028962009x0x662920/71345d93-2d91-4871-949a-6f1d3caf6e1c/CRIS_News_2013_5_10_General_Releases.pdf.

Curis, Curis Announces Initiation of a Roche-Sponsored Phase 1 b/2 Study of Erivedge(R) (vismodegib) in Relapsed/Refractory AML and High Risk MDS, posted Oct. 4, 2013; http://files.shareholder.com/downloads/ABEA-5QPVEJ/3028962009x0x694836/5e3e7694-1901-4fc1-9b19-84bf774cf1d6/CRIS_News_2013_10_4_General_Releases.pdf.

Dann SG et al., "mTOR Complex1-S6K1 signaling: at the crossroads of obesity, diabetes and cancer" *Trends in Molecular Medicine*, 2007, doi:10.1016/j.molmed.2007.04.002, pp. 1-8.

Dean W, "Is DHEA Contraindicated in Men with Benign Prostatic Hypertrophy (BPH) or Prostate Cancer" *Vitamin Research Products*, printed Mar. 12, 2014, http://www.vrp.com/hormone-support/hormone-support/dhea-dehydroepiandrosterone-is-dhea-contraindicated-in-men.

Duchesne G, "Localised prostate cancer: current treatment options" *Urology*, pp. 768-771 (reprinted from Australian Family Physician vol. 40, No. 10, Oct. 2011).

Ekman SL and Hirsch FR, "An Update on New and Emerging Therapies for NSCLC CME" *Medscape*, Posted: May 31, 2012, 1-20; This article is part of a CME certified activity. The complete activity is available at: http://www.medscape.org/viewprogram/32487.

Fantini F et al., "Metastatic Basal Cell Carcinoma With Squamous Differentiation" *Arch Dermatol.*, 2008, 144(9):1186-1188.

Fellner C, "Vismodegib (Erivedge) for Advanced Basal Cell Carcinoma" *Drug Forecast / P&T*, 2012, 37(12)670-682.

Freedland SJ and Moul JW, "Prostate specific antigen recurrence after definitive therapy" *Journal of Urology*, 2007, 177(6):1985-91.

Garnick MB, "How to handle a relapse after treatment for prostate cancer" *Harvard Medical School, Prostate Knowledge*, http://www.harvardprostateknowledge.org/how-to-handle-a-relapse-after-treatment-for-prostate-cancer, Originally posted Apr. 1, 2007; last reviewed Apr. 22, 2011.

Giaccone G, "The Potential of Antiangiogenic Therapy in Non-Small Cell Lung Cancer" *Clinical Cancer Research*, 2007, 13:1961-1970.

Giambelli C et al., "Repurposing an old anti-fungal drug as a Hedgehog inhibitor" *Protein & Cell*, 2010, 1(5):417-418.

Green A et al., "Daily sunscreen application and betacarotene supplementation in prevention of basal-cell and squamous-cell carcinomas of the skin: a randomised controlled trial" *The Lancelet*, 1999, 354:723-729.

Hale C, "ODAC Votes to Nix Amgen's Drug Xgeva for Proposed Prostate Cancer Indication" *The Cancer Letter*, 38(7), Feb. 17, 2012.

Hathaway C et al., "Exclusivity Strategies in the United States and European Union" *The Food and Drug Law Institute: Update*, 2009, 3:34-39; http://www.lw.com/upload/pubContent/_pdf/pub2655_1.pdf.

Higano CS, "Side Effects of Androgen Deprivation Therapy: Monitoring and Minimizing Toxicity" *Urology*, 2003, 61(Supplement 2A):32-38.

Hitt E, "Avoiding Prostate Cancer Screening Might be Costly" *Urology Health Specialists*, American Urological Association (AUA) 2012 Annual Scientific Meeting: Abstract LBA4. Presented May 22, 2012; http://www.uhsurology.com/news_article_name/Avoiding_Prostate_Cancer_Screening_Mi ght_Be_Costly.aspx.

Hotte SJ and Saad F, "Urologic Oncology: Current management of castrate-resistant prostate cancer" *Current Oncology*, 2010, 17(2):S72-S79.

Hou X and Flaig TW, "Redefining Hormone Sensitive Disease in Advanced Prostate Cancer" *Advances in Urology*, 2012, Article ID 978531, 6 pages.

Howlander N et al., "PSA doubling time (PSA-DT) during the "off treatment" interval in men with biochemical relapse of prostate

(56) References Cited

OTHER PUBLICATIONS cancer treated with intermittent androgen suppression (IAS)" *Journal of Clinical Oncology*, (Meeting Abstracts) Jun. 2005, 23(16), Suppl. 4670.

Jefford M et al., "Metastatic Basal Cell Carcinoma: Rapid Symptomatic Response to Cisplatin and Paclitaxel" *ANZ J. Surg.*, 2004, 74:704-705.

Kasper M et al., "Basal cell carcinoma—molecular biology and potential new therapies" *Journal of Clinical Investigation*, 2012, 122(2):455-463.

Keizman D et al., "Lenalidomide in Nonmetastatic Biochemically Relapsed Prostate Cancer: Results of a Phase I/II Double-Blinded, Randomized Study" *Clinical Cancer Research*, 2010, 16:5269-5276.

Kim D et al., "Abstract LB-223: An open-label, exploratory phase II study of oral itraconazole for the treatment of basal cell carcinoma" *Cancer Research*, 2012, 72(8); Proceedings: AACR 103rd Annual Meeting 2012—Mar. 31-Apr. 4, 2012; Chicago, IL.

Kim DJ et al., "Open-Label, Exploratory Phase II Trial of Oral Itraconazole for the Treatment of Basal Cell Carcinoma" *Journal of Clinical Oncology*, Published ahead of print on Feb. 3, 2014. http://jco.ascopubs.org/cgi/doi/10.1200/JCO.2013.49.9525.

Kim J et al., "Itraconazole and Arsenic Trioxide Inhibit Hedgehog Pathway Activation and Tumor Growth Associated with Acquired Resistance to Smoothened Antagonists" *Cancer Cell*, 2013, 23:23-24.

Kim J et al., "Itraconazole, a Commonly Used Antifungal that Inhibits Hedgehog Pathway Activity and Cancer Growth" *Cancer Cell*, 2010, 17(4):388-399.

Klayton TL et al., "PSA Doubling Time Predicts for the Development of Distant Metastases for Patients Who Fail 3DCRT or IMRT Using the Phoenix Definition" *Practical Radiation Oncology*, 2011, 1(4):235-242.

Klein R et al., "Cost-effectiveness of pemetrexed plus cisplatin as first-line therapy for advanced nonsquamous non-small cell lung cancer" *Journal of Thoracic Oncology*, 2009, 4(11):1404-1414. Abstract.

Klemm J and MHR SR, "Prostate Cancer" Published Online May 24, 2012; http://www.ajmc.com/publications/evidence-based-oncology/2012/2012-2-vol18-n3/prostate-cancer/1.

Kolata G and Pollack A, "Costly cancer drug offers hope, but also a dilemma" *The New York Times*, Jul. 6, 2008.

Krader CG, "Nearly 200,000 non-metastatic prostate cancer patients on androgen deprivation therapy" *Urology Times*, published Jul. 1, 2012; http://urologytimes.modernmedicine.com/print/122666.

Kunze KL et al., "Stereochemical Aspects of Itraconazole Metabolism In Vitro and In Vivo" *Drug Metabolism and Disposition*, 2006, Epub Jan. 13, 2006, 34(4):583-590, and as corrected in "Correction to Stereochemical Aspects of Itraconazole Metabolism In Vitro and In Vivo" *Drug Metabolism and Disposition*, 2012, 40(12):2381.

Lavery HJ et al., "Actual total hospital costs of primary localized prostate cancer treatments analyzed by risk group" ASCO University, Meeting Library, Abstracts, 2012 ASCO Annual Meeting, *Journal of Clinical Oncology*, 2012, 30:Suppl. abstract e15164; http://meetinglibrary.asco.org/content/98073-114.

Lewis RE, "Current Concepts in Antifungal Pharmacology" *Symposium on Antimicrobial Therapy*, Mayo Clin. Proc. 2011, 86(8):805-817.

Lin TL and Matsui W, "Hedgehog pathway as a drug target: Smoothened inhibitors in development" *OncoTargets and Therapy*, 2012, 5:47-58.

Liu H et al., "Clinical implications of hedgehog signaling pathway inhibitors" *Chinese Journal of Cancer*, 2011, 30(1):13-26.

Lucas BS et al., "Design of 1-piperazinyl-4-arylphthalazines as potent Smoothened antagonists" *Bioorganic & Medicinal Chemistry Letters*, 2010, 20(12):3618-22.

Matsubara H, et al., "Non-small cell lung carcinoma therapy using mTOR-siRNA" *International Journal of Clinical and Experimental Pathology*, 2012, 5(2):119-125.

Matsui WH "Abstract CN06-04: The hedgehog signaling pathway in cancer" *Molecular Cancer Therapeutics*, 2011, Meeting Abstract, 10(11):Supplement 1.

Maverick NY "J&J unblind Zytiga phase 3 trial in pre-chemotherapy castrate-resistant prostate cancer" Pharma Strategy Blog, Mar. 8, 2012, http://pharmastrategyblog.com/2012/03/jj-unblind-zytiga-phase-3-trial-in-pre-chemotherapy-castrate-resistant-prostate-cancer.html/.

Merseburger AS et al., "Perspectives on treatment of metastatic castration-resistant prostate cancer" *Oncologist*, 2013, 18(5):558-67, abstract.

Morel H and Murphy R, "Dealing With REMS Challenges in Drug Commercialization" *Pharmaceutical Commerce*, Jul./Aug. 2009, 1-4.

Moul JW et al., "Early versus delayed hormonal therapy for prostate specific antigen only recurrence of prostate cancer after radical prostatectomy." *Journal of Urology*, 2004, 171:1141-1147.

Moul JW et al., "Rising PSA in Nonmetastic Prostate Cancer" *Oncology, Areas of Confusion in Oncology*, 2007, 21(12):1436-1445. Abstract.

Moul JW, "Prostate Specific Antigen Only Progression of Prostate Cancer" The Journal of Urology, Review Article, 2000, 163:1632-1642.

Mullin TM, "Patient-Focused Drug Development Public Meeting" FDA Center for Drug Evaluation and Research, Oct. 25, 2012, www.fda.gov.

Murgo AJ, "FDA Requirements for Approval of Drugs to Treat Non-Small Cell Lung Cancer" *Center for Drug Evaluation and Research: Guidance for Industry*, Feb. 1997, 1-12.

Nacev BA et al., "The Antifungal Drug Itraconazole Inhibits Vascular Endothelial Growth Factor Receptor 2 (VEGFR2) Glycosylation, Trafficking, and Signaling in Endothelial Cells" *The Journal of Biological Chemistry*, 2011, 286(51):44045-44056. Epub Oct. 24, 2011.

Osanto S and Van Poppel H, "Emerging novel therapies for advanced prostate cancer" *Therapeutic Advances in Urology*, 2012, 4(1)3-12.

Paller CJ and Antonarakis ES, "Sipuleucel-T for the treatment of metastatic prostate cancer: Promise and challenges" *Human Vaccines & Immunotherapeutics*, 2012, 8(4):509-519.

Pan S et al., "Discovery of NVP-LDE225, a Potent and Selective Smoothened Antagonist" *ACS Medicinal Chemistry Letters*, 2010; 1(3): 130-134.

Pantuck AJ et al., "Phase II Study of Pomegranate Juice for Men with Rising Prostate-Specific Antigen following Surgery or Radiation for Prostate Cancer" *Clinical Cancer Research*, 2006, 12:4018-4026.

Pasqualotto AC and Denning DW, "Generic substitution of itraconazole resulting in subtherapeutic levels and resistance" *International Journal of Antimicrobial Agents: Letters to the Editor*, 2007, 30:93-94.

Patel R and Goldenberg G, "Basal Cell Carcinoma, Hedgehog and Vismodegib" Dermquest.com; posted Mar. 20, 2012; https://www.dermquest.com/expert-opinions/research-updates/2012/basal-cell-carcinoma,-hedgehog-and-vismodegib/.

Pazdur R, "Endpoints for Assessing Drug Activity in Clinical Trials" *The Oncologist*, 2008, 13(2):19-21.

Peck P, "Cancer Treatment Costs Worry Oncologists" ABC News, Orlando, FL, May 30, 2009, http://abcnews.go.com/Health/CancerPreventionAndTreatment/story?id=7715284&page=1.

Perrone M, "FDA questions Amgen drug for prostate cancer" *Associated Press*, Feb. 6, 2012; http://abclocal.go.com/wpvi/story?section=news/national_world&id=8532916&pt=print.

Peukert S and Miller-Moslin K, "Small-Molecule Inhibitors of the Hedgehog Signaling Pathway as Cancer Therapeutics" *ChemMedChem*, 2010, 5(4):500-512.

Pezaro CJ et al., "Abiraterone acetate: redefining hormone treatment for advanced prostate cancer" *Drug Discoveries Today*, 2012, 00:1-16.

Pollack A, "New Drug for Prostate Cancer Gets F.D.A. Nod" *The New York Times, Business Day*, Published Aug. 31, 2012, http://www.nytimes.com/2012/09/01/business/fda-approves-prostate-cancer-drug.html?_r=3&.

(56) References Cited

OTHER PUBLICATIONS

Preidt R "Gilotrif for NSCLC, FDA Approves New Drug for Advanced Lung Cancer" *WebMD*, as posted Jul. 12, 2013, http://www.webmd.com/lung-cancer/news/20130712/fda-approves-new-drug-for-advanced-lung-cancer.
Prentice AG and Glasmacher A, "Making sense of itraconzaole pharmacokinetics" *Journal of Antimicrobial Chemotherapy*, 2005, 56(S1):i17-i22.
Proctor J et al., "Hedgehog Signaling in Castration Resistant Prostate Cancer" *AACR Annual Meeting*, Apr. 17-21, 2010, Abstract #3857.
Rini BI et al., "Prostate-Specific Antigen Kinetics as a Measure of the Biologic Effect of Granulocyte-Macrophage Colony-Stimulating Factor in Patients with Serologic Progression of Prostate Cancer" *Journal of Clinical Oncology*, 2003, 21:99-105.
Robarge KD et al., "GDC-0449—A potent inhibitor of the hedgehog pathway" *Bioorganic & Medicinal Chemistry Letters*, 2009, 19(19):5576-81.
Roberts SG et al., "PSA doubling time as a predictor of clinical progression after biochemical failure following radical prostatectomy for prostate cancer." *Mayo Clinical Proceedings*, 2001, 76(6):576-581; Abstract.
Roehr B, "Vismodegib effective against basal cell nevus syndrome" *Dermatology Times*, Publish date: Aug. 1, 2012, http://dermatologytimes.modernmedicine.com/dermatology-times/news/clinical/ clinical-pharmacology/vismodegib-effective-against-basal-cell-nevus-.
Rominger CM et al., "Evidence for Allosteric Interactions of Antagonist Binding to the Smoothened Receptor" *Journal of Pharmacological and Experi-mental Therapeutics*, 2009; 329(3):995-1005.
Rudin C et al., "Phase 2 Study of Pemetrexed and Itraconazole as Second-Line Therapy for Metastatic Nonsquamous Non-Small-Cell Lung Cancer" *Journal of Thoracic Oncology*, 2013, 8(5):619-623.
Rudin C et al., "Treatment of Medulloblastoma with Hedgehog Pathway Inhibitor GDC-0449" *New England Journal of Medicine*, 2009, 361(12):1173-1178.
Rudin CM "Beyond the Scalpel: Targeting Hedgehog in Skin Cancer Prevention" *Cancer Prevention Research*, 2010, 3:1.
Saad F and Hotte SJ, "Guidelines for the management of castrate-resistant prostate cancer" *Canadian Urological Association Journal*, Canadian Urological Association, 2010, 4(6):380-384.
Saad F and Pantel K, "The Current Role of Circulating Tumor Cells in the Diagnosis and Management of Bone Metastases in Advanced Prostate Cancer" *Future Oncology*, 2012, 8(3):321-331.
Saad F, "Bone Metastases in Advanced Prostate Cancer" *Business Briefing: European Pharmacotherapy*, 2005, 2-6.
Sahebjam S et al., "The Utility of Hedgehog Signaling Pathway Inhibition for Cancer" *The Oncologist*, 2012, 17:1090-1099.
Saxena R, "Non-small Cell Lung Cancer drugs—where does the Future lie" Nov. 6, 2012; http://pharmaceuticalintelligence.com/2012/11/06/non-small-cell-lung-cancer-drugs-where-does-the-future-lie/.
Schmid HP et al., "Prostate Specific Antigen Doubling Time as Auxiliary End Point in Hormone Refractory Prostatic Carcinoma" *European Urology*, 2003, 43:28-30.
Sharifi N et al., "An update on androgen deprivation therapy for prostate cancer" *Endocrine-Related Cancer*, 2010, 17:R305-R315.
Sheng T et al., "Activation of the hedgehog pathway in advanced prostate cancer" *Molecular Cancer*, 2004, 3:29.
Shi W et al., "Itraconazole Side Chain Analogues: Structure—Activity Relationship Studies for Inhibition of Endothelial Cell Proliferation, Vascular Endothelial Growth Factor Receptor 2 (VEGFR2) Glycosylation, and Hedgehog Signaling" *Journal of Medicinal Chemistry*, 2011, 54:7362-7374.
Simon A et al., "Itraconazole prophylaxis in pediatric cancer patients receiving conventional chemotherapy or autologous stem cell transplants" *Support Care Cancer*, 2007, 15(2):213-220.
Siu L et al., "A first-in-human, phase I study of an oral hedgehog (HH) pathway antagonist" *Journal of Clinical Oncology*, 2010; 28:15s (suppl; abstr 2501).

Slater E, "Metastatic Castration Resistant Prostate Cancer (CRPC)" *PCRI Insights*, Posted Aug. 6, 2010; 12-15.
Smith J and Andes D, "Therapeutic Drug Monitoring of Antifungals: Pharmacokinetic and Pharmacodynamic Considerations" *Therapeutic Drug Monitoring: Proceedings Paper*, 2008:30(2):1-6.
Smith MR et al., "Denosumab and bone-metastasis-free survival in men with castration-resistant prostate cancer: results of a phase 3, randomised, placebo-controlled trial" *The Lancelet*, 2012, 379:39-46.
Staton T, "Zytiga, Xtandi will help pump prostate cancer market to $9.1B" *FiercePharma*, posted Nov. 13, 2012; http://www.fiercepharma.com/story/ zytiga-xtandi-will-help-pump-prostate-cancer-market-91b/2012-11-13.
Stenger M, "Imiquimod 5% Cream Inferior to Surgical Excision in Modular and Superficial Basal Cell Carcinoma" *The ASCO Post*, posted Dec. 23, 2013; http://www.ascopost.com/ViewNews.aspx?nid=11875.
Tang JY et al., "New drug found effective against rare form of basal cell skin cancer" *ScienceDaily*, posted Jun. 6, 2012; www.sciencedaily.com/releases/2012/06/120606193444.htm.
Tang T et al., "Targeting Superficial or Nodular Basal Cell Carcinoma with Topically Formulated Small Molecule Inhibitor of Smoothened" *Clinical Cancer Research*, 2011, 17:3378-3387.
Taplin ME, "Biochemical (Prostate-Specific Antigen) Relapse: An Oncologist' Perspective" *Biochemical Relapse, Reviews in Urology*, 2003(Suppl. 2):S3-S13.
Thobe MN et al., "From Prostate to Bone: Key Players in Prostate Cancer Bone Metastasis" *Cancers*, 2011, 3:478-493.
Tracey E, "Hedgehog Inhibition" Johns Hopkins Medicine, Medical News Commentary, posted Jun. 8, 2012; http://podblog.blogs.hopkinsmedicine.org/2012/06/08/hedgehog-inhibition/.
Von Hoff D et al., "Inhibition of the Hedgehog Pathway in Advanced Basal-Cell Carcinoma" *New England Journal of Medicine*, 2009; 361(12):1164-72.
White T, "Studies show new drug to be effective in treating skin cancer, researchers say" *Stanford School of Medicine*, posted Jun. 6, 2012; http://med.stanford.edu/ism/2012/june/hedgehog.html.
Wu C et al., "Overcoming cisplatin resistance by mTOR inhibitor in lung cancer" *Molecular Cancer*, 2005, 4:25.
Xu J et al., "Cholesterol trafficking is required for mTOR activation in endothelial cells" PNAS, 2010, 107(10):4764-4769.
Yauch RL et al., "Smoothened Mutation Confers Resistance to a Hedgehog Pathway Inhibitor in Medulloblastoma" *Science*, 2009, 326(5952):572-574.
Zalcman G et al., "Update on Nonsmall cell lung cancer" *European Respiratory Update*, 2010, 19:117, 173-185.
Zhang YJ et al., "Targeting the mTOR kinase domain: the second generation of mTOR inhibitors" *Drug Discovery Today*, 2011, 16(7/8):325-331.
Zhao C et al., "Hedgehog signalling is essential for maintenance of cancer stem cells in myeloid leukaemia" *Nature Letters*, Published online Jan. 25, 2009, pp. 1-5.
"Issues Concerning Development of Products for Treatment of Non-Metastatic Castration-Resistant Prostate Cancer (NM-CRPC)" *FDA Presentation, ODAC Meeting*, FDA Committee chaired by Wyndam Wilson, M.D., Ph.D., Chairperson ODAC, Presented Sep. 14, 2011, FDA White Oak Campus, Silver Springs, Maryland.
"Degarelix depot (Firmagon) for advanced, hormone-dependent prostate cancer" *National Horizon Scanning Centre*, Sep. 2007, Birmingham, London, England.
BLA 125320/28 Denosumab (Xgeva™) Amgen Inc., *FDA ODAC Briefing Document*, FDA Committee chaired by Wyndam Wilson, M.D., Ph.D., Chairperson ODAC, Presented Feb. 8, 2012, FDA White Oak Campus, Silver Springs, Maryland, 21 pages.
"Prostate Cancer Patient's Guide to Hormone Therapy" *Us Too Prostate Cancer*, http://www.ustoo.org/PDFs/Hormone_Brochure.pdf, 2007, Downers Grove, Illinois, Sep. 2, 2012, 24 pages.
"Prostate Cancer" *American Cancer Society*, Aug. 22, 2013; cancer.org.
"Cancer Statistics 2009: A Presentation from the American Cancer Society" *American Cancer Society*, 2009, cancer.org.
"Cancer Facts & Figures 2013" *American Cancer Society*, Atlanta: American Cancer Society, 2013.

(56) References Cited

OTHER PUBLICATIONS

"Therapeutic Options for Advanced NSCLC: Second Line" *Clinical Care Options Oncology*, Updates in Community Oncology 2011: A Focus on Non-Small-Cell Lung Cancer, clinicaloptions.com/oncology.

"Therapeutic Options for Advanced NSCLC: First Line" *Clinical Care Options Oncology*, Updates in Community Oncology 2011: A Focus on Non-Small-Cell Lung Cancer, clinicaloptions.com/oncology.

Antonarakis E et al., "A non-comparative randonmized phase 2 study of two dose-levels of itraconazole in men with metastatic castration-resistant prostate cancer (mCRPC): a DOD/PCCTC trial" ASCO, Presented Jun. 4, 2011, Chicago, Illinois.

Bale SJ, "Gorlin Syndrome: More than skin deep" Presented Mar. 6, 2013, U. Washington.

Berg D, "Basal Cell Nevus Syndrome" *University of Washington*, Apr. 9, 2011; http://www.docstoc.com/docs/75751280/Slide-1-Basal-Cell-Carcinoma-Nevus-Syndrome-Life-Support-Network.

CURIS Corporate Overview, Sep. 12, 2011, NASDAQ: CRIS (42 pages).

Germansky R, "Alimta (Pemetrexed)" *Alimta Pemetrexed*, www.alimta.com, posted May 27, 2012, http://www.docstoc.com/docs/121542264/Alimta-cancer-asbestos, pptx 19 slides.

Glorioso DF JR, "Treatment of [Patients with] Late State Cancers—the Palliative Care Approach"; Jul. 24, 2013; http://www.acoi.org/StarrPass/ Glorioso.pdf.

Haffner ME, "How do We Get to Treatments? The Orphan Drug Act Incentives to Drug Development" From Bench to Bedside to Practice: a Practical Course—Genetic Alliance Annual Conference, Jul. 2006, 1-19.

Kludze M, "Risk Evaluation and Mitigation Strategy (REMS): Addressing Challenges and Opportunities for Stakeholders" REMS Presentation, Feb. 3, 2011.

Maitra A, "The Hedgehog Signaling Pathway in Pancreatic Cancer: Therapeutic Opportunities and Biomarker Discovery" Johns Hopkins Medical Institution, Nov. 8, 2011, 26 slides.

Nguyen DM et al., "Inhibition of the Hedgehog (HH) Signal Transduction Pathway Significantly Supresses Survival of Malignant Pleural Mesothelioma Cells in vitro" AATS 93$^{rd}$ Annual Meeting, Presented May 6, 2013, University of Miami, Miami, FL.

Nouri K Etal., "Chapter 6: Basal Cell Carcinoma" Skin Cancer, New York: McGraw Hill 2007, pp. 61-85.

Radke E and Linkov F, "Epidemiology of Prostate Cancer" *University of Pittsburgh Cancer Institute*; Nov. 17, 2009; http://www.manyppt.com/download.php?key=EpidemiologyofProstateCancer&url=http://www.pittedu/~super4/34011-35001/34031.ppt.

Smith MR et al., "Effect of Denosumab on Prolonging Bone-Metastasis Free Survival (BMFS) in Men With Non-Metastatic Castrate-Resistant Prostate Cancer (CRPC) Presenting With Aggressive PSA Kinetics" Oral—Final for Presentation—Presented Jan. 30, 2012, Chicago, Illinois.

West H, "Biomarkers for Prognosis and Prediction in Advanced NSCLC" *Clinical Care Options Oncology Presentation*; Presented Nov. 23, 2011, Seattle, Washington.

Yoo SS, "GDC-0449: From Corn Lilies to a Cure" *Northwestern University*, BCCNS Symposium, Presented Sep. 19, 2009, Chicago, Illinois, 38 slides.

Scagliotti GV et al., "Overall survival improvement in patients with lung cancer and bone metastases treated with denosumab versus zoledronic acid: Subgroup analysis from a randomized phase 3 study" Journal of Thoracic Oncology. 2012, 7(12):1823-1829.

"Per-Patient Clinical Trial Costs Rise 70% in Three Years"; Jul. 15, 2011; http://www.cuttingedgeinfo.com/2011/per-patient-clinical-trial-costs.

"U.S. Phase IV Budgets Top $12,000 Per Patient"; Sep. 22, 2011; http://www.cuttingedgeinfo.com/2011/phase-iv-budgets-per-patient/.

Carroll J, "Survey: Clinical trial costs spike on bigger staffs, recruiting costs" Jul. 27, 2011; http://www.fiercebiotech.com/story/survey-clinical-trial-costs-spike-bigger-staffs-recruiting-costs/2011-07-27.

Pomerantseva V, "Clinical Data Cleaning and Validation Steps" Apr. 15, 2009; http://www.pharmpro.com/articles/2009/04/clinical-data-cleaning-and-validation-steps.

"Generic Sporanox Availability" Drugs.com; Mar. 13, 2014; http://www.drugs.com/availability/generic-sporanox.html.

"Itraconazole" Dec. 30, 2013; http://www.dermnetnz.org/doctors/fungal-infections/antifungal.html#itra.

"Sporanox™ capsules spec sheet" Aug. 2013, http://home.intekom.com/pharm/janssen/sporanox.html.

"SUBA®-itraconazole"; Source: Itraconazole bioavailability study CM4799 Nov. 17, 2009 Halcygen Pharmaceuticals Ltd (Mayne Pharma), Research Note—Patersons Securities Limited 14.

"Return to list of Lilly drugs" Alimta (LY231614); 2008; http://www.lilytrials.com/results/alimata.pdf.

"Patient Information" Alimta® (uh-LIM-tuh) Sep. 2013, http://pi.lilly.com/us/alimta-ppi.pdf.

"In Study E4599, Avastin plus PC (paclitaxel/carboplatin) set a high bar vs. PC alone in first-line metastatic non-squamous NSCLC" Apr. 13, 2014; http://www.avastin-hcp.com/indications/nsclc/ efficacy-data#study_results.

"Lung Cancer Treatments and drugs" by Mayo Clinic Staff, Lung cancer surgery, Mar. 19, 2014, http://www.mayoclinic.org/diseases-conditions/lung-cancer/basics/treatment/con-20025531?p=1.

"Lung Cancer: A guide for journalists on Non-Small Cell Lung Cancer (NSCLC) and its treatment" Roche Group (n.d.); pp. 1-12; http://www.roche.com; Retrieved Jan. 2014, from Roche: ttp://www.roche.com/med-lung-cancer.pdf.

"Non Small Cell Lung Cancer" Moderator: Dr. R. Kapoor (94 slides); Sep. 12, 2012; http://www.scribd.com/doc/6678882/Non-Small-Cell-Lung-Cancer.

"FDA-Approved Non-Small Cell Lung Cancer (NSCLC) Treatments" Nov. 21, 2013; http://media.empr.com/documents/2/onco_nsclct(50)_1068.pdf.

McKeage MJ and Jameson MB, "Comparative outcomes of squamous and non-squamous non-small cell lung cancer (NSCLC) patients in phase II studies of ASA404 (DMXAA)—retrospective analysis of pooled data" *Journal of Thoracic Disease*, 2010, 2:199-204.

"Pemetrexed (for MPM), Committee to Evaluate Drugs (CED)" Ontario, posted Jul. 2007; http://www.health.gov.on.ca/en/pro/programs/drugs/ced/pdf/ pemetrexed.pdf.

"Primary Progression-Free Survival Endpoint Met in Phase III Study of Nintedanib Plus Docetaxel in Second-Line Advanced NSCLC" Jun. 3, 2013, http://www.prnewswire.com/news-releases/primary-progression-free-survival-endpoint-met-in-phase-iii-study-of-nintedanib-plus-docetaxel-in-second-line-advanced-nsclc-209900911.html.

Barlesi F, "Randomized Phase III Trial of Maintenance Bevacizumab With or Without Pemetrexed After First-Line INduction with Bevacizumab, Cisplatin, and Pemetrexed in Advanced NonSqaumous Non-Small Cell Lung Cancer: AVAPERL (MO 22089)"; Aug. 20, 2013, http://jco.ascopubs.org/content/early/2013/07/03/ JCO.2012.42.3749?papetoc.

"Stage 4 Non-Small Cell Lung Cancer, Excerpted from Lung Cancer and Mesotheliomoa" 20.1-20.71; 2009, http://www.lungcancerclaims.com/Stage%204%20nonsmall%20cell%20lung%20cancer.htm.

"Targeted therapies for non-small cell lung cancer"; May 22, 2013; http://www.cancer.org/cancer/lungcancer-non-smallcell/detailedguide/non-small-cell-lung-cancer-treating-targeted-therapies.

"Targeted Therapy for Lung Cancer" 1999; http://www.lung-cancer.com/targeted-therapy.html.

Chen W et al., "Cost-Effectiveness of Epidermal Growth Factor Receptor Mutation Testing for Patients with Advanced Non-Small Cell Lung Cancer" 2012; Toronto Health Economics and Technology Assessment, University of Toronto.

Pilz LR et al., "Statistical considerations and endpoints for clinical lung cancer studies: can progression fee survival (PFS) substitute

(56) References Cited

OTHER PUBLICATIONS overall survival (OS) as a valid endpoint in clinical trials for advanced non-small-cell lung cancer?" *Translational Lung Cancer Research*, Mar. 2012, 1:1:26-35.
"Treatment of Non-Small-Cell Lung Cancer" Sep. 13, 2012; http://www.webmd.com/lung-cancer/guide/no-small-cell-lung-cancer?page=2.
"Non-Small Cell Lung Carcinoma Chemotherapy"; Aug. 15, 1999; http://www.healthcommunities.com/lung-cancer/chemotherapy-non-small-cell-lung-carcinoma.shtml.
"Xalkori—Treatment for Non Small Cell Lung Cancer" Sep. 13, 2012; http://www.drugdevelopment-technology.com/projects/xalkori---treatment-for-nonsmall-cell-lung-cancer/.
"Avastin is approved for" Apr. 16, 2014; http://www.avastin.com/patient/ overview/side-effects/.
"IPI-926 vs GDC-0449 vs Itraconazole" Jun. 3, 2011; http://98.139.21.31/search/srpcache?ei=UTF-8&p=IPI-926+vs+GDC-0449+vs+Itraconazole%2C+List+of+Clinical+Hedgehog+Pathway+Cancers&pvid=TpkH5zk4LjHZuRO9Uzx4ZQvcMTc0LINVgWT_9TMI&fr=yfp-t-300&u=http://cc.bingj.com/cache.aspx?q=IPI-926+vs+GDC-0449+vs+Itraconazole%2c+List+of+Clinical+Hedgehog+Pathway+Cancers&d=4733690924960545&mkt=en-US&setlang=en-US&w=ztVqMX3cYMlooj5ExYwZwKDaLiwkr2JY&icp=1&.intl=us&sig=ZZ8G8Kqb7O_hPrSYrnFu4A--.
Stadler W, "Management Protocols for Advanced Prostate Cancer" University of Chicago, Aug. 16, 2012.
McBride R, "Cabozantinib—Top 10 Late-Stage Cancer Drugs—2012" FierceBiotech.com; Apr. 17, 2012, http://www.fiercebiotech.com/node/317526/ print.
"Canada prostate cancer stats" www.cancer.ca; Aug. 22, 2012; http://www.cancer.ca/Canada-wide/About%20cancer/Cancer%20statistics/Stats%20at%20a%20glance/Prostate%20cancer.aspx?sc_lang=en#ixzz24ln3eTQU.
"Chapter 7. Prostate cancer in PSA relapse" Clinical Practice Guidelines in the NHS, Ministry of Health and Consumer Affairs, 2008, 70-79; http://www.guiasalud.es/egpc/traduccion/ingles/ cancer_prostata/completa/documentos/partado07/ CP%20progresion%20bioquimica.pdf.
"Recently Introduced Products" *Drug Review*, X(6)—Byetta; Jun. 22, 2011; http://www.claimsecure.com/en-CA/content/pdfs/en-CA/DrugReviews/DrugReview_Vol10_Issue6_en.pdf.
"Hormone (androgen deprivation) therapy for prostate cancer" www.cancer.org, Aug. 26, 2013; http://98.139.21.31/search/srpcache?ei=UTF-8&p=%E2%80%9CHormone+%28androgen+deprivation%29+therapy+for+prostate+cancer%E2%80%9D&pvid=qw9n7zk4LjHZuRO9Uzx4ZQOcMTc0LINVhgb_mXp4&fr=yfp-t-300&u=http://cc.bingj.com/cache.aspx?q=%e2%80%9cHormone+(androgen+deprivation)+therapy+for+prostate+cancer%e2%80%9d&d=4668879853782505&mkt=en-US&setlang=en-US&w=UK8cSLrrHrpLKX7rks7Kglk9yiBlhh1T&icp=1&.intl=us&sig=4.11nZXxOe7OicJTtFLzEQ--.
"Icarus Consultants" Feb. 10, 2012; http://icarusconsultants.com/tag/mdv3100/.
"Enzalutamide (MDV3100) Now Available in 10 States as Part of Ongoing Study" http://www.hisprostatecancer.com/prostate-cancer-blog-archive.html (p. 6); originally posted Jun. 6, 2012 at htt://peribc.org/showthread.php/112-MDV3100-%28enzalutamide%29-Now-Available-in-10-states%E2%80%8F.
"PSA Rising Post-Treatment" Prostate Cancer Foundation, printed Apr. 21, 2014; www.pcf.org.; http://www.pcf.org/site/c.leJRIROrEpH/b.5838551/k.6D69/PSA_Rising_PostTreatment.htm.
FDA Approved Drugs: Zoladex (10.8 mg goserelin acetate implant), http://www.centerwatch.com/drug-information/fda-approved-drugs/drug/38/ zoladex-108-mg-goserelin-acetate-implant; approved Jan. 1996.
FDA Approved Drugs: Lupron Depot (leuprolide acetate for depot suspension); http://www.centerwatch.com/drug-information/fda-approved-drugs/drug/40/lupron-depot-leuprolide-acetate-for-depot-suspension; approved Jan. 1996.
FDA Approved Drugs: Eulexin (flutamide); http://www.centerwatch.com/drug-information/fda-approved-drugs/drug/136/eulexin-flutamide; approved Jun. 1996.
FDA Approved Drugs: Lupron Depot (leuprolide acetate for depot suspension); http://www.centerwatch.com/drug-information/fda-approved-drugs/drug/293/lupron-depot-leuprolide-acetate-for-depot-suspension; approved Jul. 1997.
FDA Approved Drugs: Viadur (leuprolide acetate implant); http://www.centerwatch.com/drug-information/fda-approved-drugs/drug/609/viadur-leuprolide-acetate-implant; approved Mar. 2000.
FDA Approved Drugs: Trelstar Depot (triptorelin pamoate); http://www.centerwatch.com/drug-information/fda-approved-drugs/drug/622/trelstar-depot-triptorelin-pamoate; approved Jun. 2000.
FDA Approved Drugs: Trelstar LA (triptorelin pamoate); http://www.centerwatch.com/drug-information/fda-approved-drugs/drug/719/trelstar-la-triptorelin-pamoate; approved Jun. 2001.
FDA Approved Drugs: Zometa (zoledronic acid); http://www.centerwatch.com/drug-information/fda-approved-drugs/drug/763/zometa-zoledronic-acid; approved Feb. 2002.
FDA Approved Drugs: Eligard (leuprolide acetate); http://www.centerwatch.com/drug-information/fda-approved-drugs/drug/736/eligard-leuprolide-acetate; approved Jan. 2002.
FDA Approved Drugs: Degarelix (degarelix for injection); http://www.centerwatch.com/drug-information/fda-approved-drugs/drug/1010/degarelix-degarelix-for-injection; approved Dec. 2008.
FDA Approved Drugs: Xgeva (denosumab); http://www.centerwatch.com/drug-information/fda-approved-drugs/drug/1127/xgeva-denosumab; approved Nov. 2010.
FDA Approved Drugs: Provenge (sipuleucel-T); http://www.centerwatch.com/drug-information/fda-approved-drugs/drug/1100/provenge-sipuleucel-t; approved May 2010.
FDA Approved Drugs: Jevtana (cabazitaxel); http://www.centerwatch.com/drug-information/fda-approved-drugs/drug/1103/jevtana-cabazitaxel; approved Jun. 2010.
FDA Approved Drugs: Zytiga (abiraterone acetate); http://www.centerwatch.com/drug-information/fda-approved-drugs/drug/1151/zytiga-abiraterone-acetate; approved May 2011.
Docetaxel Approval in 2004; May 19, 2004; http://www.cancer.gov/cancertopics/druginfo/fda-docetaxel.
"What are the Prostate Cancer Chemotherapy Drugs" 2008, http://prostate-cancer.com/chemotherapy/treatment-description/prostate-chemotherapy.html.
"Genentech Submits New Drug Application to FDA for Vismodegib for Rare Form of Advanced Skin Cancer" www.gene.com; Sep. 12, 2011; http://www.gene.com/med ia/press-releases/13587/2011-09-12/genentech-submits-new-drug-application-t.
Dlugosz A et al., "Market for basal cell carcinoma" *Nature Reviews Drug Discovery*, 2012, 11:437-438.
"Vismodegib Briefing Package, Pediatric ODAC Subcommittee Meeting" Vismodegib, *Genentech*, ODAC, Presented Nov. 1, 2011, Silver Springs, MD.
"Assessment Report" *European Medicines Agency, Science Medicines Health*, Apr. 25, 2013; EMA/297688/2013, Committee for Medicinal Products for Human Use (CHMP); 7 Westferry Circus, Canary Ward, London.
Takemoto S et al., "Giant basal cell carcinoma: improvement in the quality of life after extensive resection" *Scandinavian journal of plastic and reconstructive surgery and hand surgery*, 2003, 37:181-185. [Abstract].
Randle HW, "Basal cell carcinoma Identification and Treatment of the High-Risk Patient" *Dermatologic Surgery*, 1996, 22:255-261. [Abstract].
Copcu E and Aktas A, "Simultaneous two organ metastases of the giant basal cell carcinoma of the skin" *International Seminars in Surgical Oncology*, 2005, 2(1):1.
Scanlon EF et al., Metastatic basal cell carcinoma. *Journal of Surgical Oncology*, 1980, 15:171-180. [Abstract].
"Basil Cell Carcinoma" Sep. 6, 2012; http://www.dehaveneye.com/disorders/index.php.
Nelson JB "Prevention of Bone Metastases" *Clinical Care Options Oncology*, University of Pittsburgh upmc.com, May 22, 2012, Pittsburgh, Pennsylvania.

(56) References Cited

OTHER PUBLICATIONS

Smith MR, "Preventing Bone Compromise in Patients with Nonmetastic Prostate Cancer" *Clinical Care Options Oncology*, May 22, 2012, Boston, Massachusetts.
OncoGenex Pharmaceuticals, Inc. (NASDAQ: OGXI), OncoGenex ASCO Reception, Key Opinion Leader Panel, OncoGeneX, Chicago, Illinois, 81 slides, retrieved Mar. 4, 2014 from: http://files.shareholdercom/downloads/SNUS/0x0x297752/850cfd08-e540-4479-b058-c300b74fddcf/OncoGenex_ASCO%20Presentation.pdf.
Maynepharma document on SUBA formulation of itraconazole, downloaded on Jan. 5, 2015, dated Oct. 2010.
Stella, V. "Prodrugs as therapeutics" *Expert Opinion Ther. Patents*, 2004, 14(3):277-280.
Wolff, M. *Burger's Medicinal Chemistry and Drug Discovery*, 1994, $5^{th}$ Edition, vol. 1, pp. 975-977.
Testa, B. "Prodrug research: futile or fertile?" *Biochem. Pharm.*, 2004, 68:2097-2106.
Ettmayer, P. et al. "Lessons learned from marketed and investigational prodrugs" *J. Med. Chem.*, 2004, 47(10):2393-2404.
Heretsch, P. et al. "Modulators of the hedgehog signaling pathway" *Bioorg. Med. Chem.*, 2010, 18:6613-6624.
Boogaerts, M.A., et al., "Pharmacokinetics and Safety of a 7-Day Administration of Intravenous Itraconazole followed by a 14-Day Administration of Itraconazole Oral Solution in Patients with Hematologic Malignancy," *Antimicrobial Agents and Chemotherapy*, 2001, vol. 45, No. 3, pp. 981-985.
Mas, C., et al., "Small molecule modulation of HH-GLI signaling: Current leads, trials and tribulations," *Biochemical Pharmacology*, 2010, vol. 80, pp. 712-723.
Poirier, J.M., et al., "Marked intra- and inter-patient variability of itraconazole steady state plasma concentrations," *Therapie*, 1996, vol. 51, No. 2, pp. 163-167 (abstract only).
Takagi, K., et al., "Successful treatment of *Aspergillus* spondylodiscitis with high-dose itraconazole in a patient with acute myelogenous leukemia," *Leukemia*, 2001, vol. 15, No. 10, pp. 1670-1671.
Vandewoude, K., et al., "Concentrations in plasma and safety of 7 days of intravenous itraconazole followed by 2 weeks of oral itraconazole solution in patients in intensive care units," *Antimicrobial Agents and Chemotherapy*, 1997, vol. 41, No. 12, pp. 2714-2718.
International Search Report and Written Opinion in International Patent Application No. PCT/US2014/034359, dated Sep. 26, 2014, pp. 1-12.
International Preliminary Report on Patentability in International Patent Application No. PCT/US2014/034359, dated Oct. 29, 2015, pp. 1-8.
Bale, A.E. and Yu, K-P. "The hedgehog pathway and basal cell carcinomas" *Hum Mol Genet.*, 2001, 10(7):757-762.
Barakat, M. et al. "Learning from Jekyll to control Hyde: Hedgehog Signaling in Development and Cancer" *Trends Mol. Med.*, 2010, 16(8):337-348.
Cowey, C. "Targeted therapy for advanced Basal-cell carcinoma: vismodegib and beyond" *Dermatol Ther.*, 2013, 3(1):17-31.
Gailani, M.R. et al. "The role of the human homologue of *Drosophila* patched in sporadic basal cell carcinomas" *Nat Genet.*, 1996, 14(1):78-81.
Genentech. Vismodegib (Erivedge) product insert. 2012, pp. 1-17.
Gorlin, R. "Nevoid basal cell carcinoma (Gorlin) syndrome" *Genet Med.* 2004;6(6):530-539.
Graceway Pharmaceuticals. Imiquimod (Aldara) product insert. 2010, pp. 1-27.
Hahn, H. et al. "Mutations of the Human Homolog of *Drosophila* patched in the Nevoid Basal Cell Carcinoma Syndrome" *Cell*, 1996, 85:841-851.
Hanna, A. and Shevde, L. "Hedgehog signaling: modulation of cancer properies and tumor mircroenvironment" *Mol. Cancer*, 2016, 15:24, pp. 1-14.
Johnson, A. and Dipietro, L. "Apoptosis and angiogenesis: an evolving mechanism for fibrosis" *The FASEB Journal*, 2013, 27:3893-3901.

Lear, J.T. et al. "Gorlin syndrome in the United Kingdom: a survey of patient needs, treatment availability and outcomes" poster presented in 2013.
Machado, M.V. and Diehl, A.M. "Role of Hedgehog Signaling Pathway in NASH" *Int'l J. Mol. Sci.*, 2016, 17:857, pp. 1-13.
Mathias, S.D. et al. "Assessing health-related quality of life for advanced Basal cell carcinoma and Basal cell carcinoma nevus syndrome: development of the first disease-specific patient-reported outcome questionnaires" *JAMA Dermatology*, Feb. 2014 (EPUB Nov. 27, 2013), 150(2):169-176.
Murray, L. "Editorial: The Cell Types of Fibrosis" *Front. Pharmacol.*, 2016, 6:311, pp. 1-2.
Muzio, L.L. "Nevoid basal cell carcinoma syndrome (Gorlin syndrome)" *Orphanet J. Rare Dis.*, 2008, 3:32, pp. 1-16.
Riobo, N. "Cholesterol and its derivatives in Sonic Hedgehog signaling and Cancer" *Curr. Opin. Pharmacol.*, 2012, 12(6):736-741.
Sekulic, A. et al. "Efficacy and safety of vismodegib in advanced basal-cell carcinoma" *N Engl J Med.*, 2012, 366(23):2171-2179.
Tang, J.Y. et al. "Tazarotene: Randomized, Double-Blind, Vehicle-Controlled, and Open-Label Concurrent Trials for Basal Cell Carcinoma Prevention and Therapy in Patients with Basal Cell Nevus Syndrome" *Cancer Prev Res*. 2014 (EPUB Jan. 17, 2014), 7(3):292-299.
Tang, J.Y. et al. "Inhibiting the hedgehog pathway in patients with the basal-cell nevus syndrome" *N Engl J Med.*, 2012, 366(23):2180-2188.
National Drug Monograph, "Vismodegib (Erivedge)", VA Pharmacy Benefits Management Services, Nov. 2013, pp. 1-16.
Wicking, C. et al. "The hedgehog signalling pathway in tumorigenesis and development" *Oncogene*, 1999, 18:7844-7851.
Wang, J. and Chen, X-h. "Progress in Hedgehog signaling pathway and its inhibitors for anti-tumor therapy" *Tumor*, Feb. 2011, 31(2):178-182.
Aberger, F. et al., "Acute myeloid leukemia—strategies and challenges for targeting oncogenic Hedgehog/GLI signaling," *Cell Communication and Signaling*, 2017, pp. 1-11, vol. 15, No. 8.
Arimura, S. et al., "Reduced Level of Smoothened Suppresses Intestinal Tumorigenesis by Down-Regulation of Wnt Signaling" *Gastroenterology*, 2009, 137:629-638.
Bai, Y. et al., "Hedgehog signaling in pancreatic fibrosis and cancer", *Medicine*, Mar. 2016, 95(10):1-10.
Defilipp, Z. et al., "Phase 1 study of the Hedgehog pathway inhibitor sonidegib for steroid-refractory graft-versus-host disease", *Blood Advances*, Oct. 2017, 1(22):1919-1922.
El-Agroudy, N. et al., "Forskolin, a Hedgehog signaling inhibitor attenuates carbon tetrachloride-induced liver fibrosis in rats", *British Journal of Pharmacology*, 2016, 173:3248-3260.
Fabian, S. et al., "Hedgehog-Gli pathway activation during kidney fibrosis", *The American Journal of Pathology*, Apr. 2012, 180(4):1441-1453.
Ghanbari-Azarnier, R. et al. "Targeting Stem Cell Behavior in Desmoid Tumors (Aggressive Fibromatosis) by Inhibiting Hedgehog Signaling" *Neoplasia*, 2013, 15(7):712-719.
Gupta, S. et al., "Reversal of Daunorubicin Resistance in P388/ADR Cells by Itraconazole," *J. Clin. Invest.*, Apr. 1991, pp. 1467-1469, vol. 87.
Hu, L. et al., "An overview of Hedgehog signaling in fibrosis", *Mol Pharmacol*, Feb. 2015, 87:174-182.
Jäger, T. et al., "Thoughts on investigational hedgehog pathway inhibitors for the treatment of cancer," *Expert Opinion on Investigational Drugs*, 2017, pp. 133-136, vol. 26, No. 2.
Kim, B. et al., "Chemoprevention in familial adenomatous polyposis" *Best Pract Res Clin Gastroenterol.*, 2011, 25:607-622.
Kramann, R. "Hedgehog Gli signaling in kidney fibrosis", *Nephrol Dial Transplant*, 2016, 31:1989-1995.
Kramann, R. et al. "Pharmacological GLI2 inhibition prevents myofibroblast cell-cycle progression and reduces kidney fibrosis" *J. Clin. Invest.*, 2015, 125(8):2935-2951.
Kurosawa, M. et al., "Reversal effect of itraconazole on adriamycin and etoposide resistance in human leukemia cells," *Ann Hematol*, 1996, Abstract, pp. 17-21, vol. 72, No. 1.

(56) References Cited

OTHER PUBLICATIONS

Kuznar, W., "Glasdegib, a Hedgehog Inhibitor, Nearly Doubles Survival in Acute Myeloid Leukemia or High-Risk Myelodysplastic Syndrome," retrieved Dec. 18, 2017 from: jhoponline.com/in-the-news-oncology-february-2017/17031-glasdegib-a-hedgehog-inhibitor-nearly-doubles-survival-in-acute-myeloid-leukemia-or-high-risk-myelodysplastic-syndrome, pp. 1-3.

Kwon, H. et al., "Inhibition of Hedgehog signaling ameliorates hepatic inflammation in mice with nonalcoholic fatty liver disease", *Hepatology*, 2016, 63:1155-1169.

Kwong, L. and Dove, W., "APC and its modifiers in colon cancer" *Adv Exp Med Biol.*, 2009, 656:85-106.

Lockhart, N.R. et al., "Itraconazole therapy in a pancreatic adenocarcinoma patient: A case report," *J Oncol Pharm Practice*, 2016, pp. 528-532, vol. 22, No. 3.

Metcalfe, C. et al., "Hedgehog Fights Back: Mechanisms of Acquired Resistance against Smoothened Antagonists," *Cancer Res*, 2011, pp. 5057-5061, vol. 71.

Pantziarka, P. et al., "Repurposing Drugs in Oncology (ReDO)—itraconazole as an anti-cancer agent," *ecancer*, 2015, pp. 1-16, vol. 9.

Plaisant, M. et al., "Inhibition of Hedgehog signaling decreases proliferation and clonogenicity of human mesenchymal stem cells", *PLoS One*, Feb. 2011, 6(2):e16798.

Potter, M. et al. "Strategies for managing systemic fungal infection and the place of itraconazole" *J. Antimicrobial Chemo.*, 2005, 56(Suppl. S1):i49-i54.

Pounds, R. et al., "Repurposing itraconazole for the treatment of cancer (Review)," *Oncology Letters*, 2017, pp. 2587-2597, vol. 14.

Pyczek, J. et al., "Hedgehog signaling activation induces stem cell proliferation and hormone release in the adult pituitary gland" *Scientific Reports*, 2016, 6:24928 (17 pages).

Qualtrough, D. et al., "The Hedgehog Inhibitor Cyclopamine Reduces β-Catenin-Tcf Transcriptional Activity, Induces E-Cadherin Expression, and Reduces Invasion in Colorectal Cancer Cells" *Cancers*, 2015, 7:1885-1899.

Sheikh, A. et al., "Hedgehog pathway inhibitors—current status and future prospects," *Infectious Agents and Cancer*, 2012, pp. 1-2, vol. 7, No. 29.

Song, L. et al., "Crosstalk between Wnt/β-catenin and Hedgehog/Gli signaling pathways in colon cancer and implications for therapy" *Cancer Biol. & Ther.*, 2015, 16:1-7.

Suzman, D.L. et al., "High-dose itraconazole as a non-castrating therapy for a patient with biochemically-recurrent prostate cancer," *Clin Genitourin Cancer*, Apr. 2014, pp. e51-e53, vol. 12, No. 2.

Tsubamoto, H. et al., "Impact of Combination Chemotherapy with Itraconazole on Survival of Patients with Refractory Ovarian Cancer," *Anticancer Research*, 2014, pp. 2481-2488, vol. 34.

Tsubamoto, H. et al., "Impact of Combination Chemotherapy with Itraconazole on Survival for Patients with Recurrent or Persistent Ovarian Clear Cell Carcinoma," *Anticancer Research*, 2014, pp. 2007-2014, vol. 34.

Tsubamoto, H. et al., "Impact of Itraconazole on Survival of Heavily Pre-treated Patients with Triple Negative Breast Cancer," *Anticancer Research*, 2014, pp. 3839-3844, vol. 34.

Varnat, F. et al., "Hedgehog pathway activity is required for the lethality and intestinal phenotypes of mice with hyperactive Wnt signaling" *Mech. Develop.*, 2010, 127:73-81.

Vreugdenhil, G. et al., "Itraconazole and multidrug resistance: possible effects on remission rate and disease-free survivial in acute leukemia," *Ann Hematol*, Sep. 1993, Abstract, pp. 107-109, vol. 67, No. 3.

Young, M. et al., "What are the best routes to effectively model human colorectal cancer?" *Mol. Oncol.*, 2013, 7:178-189.

Zhou, D. et al. "Sonic hedgehog signaling in kidney fibrosis: a master communicator" *Sci. China Life Sci.*, Sep. 2016, 59(9):920-929.

Poirier, J.M. et al., "Marked intra- and inter-patient variability of itraconazole steady state plasma concentrations," *Therapie*, 1996, vol. 51, No. 2, pp. 163-167 (full-text).

Looking for Patient Selection Criteria related to Clinical Outcomes

High Dose Group – Itraconazole trough levels >1000ng/ml @ 4 weeks

Pre PSADT<6 months, <25% PSA change @ 4 weeks

| Patient # High Dose | Patient # on charts | Baseline PSA ng/ml | PSA % Change week 4 result | PSA % Change best result | Pre-PSADT in months | pre-PSA slope | Post-PSADT in months | post-PSA slope | trough itra level at 4 wks - ng/ml | trough itra level at 12 wks - ng/ml | # criteria met |
|---|---|---|---|---|---|---|---|---|---|---|---|
| 44 | 1 | 17.4 | -34.5 | -86.2 | 1.7 | 0.4 | 2.2 | -0.32 | 1400 | 2270 | XXX |
| 23 | 2 | 102.1 | -62 | -74.2 | 1.9 | 0.37 | 4.9 | -0.14 | 3450 | 3680 | XXX |
| 36 | 3 | 13.8 | -59.4 | -59.7 | 1.8 | 0.38 | -40.8 | -0.02 | 3020 | 3500 | XXX |
| 3 | 4 | 22.5 | -30.7 | -45.3 | 2.6 | 0.27 | 9.1 | -0.08 | 1890 | 2710 | XXX |
| 20 | 16 | 23.5 | -31.1 | -43.4 | 10.7 | 0.06 | 9.1 | -0.08 | 1680 | 1890 | XX |
| 45 | 17 | 11.4 | 16.7 | -37.7 | 3.4 | 0.09 | 7.5 | -0.09 | NA | 2760 | XX |
| 28 | 5 | 24.7 | -36.4 | -36.4 | 2.8 | 0.25 | 24.5 | 0.03 | 1220 | 1480 | XXX |
| 41 | 6 | 90.3 | -19.6 | -27.5 | 1.8 | 0.38 | -6.7 | -0.1 | 1430 | 1450 | XXX |
| 27 | 7 | 56.7 | -27 | -27 | 2.9 | 0.24 | 9.1 | 0.08 | 1570 | 2030 | XXX |
| 1 | 8 | 141 | -20.7 | -20.9 | 0.9 | 0.75 | 27.6 | 0.03 | NA | 2250 | XXX |
| 14 | 22 | 3.8 | -15.8 | -15.8 | 2.1 | 0.34 | 3.6 | 0.2 | 707 | 268 | XX |
| 13 | 9 | 20.3 | -14.3 | -14.3 | 3.8 | 0.18 | 14 | 0.05 | 2450 | 3100 | XXX |
| 43 | 10 | 123.7 | -4.5 | -11.9 | 3.9 | 0.18 | 7.5 | 0.09 | NA | 1750 | XXX |
| 40 | 11 | 2.6 | -11.5 | -11.5 | 1.8 | 0.38 | 3.3 | 0.21 | 2370 | 4050 | XXX |
| 35 | 23 | 44.7 | -1.8 | -1.8 | 5.9 | 0.12 | 39.1 | -0.02 | 835 | NA | XX |
| 18 | 12 | 27.5 | 1.5 | 1.5 | 2.4 | 0.29 | 6 | 0.12 | 1250 | 993 | XXX |
| 11 | 13 | 83.5 | 3 | 3 | 2.3 | 0.3 | 27.8 | 0.02 | 2510 | NA | XXX |
| 12 | 24 | 43.5 | 6.4 | 6.4 | 1.6 | 0.44 | 2.7 | 0.26 | 886 | NA | XX |
| 22 | 25 | 17 | 8.8 | 8.8 | 2.9 | 0.24 | 4.8 | 0.15 | 768 | 1820 | XX |
| 38 | 26 | 65.7 | 9.1 | 9.1 | 2.4 | 0.29 | 4.4 | 0.16 | 344 | 628 | XX |
| 33 | 14 | 9.9 | 13.1 | 13.1 | 3.7 | 0.19 | 3.7 | 0.19 | 1340 | 1090 | XXX |
| 39 | 27 | 6.6 | 24.2 | 24.2 | 2.2 | 0.09 | 5.9 | 0.12 | 367 | NA | X |
| 46 | 15 | 137.7 | 25 | 25 | 4.6 | 0.15 | 2.8 | 0.25 | 2270 | NA | XXX |
| 8 | 28 | 33.6 | 25.3 | 25.3 | 5.2 | 0.13 | 2.8 | 0.25 | 602 | 921 | X |
| 5 | 18 | 45.4 | 29.3 | 29.3 | 1.6 | 0.44 | 3.2 | 0.22 | 2054 | 1625 | XX |
| 37 | 19 | 83.7 | 43.1 | 43.1 | 1.7 | 0.41 | 2 | 0.34 | 1240 | 1300 | XX |
| 30 | 20 | 234.5 | 45.5 | 45.5 | 1.9 | 0.36 | 1.7 | 0.41 | 1740 | NA | XX |
| 29 | 21 | 83.1 | 92.8 | 92.8 | 1.6 | 0.43 | 1 | 0.66 | 3060 | 3530 | XX |

<25% PSA chg at 4 weeks · Pre-PSADT >6 months · negative PSADTs reported as 100 months · substituted for week 4 trough level <1200ng trough level

FIG. 1

TREATMENT OF PROSTATE CANCER USING HEDGEHOG PATHWAY INHIBITORS

CROSS-REFERENCE TO RELATED APPLICATIONS

The present application is a continuation of U.S. application Ser. No. 15/420,283, filed Jan. 31, 2017, which is a continuation of U.S. application Ser. No. 14/947,345, filed Nov. 20, 2015, now abandoned, which is a continuation of U.S. application Ser. No. 14/173,588, filed Feb. 5, 2014, now U.S. Pat. No. 9,192,609, which claims the benefit of U.S. Provisional Application Ser. No. 61/831,823, filed Jun. 6, 2013 and U.S. Provisional Application Ser. No. 61/813,122, filed Apr. 17, 2013, which are hereby incorporated by reference herein in their entirety, including any figures, tables, or drawings.

BACKGROUND OF INVENTION

Inhibitors of the Hedgehog (Hh) molecular signaling pathway (HhP) have emerged in recent years as a promising new class of potential therapeutics for cancer treatment. Numerous drug discovery efforts have resulted in the identification of a wide variety of small molecules that target different members of this pathway, including Smoothened (Smo), Sonic hedgehog protein (Shh), and Glioma-Associated Oncogene Homolog I, II, and III (Gli1, Gli2, and Gli3). Smo inhibitors have now entered human clinical trials, and successful proof-of-concept studies have been carried out in patients with defined genetic mutations in the Hh pathway. In fact, the first Smo inhibitor was approved by the FDA in early 2012 for use in treatment of patients with advanced basal cell carcinoma (vismodegib, marketed as ERIVEDGE™ from Roche/Genentech), validating the commercial validity of using drugs to modulate this pathway.

Activation of the (HhP) has been implicated in the development of cancers in various organs, including brain, lung, mammary gland, prostate, and skin. Basal cell carcinoma, the most common form of cancerous malignancy, has the closest association with hedgehog signaling. Loss-of-function mutations in Patched and activating mutations in Smo have been identified in patients with this disease (Sahebjam et al., "The Utility of Hedgehog Signaling Pathway Inhibition for Cancer," The Oncologist, 2012; 17:1090-1099).

As an antifungal, the mechanism of action of itraconazole is the same as the other azole antifungals, inhibiting the fungal-mediated synthesis of ergosterol. However, itraconazole has been discovered to have anti-cancer properties. Itraconazole inhibits angiogenesis and Hh signaling and delays tumor growth in murine prostate cancer xenograft models. Itraconazole appears to act on the essential Hh pathway component Smo in a mode that is different than the drug vismodegib, by preventing the ciliary accumulation of Smo normally caused by Hh stimulation and has a much shorter half-life, which may be the reason it has less side effects than vismodegib.

Prostate cancer rates are higher and prognoses are poorer in developed countries than in the rest of the world. Prostate cancer is the ninth-most-common cancer in the world, but is the number-one non-skin cancer in men from the United States. Prostate cancer affects a large percent of American men, sometimes resulting in death. In patients who undergo treatment of prostate cancer, the most important clinical prognostic indicators of disease outcome are stage, pre-therapy prostate-specific antigen (PSA) level, and Gleason score. In general, the higher the grade and the stage of prostate cancer, the poorer the prognosis. Nomograms can also be used to calculate the estimated risk of the individual patient. Some but not all prostate cancers appear to have an up-regulation of the Hh molecular pathway (U.S. Patent Application Publication No. 20120083419, Altaba et al. "Method and Compositions for Inhibiting Tumorigenesis", which is incorporated herein by reference in its entirety).

It would be advantageous to have available a prognostic tool or biomarker with proven ability to identify and distinguish, as early as possible, those cancer patients who are likely to respond to HhP inhibitor treatment from those patients that are not, so that HhP inhibitor treatments can be provided to those patients for which an HhP inhibitor will be effective and alternative treatment modalities can be provided to those for which an HhP inhibitor will be ineffective or less effective than other available treatments.

BRIEF SUMMARY OF THE INVENTION

The present invention concerns methods for treating proliferation disorders, such as prostate cancer, basal cell carcinoma, lung cancer, and other cancers, with a Hedgehog pathway (HhP) inhibitor, and methods for monitoring subjects undergoing such treatments based on biomarkers and other criteria predictive of efficacy.

Some aspects of the invention concern methods for prognosticating an outcome of prostate cancer treatment with HhP inhibitor therapy, and for determining the efficacy of HhP inhibitor therapy, based on post-therapy prostate-specific antigen. Unlike the majority of prostate cancer drugs, which target androgens in order to lower testosterone levels, itraconazole's effect is androgen-independent.

A non-comparative, randomized, phase II study was conducted evaluating the antitumor efficacy of two doses of oral itraconazole in men with metastatic prostate cancer. Based on the analysis described in FIGS. 1-3, an increase in PSA post-treatment was identified as a marker for responders to itraconazole therapy. The inventors identified patients who exhibited a PSA increase of <25% at 4 weeks post-treatment with itraconazole as those patients who were the best responders to high-dose itraconazole therapy as far as PSA progression free survival (PPFS) and Progression Free Survival (PFS). Patients who were able to achieve plasma levels of HhP inhibitor (e.g., itraconazole) of >1000 ng/ml at 4 weeks, along with the above-mentioned <25% PSA increase, are a target subpopulation of patients who can be pre-selected for treatment with HhP inhibitors as an enrichment strategy for clinical testing with these agents in prostate cancer patients (FIG. 1). Retrospective analysis showed that 14 of 15 high risk patients (PSA doubling times of less than 6 months) on high-dose itraconazole demonstrated PSA increases of <25% at 4 weeks which translated into significant improvements in Progression Free Survival (FIG. 2). K-M Analysis based on PSA change at 4 weeks is shown in FIG. 3. Surprisingly, this effect was observed to continue beyond the 4 week time point.

PSA levels are known to be a function of androgen activity. As androgen activity increases (such as results from supplemental testosterone therapy), the higher the PSA. As androgen activity decreases (such as results from androgen deprivation therapy, anti-androgens, etc.), the lower the PSA. Because itraconazole has no effect on androgen synthesis, plasma levels or receptor activity, it was not expected that itraconazole would have any significant effect on PSA. Additionally, since itraconazole is an inhibitor of the HhP and is not significantly cytotoxic (unlike chemotherapy), there was no reason to expect any significant effect on PSA because itraconazole does not kill the cancer cells (and, hence, eliminating their contribution to PSA levels). Dendreon's PROVENGE® cancer vaccine is an example of anti-prostate cancer agent that has no effect on PSA or PFS but provides improved overall survival. In contrast, in the case of itraconazole, the inventors discovered unexpectedly that a reduction in PSA rise of </=25% is associated with a significant PFS and PSA-PFS. Furthermore, since HhP upregulation cannot be easily measured in men who have undergone radical prostatectomy with no radiographic evidence of recurrence or metastatic disease but who have rising PSA, the ability to use the PSA rise of <1=25% provides a way to determine sensitivity to a HhP inhibitor in a situation where the clinicians cannot be sure that the PSA is associated with upregulation of the HhP. Thus, unless the HhP is upregulated, it appears that an HhP inhibitor is not therapeutic, meaning that normal activity of the HhP in a PSA cell is not going to render it susceptible to HhP inhibitor treatment.

Surprisingly, the inventors found that the plasma concentrations of itraconazole required to show a clinical benefit in humans with cancer are significantly greater than the typical levels for antifungal efficacy. Shi W. et al. reported that antifungal potency is determined by structure unrelated to the inhibition of the HhP (Shi W. et al., "Itraconazole Side Chain Analogues: Structure-Activity Relationship Studies for Inhibition of Endothelial Cell Proliferation, Vascular Endothelial Cell Growth Factor Receptor 2 (VEGFR2) Glycosylation, and Hedgehog Signaling," *J. Med. Chem.*, 2011, 54:7363-7374, which is incorporated herein by reference in its entirety); thus, the use of higher doses of HhP inhibitors such as itraconazole to treat systemic fungal infections in cancer patients did not support or suggest that the dose required to treat cancer was in the range of high dose antifungal therapy.

Furthermore, the determination of the minimum trough level to achieve an effect on proliferation disorders such as cancer was not predicted from the in vitro studies by Shi W. et al because of these considerations: (i) itraconazole has multiple anti-cancer properties, including anti-angiogenic, mTOR (mammalian target of rapamycin) inhibition, and anti-hedgehog; therefore, the in vitro studies of the HhP or anti-angiogenic effects, for example, were not sufficient to predict dosing or plasma levels; (ii) after a number of days of dosing, sufficient to achieve a steady state, the tissue concentration of itraconazole is known to be a multiple of plasma levels; and (iii) unlike the antifungal effects, the major metabolite of itraconazole (hydroxy-itraconazole) is not equipotent as a HhP inhibitor but it does seem to have significant effects making extrapolation to in vivo plasma levels that are effective in cancer impossible to predict.

One aspect of the invention concerns a method for treating a proliferation disorder in a subject, such as prostate cancer, basal cell carcinoma, lung cancer, and other cancers, comprising orally administering a composition comprising a Hedgehog pathway (HhP) inhibitor to the subject, wherein the composition is orally administered in an effective amount to achieve a plasma trough level of at least about 1,000 ng/mL of the HhP inhibitor. Optionally, the method of treatment includes monitoring the proliferation disorder in the subject to determine whether there has been a clinical response to HhP inhibitor treatment.

Another aspect of the invention concerns a method of prognosticating an outcome of prostate cancer treatment with a Hedgehog pathway (HhP) inhibitor therapy in a subject, comprising comparing the level of prostate-specific antigen (PSA) in a sample obtained from the subject following HhP inhibitor therapy with a reference level of PSA, wherein the level of PSA in the sample compared to the reference level of PSA is prognostic for an outcome of treatment with the HhP inhibitor.

Another aspect of the invention concerns a method of determining the efficacy of Hedgehog pathway (HhP) inhibitor therapy for prostate cancer in a human subject, comprising measuring prostate-specific antigen (PSA) level in a sample obtained from the subject following initiation of HhP inhibitor therapy, wherein a measured PSA level compared to a first reference PSA level at initiation of HhP inhibitor therapy is indicative of efficacy, and wherein a measured PSA level compared to a second reference PSA level is indicative of a lack of efficacy.

Another aspect of the invention concerns a method for treating prostate cancer in a subject, comprising administering Hedgehog pathway (HhP) inhibitor therapy to the subject; and carrying out a method of the invention (i.e., a method of prognosticating an outcome of prostate cancer treatment with a HhP inhibitor therapy, or a method of determining the efficacy of HhP inhibitor therapy).

BRIEF DESCRIPTION OF DRAWINGS

FIG. 1: PSA increase at four weeks as a screening tool for responders to itraconazole therapy. The data reflect analysis of parameters that are indicative of successful administration of itraconazole therapy to prostate cancer patients based on PSA response. The inventors identified patients who exhibited a PSA increase of <25% at 4 weeks post-treatment with itraconazole as those patients who were the best responders to high-dose itraconazole therapy as far as PSA progression free survival (PPFS) and Progression Free Survival (PFS). Patients who were able to achieve plasma levels of itraconazole of >1000 ng/ml at 4 weeks, along with the above-mentioned <25% PSA increase, are a target subpopulation of patients who can be pre-selected for treatment with itraconazole as an enrichment strategy for clinical testing of itraconazole in prostate cancer patients.

DETAILED DESCRIPTION OF THE INVENTION

Figure 2:
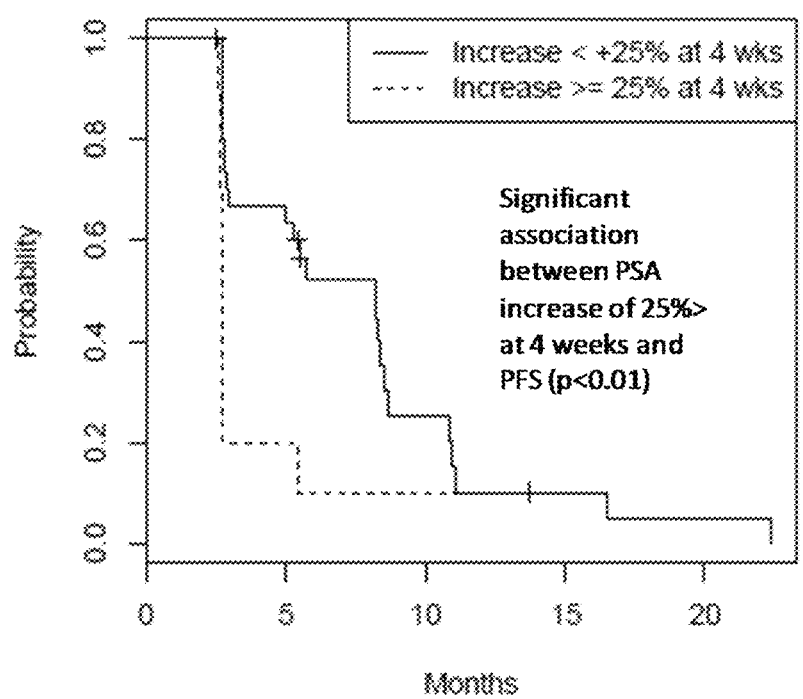
FIG. 2: In this retrospective analysis, 14 of 15 high risk patients (PSA doubling times of less than 6 months) on high-dose itraconazole demonstrated PSA increases of <25% at 4 weeks which translated into significant improvements in Progression Free Survival.
Figure 3:
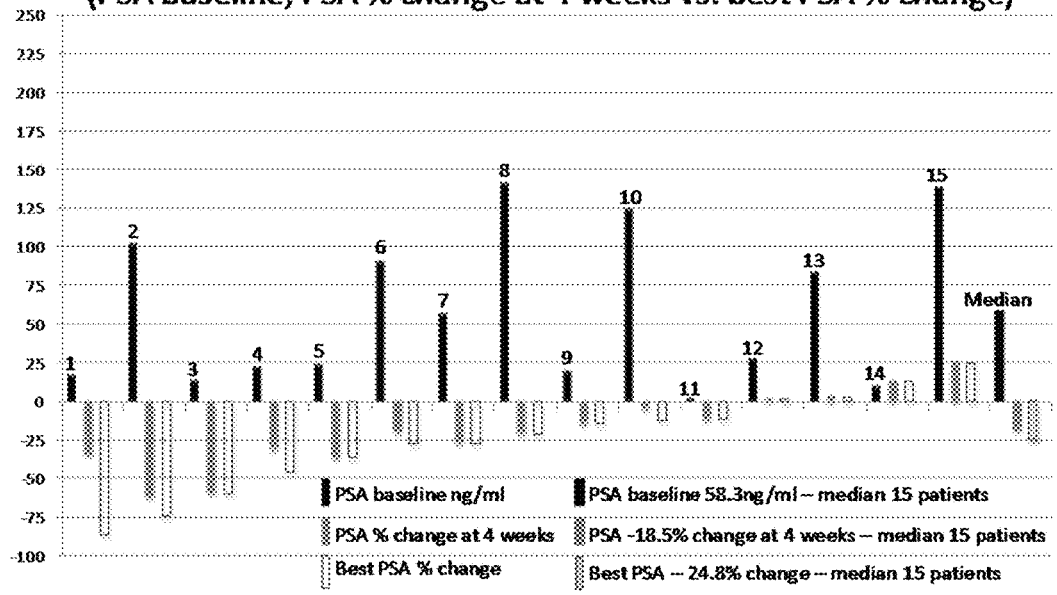
FIG. 3: K-M Analysis based on PSA change at 4 weeks. PFS (radiographic) in high-dose group.

One aspect of the invention concerns a method for treating a proliferation disorder in a subject, comprising orally administering a composition comprising a Hedgehog pathway (HhP) inhibitor to the subject, wherein the composition is orally administered in an effective amount to achieve a plasma trough level of at least about 1,000 ng/mL of the HhP inhibitor.

In some embodiments, the composition is administered in an effective amount to achieve a plasma trough level of at least 1,000 ng/mL of the HhP inhibitor. In some embodiments, the composition is administered in an effective amount to achieve a plasma trough level of at least about 1,000 ng/mL of the HhP inhibitor after about 4 weeks of initiation of treatment with the HhP inhibitor. In some embodiments, the composition is administered in an effective amount to achieve a plasma trough level of at least about 1,000 ng/mL of the HhP inhibitor within about 2 weeks after initiation of treatment, and to maintain the plasma trough level of at least about 1,000 ng/mL of the HhP inhibitor for the duration of the treatment.

Any inhibitor of the HhP may be used. In some embodiments, the HhP inhibitor targets the Smoothened (Smo) protein of the HhP pathway, acting on Smo, for example, by binding to it. In some embodiments, the HhP inhibitor is cyclopamine-competitive. In some embodiments, the HhP inhibitor comprises itraconazole, or a pharmaceutically acceptable salt, prodrug, or active metabolite thereof. In some embodiments, the HhP inhibitor is a purified stereoisomer of itraconazole (non-racemic mixture), or an itraconazole analogue in which the sec-butyl side chain has been replaced with one or more moieties, relative to itraconazole. In some embodiments, the HhP inhibitor is cyclopamine-competitive. In some embodiments, the HhP inhibitor is non-cyclopamine-competitive. In some embodiments, the HhP inhibitor is cyclopamine-competitive and the proliferation disorder is prostate cancer, basal cell carcinoma, or lung cancer.

The HhP inhibitor may be formulated for the desired delivery route. Furthermore, achieving the desired level of HhP inhibitor can be enhanced by the use of formulations with greater bioavailability. For example, the HhP inhibitor may be administered in a composition such as SUBA® formulation of itraconazole, or a pharmaceutically acceptable salt, prodrug, or active metabolite thereof. In some embodiments, an HhP inhibitor such as itraconazole, or a pharmaceutically acceptable salt, prodrug, stereoisomer, or active metabolite thereof, is administered in a SUBA® formulation at a dose in the range of 100 mg to 600 mg per day. In some embodiments, 150 mg of an HhP inhibitor such as itraconazole, or a pharmaceutically acceptable salt, prodrug, stereoisomer, or active metabolite thereof, is administered in a SUBA® formulation two or more times per day. In some embodiments, 200 mg of an HhP inhibitor such as itraconazole, or a pharmaceutically acceptable salt, prodrug, stereoisomer, or active metabolite thereof, is administered in a SUBA® formulation two or more times per day.

In some embodiments, the HhP inhibitor therapy comprises oral administration of a capsule, tablet, or suspended powder (liquid suspension), or liquid solution of 50 mg of the itraconazole, or a pharmaceutically acceptable salt, prodrug, stereoisomer, or active metabolite thereof, twice per day. In some embodiments, the SUBA® formulation is a SUBA-CAP™ formulation.

Optionally, the treatment method further comprises measuring the plasma level of the HhP inhibitor, or a metabolite thereof, in the subject one or more times. In some embodiments, the measuring is carried out one or more times about 4 weeks after initiation of treatment with the HhP inhibitor.

In some embodiments, the method includes measuring the plasma level of the HhP inhibitor, or a metabolite thereof, one or more times in a period of time from about 4 weeks to about 12 weeks. Optionally, the method further comprises increasing a subsequent dose of the HhP inhibitor if the plasma trough level of at least about 1,000 ng/mL of the HhP inhibitor is not maintained. Optionally, the method may further comprise reducing a subsequent dose of an HhP inhibitor if the plasma trough level at about 4 weeks is at least 1000 ng/mL and the subject is experiencing one or more side effects.

Various dosing regimens may be utilized. In some embodiments, the HhP inhibitor is administered at least once daily. In some embodiments, the HhP inhibitor is administered at least twice daily. In some embodiments, the duration of treatment with the HhP inhibitor is in the range of about 4 weeks to about 24 weeks. In some embodiments, once achieved, a plasma trough level of at least about 1,000 ng/mL of HhP inhibitor is maintained throughout the therapy.

In some embodiments, the proliferation disorder is a cancer, such as prostate cancer, basal cell carcinoma, lung cancer, or other cancer.

In some embodiments, the proliferation disorder is prostate cancer and the method further comprises comparing the level of prostate-specific antigen (PSA) in a sample obtained from the subject following administration of the HhP inhibitor with a reference level of PSA, wherein the level of PSA in the sample compared to the reference level of PSA is prognostic for an outcome of treatment with the HhP inhibitor. In some embodiments, a PSA level increase of less than about 25% relative to the PSA level at initiation of HhP inhibitor treatment is indicative of efficacy and a PSA level increase of about 25% or greater is indicative of a lack of efficacy. In some embodiments, the subject has a PSA level increase of less than about 25% after about 4 weeks on HhP inhibitor treatment relative to the PSA level at initiation of HhP inhibitor treatment.

In some embodiments, the sample is obtained from the subject within 4 to 12 weeks after initiation of HhP inhibitor therapy.

In some embodiments, the method further comprises obtaining the sample from the subject after said administering.

In the case of prostate cancer, in some embodiments, the method further comprises maintaining HhP inhibitor therapy if the measured level of PSA is indicative of efficacy.

In the case of prostate cancer, in some embodiments, the method further comprises ceasing treatment with the HhP inhibitor if the measured level of PSA is indicative of a lack of efficacy. Optionally, the method further comprises administering a treatment for the prostate cancer other than an HhP inhibitor. In some embodiments, the treatment comprises one or more from among radiation therapy, hormone therapy, chemotherapy, immunotherapy, surgery, cryosurgery, high-intensity focused ultrasound, and proton beam radiation therapy.

In the case of prostate cancer, in some embodiments, the method further comprises increasing the dose of the HhP inhibitor and/or frequency of dose of the HhP inhibitor if the measured level of PSA is indicative of a lack of efficacy.

In the case of prostate cancer, in some embodiments, the method further comprises decreasing the dose of the HhP inhibitor and/or frequency of dose of the HhP inhibitor if the measured level of PSA is indicative of efficacy but the subject is experiencing one or more adverse effects.

In the case of prostate cancer, in some embodiments, the PSA level measured is the level of total PSA (free (unbound) PSA and bound PSA). In some embodiments, the PSA level measured is PSA doubling time.

In the case of prostate cancer, in some embodiments, the PSA protein level is measured, using methods such as radioimmunoassay (MA), immunoradiometric assay (IRMA), enzyme-linked immunosorbent assay (ELISA), dot blot, slot blot, enzyme-linked immunosorbent spot (ELISPOT) assay, Western blot, peptide microarray, surface plasmon resonance, fluorescence resonance energy transfer, bioluminescence resonance energy transfer, fluorescence quenching fluorescence, fluorescence polarization, mass spectrometry (MS), high-performance liquid chromatography (HPLC), high-performance liquid chromatography/mass spectrometry (HPLC/MS), high-performance liquid chromatography/mass spectrometry/mass spectrometry (HPLC/MS/MS), capillary electrophoresis, rod-gel electrophoresis, or slab-gel electrophoresis.

In some embodiments, the PSA DNA or mRNA level is measured using methods such as Northern blot, Southern blot, nucleic acid microarray, polymerase chain reaction (PCR), real time-PCR (RT-PCR), nucleic acid sequence based amplification assay (NASBA), or transcription mediated amplification (TMA).

In the case of prostate cancer, in some embodiments, the PSA activity level is measured.

Optionally, in the case of prostate cancer, the treatment method further comprises monitoring the PSA level in the subject, comprising comparing the PSA level in multiple samples with the reference level of PSA, wherein the samples are obtained from the subject over time, following HhP inhibitor treatment.

In some embodiments, the method of treatment further comprises obtaining the sample from the subject. In some embodiments, the sample is a serum sample.

The method of treatment may include monitoring the proliferation disorder in the subject to determine whether there has been a clinical response to HhP inhibitor treatment. In some embodiments, the method further comprises monitoring the proliferation disorder in the subject, wherein a lack of clinical response in the proliferation disorder to the treatment is indicative that the plasma trough level of the HhP inhibitor should be increased further above about 1000 ng/mL, and wherein the occurrence of a clinical response and a plasma trough level of the HhP inhibitor substantially higher than about 1000 ng/mL indicates that one or more subsequent doses of the HhP inhibitor can be reduced. In some embodiments, the method further comprises monitoring the proliferation disorder in the subject, wherein a lack of clinical response in the proliferation disorder to the treatment, after about four weeks of said administering, is indicative of a need to increase the dose, and/or frequency of the dose, of the HhP inhibitor. Optionally, the method further comprises subsequently administering the HhP inhibitor to the subject at the increased dose and/or frequency. In some embodiments, the method further comprises monitoring the proliferation disorder in the subject, wherein the occurrence of a clinical response in the proliferation disorder to the treatment, after about four weeks of said administering, is indicative of a need to decrease the dose, and/or frequency of the dose, of the HhP inhibitor. Optionally, the method further comprises subsequently administering the HhP inhibitor to the subject at a decreased dose and/or frequency.

In some embodiments, the monitoring comprises visual inspection, palpation, imaging, assaying the presence, level, or activity of one or more biomarkers associated with the proliferation disorder in a sample obtained from the subject, or a combination of two or more of the foregoing. In some embodiments, the monitoring comprises monitoring at least one of the following parameters: tumor size, rate of change in tumor size, hedgehog levels or signaling, appearance of new tumors, rate of appearance of new tumors, change in symptom of the proliferation disorder, appearance of new symptom associated with the proliferation disorder, quality of life (e.g., amount of pain associated with the proliferation disorder), or a combination of two or more of the foregoing.

As indicated above, the inventors found that the plasma concentrations of itraconazole required to show a clinical benefit in humans with cancer are significantly greater than the typical levels for antifungal activity. In particular, the minimum plasma trough level after 4 weeks of therapy required to have a clinically significant effect was at least 1000 ng/ml. Achieving these levels of itraconazole is enhanced by the use of formulations with greater bioavailability such as SUBA-CAP™ formulation. Nevertheless, there can be side-effects peculiar to such high doses such as hypertension, peripheral edema, and hypokalemia, which seem to be a result of an increased production of mineralocorticoid. These side effects associated with these high doses of itraconazole can be effectively managed by giving a selective mineralocorticoid antagonist, such as eplerenone. Accordingly, in some embodiments, the method further comprises administering eplerenone or other mineralocorticoid inhibitor. In some embodiments, the subject is suffering from an adverse effect selected from hypertension, peripheral edema, and hypokalemia, and wherein the mineralocorticoid inhibitor is administered in an amount effective to treat the adverse effect.

In some embodiments, the subject has a fungal infection. In other embodiments, the subject does not have a fungal infection.

In some embodiments, the subject has a fungal infection selected from Blastomycosis, Histoplasmosis, Candidiasis, and Aspergillosis. In other embodiments, the subject does not have a fungal infection selected from among Blastomycosis, Histoplasmosis, Candidiasis, and Aspergillosis.

In some embodiments, the subject has received no prior chemotherapy to treat the proliferation disorder.

In some embodiments, the subject is administered no steroid during the duration of the treatment.

In some embodiments, the subject is administered no agent that interacts with CYP3A4 during the duration of the treatment.

The present invention also concerns methods for prognosticating an outcome of prostate cancer treatment with a Hedgehog pathway (HhP) inhibitor therapy, and for determining the efficacy of HhP inhibitor therapy, based on post-therapy prostate-specific antigen.

One aspect of the invention concerns a method of prognosticating an outcome of prostate cancer treatment with a Hedgehog pathway (HhP) inhibitor therapy in a subject, comprising comparing the level of prostate-specific antigen (PSA) in a sample obtained from the subject following HhP inhibitor therapy with a reference level (predetermined level) of PSA, wherein the level of PSA in the sample compared to the reference level of PSA is prognostic for an outcome of treatment with the HhP inhibitor. In some embodiments, the reference level is the PSA level in the subject at initiation of HhP inhibitor therapy. In some embodiments, the method comprises monitoring the PSA level in the subject, comprising comparing the PSA level in multiple samples with the reference level of PSA, wherein the samples are obtained from the subject over time, following HhP inhibitor therapy.

Another aspect of the invention concerns a method of determining the efficacy of Hedgehog pathway (HhP) inhibitor therapy for prostate cancer in a human subject, comprising measuring prostate-specific antigen (PSA) level in a sample obtained from the subject following initiation of HhP inhibitor therapy, wherein a measured PSA level compared to a first reference PSA level (first predetermined level) at initiation of HhP inhibitor therapy is indicative of efficacy, and wherein a measured PSA level compared to a second reference PSA level (second predetermined level) is indicative of a lack of efficacy. In some embodiments, the method comprises monitoring the PSA level in the subject, comprising measuring the PSA level in multiple samples obtained from the subject over time, following HhP inhibitor therapy (e.g., at one or more of 4 weeks, 5 weeks, 6 weeks, 7 weeks, 8 weeks, 9 weeks, 10 weeks, 11 weeks, 12 weeks or longer following initiation of HhP therapy). In some embodiments, a sample is obtained at about 3 to 5 weeks and/or at about 11 to 13 weeks following initiation of HhP inhibitor therapy. In some embodiments, a sample is obtained at about 4 weeks and/or at about 12 weeks following initiation of HhP inhibitor therapy.

In some embodiments of the methods of the invention, a PSA level increase of less than about 25% relative to the PSA level at initiation of HhP inhibitor therapy is indicative of efficacy and a PSA level increase of about 25% or greater is indicative of a lack of efficacy.

In some embodiments of the methods of the invention, the HhP inhibitor comprises itraconazole, or a pharmaceutically acceptable salt, prodrug, stereoisomer, or active metabolite thereof. For example, the HhP inhibitor may comprise or consist of a SUBA® formulation (Mayne Pharma International Pty Ltd., e.g., the SUBACAP™ formulation) of itraconazole (see, for example, U.S. Patent Application Publication No. 20030225104 (Hayes et al., "Pharmaceutical Compositions for Poorly Soluble Drugs," issued as U.S. Pat. No. 6,881,745), which is a solid dispersion wherein itraconazole is associated with acidic molecules and the formulation allows for improved absorption. In some embodiments, the HhP inhibitor, such as a SUBA® formulation, is administered to the subject at a dose in the range of 100 mg to 600 mg per day.

In some embodiments, the HhP inhibitor is administered intravenously or locally (e.g., by direct injection) to a prostate cancer lesion or tumor. In some embodiments, the HhP inhibitor is administered orally, e.g., in capsule, tablet, suspended powder (liquid suspension), or liquid solution form. In some embodiments, the HhP inhibitor is orally administered (e.g., in capsule, tablet, suspended powder (liquid suspension), or liquid solution form) in an amount comprising or consisting of about 25 mg to about 100 mg per dose twice a day. In some embodiments, the HhP inhibitor is orally administered (e.g., in capsule, tablet, suspended powder (liquid suspension), or liquid solution form) in an amount comprising or consisting of 50 mg per dose twice a day.

In some embodiments of the methods of the invention, the sample is obtained from the subject within 4 to 6 weeks after initiation of HhP inhibitor therapy.

In some embodiments of the methods of the invention, the method further comprises administering the HhP inhibitor to the subject, and obtaining the sample from the subject after said administering.

In some embodiments of the methods of the invention, the method further comprises maintaining HhP inhibitor therapy if the measured level of PSA is indicative of efficacy.

In some embodiments of the methods of the invention, the method further comprises withholding HhP inhibitor therapy if the measured level of PSA is indicative of a lack of efficacy. Withholding HhP inhibitor therapy may include watchful waiting or active surveillance. Optionally, the method further comprises administering one or more treatments for the prostate cancer other than an HhP inhibitor. Examples of prostate cancer treatments include, but are not limited to, radiation therapy, hormone therapy, chemotherapy, immunotherapy, surgery (surgical excision/removal of cancerous tissue, e.g., open or laparoscopic prostatectomy), cryosurgery, high-intensity focused ultrasound, and proton beam radiation therapy.

It should be understood that indications of HhP inhibitor therapy efficacy or lack of efficacy can be specific to the dose and/or frequency of the dose administered. In this way, the invention provides a method for determining a dose of HhP inhibitor suitable for administration to a subject for treatment of prostate cancer. This involves carrying out a method of prognosticating an outcome of prostate cancer treatment or determining efficacy of an HhP inhibitor therapy as described herein, and determining an effective dose of HhP inhibitor based on the comparison of PSA level measured in a sample obtained following a dosage level and/or dose frequency change to a reference PSA level.

For example, it is possible to administer a dose of HhP inhibitor at one level and/or one frequency and not observe a PSA response, but administer a dose at a different (greater) level and/or frequency and observe a PSA response. Therefore, the dose level and/or frequency of dosing may affect whether an HhP inhibitor works or does not work. Consequently, if a lack of efficacy is indicated based on PSA level at one dose and/or one frequency of the HhP inhibitor, before withholding the HhP therapy and/or administering an alternative (non-HhP inhibitor) treatment for the prostate cancer, it may be desirable to modulate (e.g., increase) the dosage and/or frequency of the HhP inhibitor and, optionally, obtain one or more subsequent samples and measure the PSA level in the sample(s) and compare the measured level to the reference level to make another determination of prognosis or efficacy/non-efficacy at the different dosage and/or frequency. Accordingly, in some embodiments of the methods of the invention, the method further comprises increasing the dose of the HhP inhibitor and/or frequency of dose of the HhP inhibitor if the measured level of PSA is indicative of a lack of efficacy. This may be repeated one or more times until efficacy of that dosage regimen is indicated based on measured level of PSA relative to the reference level (e.g., as a dose titration using reference PSA level as a guide). Optionally, at any point in the process, the HhP inhibitor can be withheld and, optionally, an alternative (non-HhP inhibitor) treatment administered to the subject.

Alternatively, if a subject does achieve a PSA level indicative of efficacy at one dose level and/or frequency, but the subject experiences one or more side effects, then the dose level and/or frequency of dose may be subsequently decreased. One or more samples may then be obtained, PSA level measured, and compared to a reference level to ensure that the measured PSA level at the decreased dose and/or frequency remains indicative of efficacy. Again, the PSA level may be used as a biomarker or guide for optimal dosing of subsequent administrations with the HhP inhibitor. Accordingly, in some embodiments of the methods of the invention, the method further comprises decreasing the dose of the HhP inhibitor and/or frequency of dose of the HhP inhibitor if the measured level of PSA is indicative of efficacy but the subject is experiencing one or more side effects. This may be repeated one or more times until the side effects are reduced or eliminated without compromising efficacy of that dosage regimen based on PSA level. Optionally, at any point in the process, the HhP inhibitor can be withheld and, optionally, an alternative (non-HhP inhibitor) treatment administered to the subject. This may be desirable if the side effects are not manageable without compromising efficacy.

As indicated above, an aspect of the invention is a method for determining a dose of HhP inhibitor suitable for administration to a subject for treatment of prostate cancer, comprising measuring a PSA level in a sample obtained from the subject following HhP inhibitor administration (e.g., at about 4 weeks and/or about 12 weeks after initiation of HhP inhibitor therapy); and determining an effective dose of the HhP inhibitor based on comparison of the measured PSA level to a reference level of PSA (e.g., a PSA level increase of less than about 25% relative to the PSA level at initiation of HhP inhibitor therapy). By way of example, 50 mg of an HhP inhibitor may be administered incrementally to a subject to establish efficacy by increasing the dose (adjusting the amount and/or frequency of subsequent doses upward) if the subject does not respond or decreasing the dose (adjusting the amount and/or frequency downward) if it is too toxic. In the case of a SUBA® formulation of an azole antifungal drug, for example, such as a SUBACAP™ formulation, a dose may be titrated up or down such that the dose is within the range of 100 mg to 600 mg of SUBA™ formulation per day usually in divided doses administered twice daily. The high end of the range may be used for example to obtain rapid trough levels on day-one or day-two and then the dose may be reduced (in amount and/or frequency), or for some prostate cancers, it may be determined that a more potent dose is required.

In some embodiments of the methods of the invention, the PSA level is the level of total PSA (free (unbound) PSA and bound PSA). In some embodiments of the methods of the invention, the PSA level is PSA doubling time.

In the methods of the invention, the determined PSA level may represent the amount of PSA protein, the amount of nucleic acid (DNA or mRNA) encoding PSA, or the amount of PSA activity. In some embodiments, the PSA protein level is measured by radioimmunoassay (MA), immunoradiometric assay (IRMA), enzyme-linked immunosorbent assay (ELISA), dot blot, slot blot, enzyme-linked immunosorbent spot (ELISPOT) assay, Western blot, peptide microarray, surface plasmon resonance, fluorescence resonance energy transfer, bioluminescence resonance energy transfer, fluorescence quenching fluorescence, fluorescence polarization, mass spectrometry (MS), high-performance liquid chromatography (HPLC), high-performance liquid chromatography/mass spectrometry (HPLC/MS), high-performance liquid chromatography/mass spectrometry/mass spectrometry (HPLC/MS/MS), capillary electrophoresis, rod-gel electrophoresis, or slab-gel electrophoresis. In some embodiments, the PSA mRNA level is measured by Northern blot, Southern blot, nucleic acid microarray, polymerase chain reaction (PCR), real time-PCR (RT-PCR), nucleic acid sequence based amplification assay (NASBA), or transcription mediated amplification (TMA).

The sample obtained from the subject may be potentially any sample harboring PSA protein or nucleic acids. The sample may be processed before or after the PSA biomarker is measured. In some embodiments of the methods of the invention, the sample is a serum sample.

The methods of the invention may further comprise obtaining the sample from the subject, such as by withdrawing blood or by tissue biopsy.

The methods of the invention may further comprise identifying the subject as having prostate cancer (e.g., based on one or more biomarkers, signs, symptoms, biopsy, etc.) before initiating HhP therapy.

In some embodiments, prior to initiation of treatment with the HhP inhibitor, the subject has undergone treatment for the prostate cancer with a non-HhP inhibitor. For example, the HhP inhibitor may be administered as a second line, third line, or fourth line therapy.

There are other tools available to help predict outcomes in prostate cancer treatment, such as pathologic stage and recurrence after surgery or radiation therapy. Most combine stage, grade, and PSA level, and some also add the number or percent of biopsy cores positive, age, and/or other information. The methods of the invention may be used in addition to, or as an alternative to, methods for prognosticating prostate cancer, such as D'Amico classification, the Partin tables, the Kattan nomograms, and the UCSF Cancer of the Prostate Risk Assessment (CAPRA) score.

Another aspect of the invention concerns a method for treating prostate cancer in a subject, comprising administering Hedgehog pathway (HhP) inhibitor therapy to the subject; and carrying out a method of the invention (i.e., a method of prognosticating an outcome of prostate cancer treatment with a HhP inhibitor therapy, or a method of determining the efficacy of HhP inhibitor therapy).

Patient Selection

Optionally, subjects in need of treatment (or further treatment) of a proliferation disorder such as prostate cancer, basal cell carcinoma, lung cancer, or other cancer, may be selected as an individual particularly suitable for treatment with an HhP inhibitor, based on Hh levels or signaling, which may be assessed directly or indirectly by measuring a biomarker (an HhP biomarker) that represents the HhP signal itself or a modulator of the HhP signal (inducer or inhibitor). If the biomarker is an inhibitor of the HhP signal, and the level of the inhibitor is below normal, an assumption may be made that the HhP signal is elevated above normal. Likewise, if the biomarker is an inhibitor of the HhP signal, and the level of the inhibitor is above normal, an assumption may be made that the HhP signal is reduced below normal. If the biomarker is an inducer of the HhP signal, and the level of the inducer is below normal, an assumption may be made that the HhP signal is reduced below normal. Likewise, if the biomarker is an inducer of the HhP signal, and the level of the biomarker is above normal, an assumption may be made that the HhP signal is elevated above normal. Optionally, the accuracy of the aforementioned assumptions may be confirmed by measuring HhP signaling directly or by measuring other additional HhP biomarkers.

Hh levels or signaling may be assessed by measuring an HhP protein, or a nucleic acid encoding an HhP protein such as an HhP ligand that activates the pathway and/or an upstream or downstream component(s) of the HhP, e.g., a receptor, activator or inhibitor of hedgehog. Ligands of the mammalian HhP include Sonic hedgehog (SHH), desert hedgehog (DHH), and Indian hedgehog (DHH). Activation of the HhP leads to nuclear translocation of glioma-associated oncogene homolog (Gli) transcription factors, and the levels of these transcription factors may be assessed as well (e.g., Gli1, Gli2, Gli3, or a combination or two or more of the foregoing).

Any of the aforementioned biomarkers can be detected in a sample obtained from the subject such as blood, urine, circulating tumor cells, a tumor biopsy, or a bone marrow biopsy. These biomarkers can also be detected by systemic administration of a labeled form of an antibody to a biomarker followed by imaging with an appropriate imaging modality. The measured level in the sample may be compared to a reference level such as a normal level representative of constitutive expression of the biomarker or a normal level of HhP signaling, or a level that was previously measured in a sample obtained from the subject (e.g., in a sample obtained from the subject at an earlier time in the treatment regimen or before the subject developed the proliferation disorder). If the HhP biomarker is upregulated (elevated) relative to the reference level, then the subject can be selected for treatment with an HhP inhibitor such as itraconazole, or a pharmaceutically acceptable salt, prodrug, stereoisomer, or active metabolite thereof, and administration of the HhP inhibitor to the subject may proceed. Furthermore, as described below, the proliferation disorder may then be monitored for a clinical response by obtaining another sample from the subject, measuring the biomarker, and comparing the measured level to the level measured in the sample that was obtained previously. Multiple samples may be obtained and measurements determined and compared during the course of the treatment to monitor the proliferation disorder and clinical response to the treatment over time.

Monitoring a Proliferation Disorder

Because not every proliferation disorder may be immediately responsive to every dosage regimen with an HhP inhibitor, even in the therapeutic range of at least about 1000 ng/mL, it may be desirable to monitor the proliferation disorder in the subject for the presence or absence of a response to the HhP inhibitor treatment. The plasma trough level of at least about 1000 ng/ml ensures an empirical trial of HhP inhibitor is more likely to be effective but it may take higher levels to be effective and in some subjects no matter what the dose, the HhP inhibitor is not effective, perhaps because the HhP is not up-regulated or there are mutations that make the HhP inhibitor ineffective in blocking the up-regulation.

Accordingly, in some embodiments, the method further comprises monitoring the proliferation disorder for the presence or absence of a response to the HhP inhibitor treatment. In some embodiments, the method further comprises monitoring the proliferation disorder in the subject, wherein a lack of clinical response in the proliferation disorder to the treatment is indicative that the plasma trough level of the HhP inhibitor should be increased further above about 1000 ng/mL, and wherein the occurrence of a clinical response and a plasma trough level of the HhP inhibitor substantially higher than about 1000 ng/mL indicates that one or more subsequent doses of the HhP inhibitor can be reduced. In some embodiments, the method further comprises monitoring the proliferation disorder in the subject, wherein a lack of clinical response in the proliferation disorder to the treatment, after about four weeks of said administering, is indicative of a need to increase the dose, and/or frequency of the dose, of the HhP inhibitor. In some embodiments, the method further comprises monitoring the proliferation disorder in the subject, wherein the occurrence of a clinical response in the proliferation disorder to the treatment, after about four weeks of said administering, is indicative of a need to decrease the dose, and/or frequency of the dose, of the HhP inhibitor.

In some embodiments, the monitoring comprises visual inspection, palpation, imaging, assaying the presence, level, or activity of one or more biomarkers associated with the proliferation disorder in a sample obtained from the subject, or a combination of two or more of the foregoing, one or more times at various intervals of treatment to ascertain whether the treatment is effectively treating the proliferation disorder in the subject (causing or contributing to a clinical response in the subject). For skin cancers such a basal cell or malignant melanoma visual inspection can be with unaided eye. Visual inspection via colonoscopy may be utilized for colorectal cancers and precancerous proliferation disorders such as polyps. Bronchoscopy may be used for lung cancer. Esophagoscopy may be used for esophageal cancers and precancers (e.g., Barret's esophagus). Gastroscopy may be used for gastric cancers. Cystoscopy may be used for bladder cancers and precancerous proliferation disorders. Laparoscopy may be used for ovarian cancers and endometriosis. Biomarkers such as PSA, PCA2 antigen, and Gli (Gli1, Gli2, Gli3, or a combination of two or three Gli) may be assayed. For example, a decreased level of expression of the Gli in the sample relative to a reference level (such as a baseline) is indicative of a positive clinical response to the HhP inhibitor treatment (efficacy), and an increased level of expression of the Gli relative to a reference level (such as a baseline) is indicative of a negative clinical response or lack of clinical response to the HhP inhibitor treatment (lack of efficacy). Examples of other tumor markers are provided below.

Examples of imaging modalities that may be utilized include computed tomography (CT), magnetic resonance imaging (MM), ultrasound, x-ray, and nuclear medicine scans. Palpation may be conducted for lymph nodes, transrectal digital exam for prostatic cancers, and a pelvic exam for ovarian cancers, abdominal palpation for liver cancers (primary or metastatic).

In some embodiments, the monitoring comprises monitoring at least one of the following parameters: tumor size, rate of change in tumor size, hedgehog levels or signaling, appearance of new tumors, rate of appearance of new tumors, change in symptom of the proliferation disorder, appearance of a new symptom associated with the proliferation disorder, quality of life (e.g., amount of pain associated with the proliferation disorder), or a combination of two or more of the foregoing.

As indicated above, the method for treating a proliferation disorder may include monitoring the proliferation disorder in the subject following administration of the HhP inhibitor, wherein a lack of clinical response in the proliferation disorder to the treatment is indicative that the plasma trough level of the HhP inhibitor should be increased further above about 1,000 ng/mL, and wherein the occurrence of a clinical response and a plasma trough level of the HhP inhibitor substantially higher than about 1,000 ng/mL indicates that one or more subsequent doses of the HhP inhibitor can be reduced.

In some embodiments, the treatment method further comprises monitoring the proliferation disorder in the subject for a clinical response. In some embodiments, the clinical response is tumor response and the Response Evaluation Criteria In Solid Tumors (RECIST) may be used to define when tumors in cancer patients improve (show a "clinical response"), stay the same ("stabilize"), or worsen ("progress") during treatment. In some embodiments, a decrease in tumor size is indicative of improvement or clinical response, and an increase or no change in the size of a tumor is indicative of a lack of clinical response. The site of the tumor will depend upon the type of cancer. In basal cell carcinoma, the tumor will be in the skin. The occurrence of a clinical response to the treatment after a period of time (e.g., after about four weeks of administering the HhP inhibitor) indicates that the HhP inhibitor dose, HhP inhibitor dose frequency, and choice of HhP inhibitor(s) currently being administered are satisfactory and the treatment may proceed in the absence of any adverse effects of the treatment. The HhP inhibitor dose and/or frequency of dose may be reduced if any adverse effects are observed. A lack of clinical response in the proliferation disorder to the treatment, after about four weeks of administering the HhP inhibitor, can be indicative of a need to modify the treatment regimen by increasing the dose of the HhP inhibitor, or increasing the frequency of the dosing of the HhP inhibitor, or administering an additional HhP inhibitor before, during or after the HhP inhibitor currently being administered, or a combination of two or more of the foregoing. In some embodiments, one or more additional HhP inhibitors are administered and the additional HhP inhibitor differs from the currently administered HhP inhibitor(s) in its mechanism of action by which it inhibits the HhP (e.g., itraconazole, or a pharmaceutically acceptable salt, prodrug, stereoisomer, or active metabolite of itraconazole, and vismodegib, or a pharmaceutically acceptable salt, prodrug, stereoisomer, or active metabolite of vismodegib). Multiple samples may be obtained and measurements determined and compared during the course of the treatment to monitor the proliferation disorder over time.

Monitoring may comprise visual inspection, palpation, imaging, assaying the presence, level, or activity of one or more biomarkers associated with the proliferation disorder and/or clinical response in a sample obtained from the subject, or a combination of two or more of the foregoing. Examples of biomarkers include Gli1, Gli2, Gli3, PSA, and the plasma level of HhP inhibitor or its metabolite.

In some embodiments, monitoring comprises monitoring at least one of the following parameters: tumor size, rate of change in tumor size, hedgehog levels or signaling, appearance of a new tumor, rate of appearance of new tumors, change in a symptom of the proliferation disorder, appearance of a new symptom associated with the proliferation disorder, quality of life (e.g., amount of pain associated with the proliferation disorder), or a combination of two or more of the foregoing. Following treatment, a decrease in tumor size, decreased rate of tumor growth, or decrease in hedgehog levels or signaling, or lack of appearance of new tumors, or decrease in rate of new tumors, or improvement of a symptom of the proliferation disorder, or lack of appearance of a new symptom of the proliferation disorder, or improvement in the quality of life can indicate a clinical response, i.e., that the selected HhP inhibitor(s) and treatment dosing regimen are satisfactory and do not need to be changed (though the dose and/or frequency of administration could be reduced if an adverse reaction exists). Likewise, following treatment, an increase in tumor size, or increased rate of tumor growth or no change in tumor size, or increase in hedgehog levels or signaling, or appearance of new tumors, or increase in rate of new tumors, or worsening of a symptom of the proliferation disorder, or appearance of a new symptom of the proliferation disorder, or a decrease in quality of life can indicate a lack of clinical response to the treatment and can indicate a need to modify the treatment regimen by increasing the dose of the HhP inhibitor (assuming that any adverse reaction, if present, is manageable), or increasing the frequency of the dosing of the HhP inhibitor (again, assuming that any adverse reaction, if present, is manageable), or administering an additional HhP inhibitor before, during or after the other HhP inhibitor, or a combination of two or more of the foregoing. As indicated above, if one or more additional HhP inhibitors are administered, it may be desirable for the additional HhP inhibitor(s) to differ from the currently administered HhP inhibitor(s) in its mechanism of action by which it inhibits the HhP (e.g., itraconazole, or a pharmaceutically acceptable salt, prodrug, stereoisomer, or active metabolite of itraconazole, and vismodegib, or a pharmaceutically acceptable salt, prodrug, stereoisomer, or active metabolite of vismodegib). Multiple samples may be obtained and measurements determined and compared during the course of the treatment to monitor the proliferation disorder over time.

An assessment of a subject's clinical response to HhP inhibition therapy may be made based on Hh levels or signaling, which may be assessed directly or indirectly by measuring a biomarker (an HhP biomarker) that represents the HhP signal itself or a modulator of the HhP signal (inducer or inhibitor). If the biomarker is an inhibitor of the HhP signal, and the level of the inhibitor is below normal, an assumption may be made that the HhP signal is elevated above normal. Likewise, if the biomarker is an inhibitor of the HhP signal, and the level of the inhibitor is above normal, an assumption may be made that the HhP signal is reduced below normal. If the biomarker is an inducer of the HhP signal, and the level of the inducer is below normal, an assumption may be made that the HhP signal is reduced below normal. Likewise, if the biomarker is an inducer of the HhP signal, and the level of the biomarker is above normal, an assumption may be made that the HhP signal is elevated above normal. Optionally, the accuracy of the aforementioned assumptions may be confirmed by measuring HhP signaling directly or by measuring other additional HhP biomarkers.

Hh levels or signaling may be monitored by measuring a biomarker representative of HhP activity, such as an Hh protein, or a nucleic acid encoding an HhP protein, such as an HhP ligand that activates the pathway and/or an upstream or downstream component(s) of the HhP, e.g., a receptor, activator or inhibitor of hedgehog, is analyzed. Ligands of the mammalian HhP include Sonic hedgehog (SHH), desert hedgehog (DHH), and Indian hedgehog (DHH). The levels of Gli transcription factors may be assessed as well (e.g., Gli1, Gli2, Gli3, or a combination or two or more of the foregoing).

Any of the aforementioned biomarkers can be detected in a sample obtained from the subject such as blood, urine, circulating tumor cells, a tumor biopsy, or a bone marrow biopsy. These biomarkers can also be detected by systemic administration of a labeled form of an antibody to a biomarker followed by imaging with an appropriate imaging modality. If a biomarker representative of HhP activity is measured and when compared to a reference level of that biomarker (a normal control or a level measured in a sample obtained from the subject at an earlier time, such as before initiation of the HhP inhibitor treatment), HhP signaling has increased or stayed the same following treatment with the HhP inhibitor, it can indicate a lack of clinical response to the treatment and a need to modify the treatment regimen by increasing the dose of the HhP inhibitor, or increasing the frequency of the dosing of the HhP inhibitor, or administering an additional HhP inhibitor before, during or after the HhP inhibitor currently being administered, or a combination of two or more of the foregoing. As indicated above, if one or more additional HhP inhibitors are administered, it may be desirable for the additional HhP inhibitor(s) to differ from the first HhP inhibitor in its mechanism of action by which it inhibits the HhP (e.g., itraconazole, or a pharmaceutically acceptable salt, prodrug, stereoisomer, or active metabolite of itraconazole, and vismodegib, or a pharmaceutically acceptable salt, prodrug, stereoisomer, or active metabolite of vismodegib). If a biomarker representative of HhP activity is measured (e.g., after about four weeks of administering the HhP inhibitor) and when compared to a reference level of that biomarker (a normal control or a level measured in a sample obtained from the subject at an earlier time, such as before initiation of the HhP inhibitor treatment), relative reduction of HhP signaling indicates that the HhP inhibitor dose, the HhP inhibitor dose frequency, and the choice of HhP inhibitor(s) currently being administered are satisfactory and the treatment may proceed in the absence of any adverse effects of the treatment. The HhP inhibitor dose and/or frequency of dose may be reduced if any adverse effects are observed. Multiple samples may be obtained and measurements determined and compared during the course of the treatment to monitor the proliferation disorder over time. By way of example, if the proliferation disorder is basal cell carcinoma, monitoring may comprise measuring Gli1 in a sample of skin tissue or tumor taken at one or more time points following HhP inhibitor administration (e.g., after about four weeks of administering the HhP inhibitor) and comparing the measured level of Gli1 to a reference level (a normal control or a level measured in a sample obtained from the subject at an earlier time, such as before initiation of HhP inhibitor treatment). If Gli1 increases or stays the same following treatment with the HhP inhibitor, it suggests a lack of clinical response to the treatment and can indicate a need to modify the treatment regimen as indicated above, by increasing the dose of the HhP inhibitor, or increasing the frequency of the dosing of the HhP inhibitor, or administering an additional HhP inhibitor before, during or after the other HhP inhibitor, or a combination of two or more of the foregoing. Multiple samples may be obtained and measurements determined and compared during the course of the treatment to monitor the proliferation disorder over time.

Biomarker Detection

The methods of the invention may comprise assaying the presence, level, or activity of one or more biomarkers in a sample obtained from a subject before, during, and/or after administering the HhP inhibitor to the subject. In some embodiments, the biomarker is associated with a proliferation disorder. For example, if the proliferation disorder is a cancer, the biomarker may be a tumor-specific antigen or tumor-associated antigen. In some embodiments, the biomarker is associated with a clinical response or lack thereof, such as the extent of HhP signaling. Examples of such biomarkers include Gli1, Gli2, Gli3, HhP ligand (such as Sonic hedgehog (SHH), desert hedgehog (DHH), or Indian hedgehog (DHH)), upstream or downstream component of the HhP (such as a receptor, activator, or inhibitor), PSA, and the plasma level of an administered HhP inhibitor or its metabolite.

Optionally, it can be determined whether the biomarker level has subsequently increased, diminished, or remained the same (e.g., in character and/or extent) relative to a reference biomarker level.

An assessment can be made of the subject's biomarker level one or more times after the initial treatment with the HhP inhibitor. Preferably, an assessment of the subject's biomarker level is also made before, during, or immediately after the subject's initial treatment with the HhP inhibitor (e.g., to establish a control or base-line for comparison to a subsequent assessment or assessments post-treatment). This may serve as a biomarker reference level. For example, an assessment of a biomarker level can be made from a sample obtained from the subject before treatment with the HhP inhibitor but after treatment with one or more other modalities such as chemotherapy, immunotherapy, and/or surgery.

In the methods of the invention, the subject's biomarker level can be monitored by making multiple assessments after the initial treatment at uniform time intervals (e.g., daily, weekly, monthly, or annually) or at non-uniform time intervals. Monitoring of the subject's biomarker level can continue for a pre-determined period of time, for a time determined based on therapeutic outcome, or indefinitely. Preferably, the subject's biomarker level is monitored from a time period starting prior to initial treatment with the HhP inhibitor and continuing for a period of time afterward (for example, for a period of at least five years), or indefinitely through the subject's life.

Typically, each assessment will involve obtaining an appropriate biological sample from the subject. The appropriate biological sample may depend upon the particular aspect of the subject's biomarker to be assessed (e.g., depending upon the particular assay). For example, in some embodiments, the biological sample will be one or more specimens selected from among whole blood, serum, peripheral blood mononuclear cells (PBMC), and a tissue (e.g., a tumor). Samples for assessments are taken at a time point appropriate to obtain information regarding the biomarker at the time of interest. For example, a sample may be taken from the subject from a time prior to administration of the HhP inhibitor and additional samples may be taken from the subject periodically after administration to determine the nature and extent of the biomarker levels observed.

The presence or level of biomarkers can be determined by measuring the level of biomarker nucleic acid (DNA or mRNA) or protein using known techniques. For example, immunological monitoring methods (i.e., an immunoassay) may be utilized to determine the level of biomarker, such as a competitive or immunometric assay. The assay may be, for example, a radioimmunoassay (MA), immunoradiometric assay (IRMA), enzyme-linked immunosorbent assay (ELISA), dot blot, slot blot, enzyme-linked immunosorbent spot (ELISPOT) assay, Western blot, Northern blot, Southern blot, peptide microarray, or nucleic acid microarray. The level of biomarker can be determined using surface plasmon resonance, fluorescence resonance energy transfer, bioluminescence resonance energy transfer, fluorescence quenching fluorescence, fluorescence polarization, mass spectrometry (MS), high-performance liquid chromatography (HPLC), high-performance liquid chromatography/mass spectrometry (HPLC/MS), high-performance liquid chromatography/mass spectrometry/mass spectrometry (HPLC/MS/MS), capillary electrophoresis, rod-gel electrophoresis, or slab-gel electrophoresis. The level of biomarker can be determined using RT-PCR, PCR, nucleic acid sequence based amplification assays (NASBA), transcription mediated amplification (TMA), or computerized detection matrix.

Assay standardization can include specific parameters to control for general variability, such as assay conditions, sensitivity and specificity of the assay, any in vitro amplification step involved, positive and negative controls, cutoff values for determining positive and negative test results from subjects' samples, and any statistical analytical methods to be used for test results can be determined and selected by one of ordinary skill in the art.

A reference level of a biomarker that the determined biomarker level of the sample is compared against may be, for example, a level from a sample obtained from the subject at an earlier time point (before or after administration of the HhP inhibitor), or the reference level of biomarker may be a normal level or a statistically calculated level from an appropriate subject population, representing a level that is consistent with a positive (desired) clinical outcome (i.e., the HhP inhibitor exhibits some degree of efficacy for the subject) or that is inconsistent with a positive clinical outcome (i.e., the HhP inhibitor does not exhibit efficacy for the subject). The reference level may be a single value (e.g., a cutoff value), a range, etc. For example, the reference level may be a range such that if the subject's biomarker level does not reach the reference level or falls within the range, the subject's biomarker level is deemed acceptable and no action need be taken. Conversely, if the subject's biomarker level reaches or exceeds the reference level or falls outside the acceptable range, this can indicate that some action should be taken, such as withholding or ceasing treatment with the HhP inhibitor, or reducing the amount of HhP inhibitor administered, and, optionally, administering an alternative treatment, i.e., other than an HhP inhibitor.

Examples of biomarkers that can be determined or assayed include prostate-specific antigen (PSA) in serum and PCA2 antigen in urine for prostate cancer. Another example of a biomarker that can be determined or assayed is Gli in whole blood, serum, plasma, urine, cerebrospinal fluid, and tissue for a variety of proliferation disorders, including cancers (see, for example, U.S. Patent Publication No. 20120083419, Altaba A. et al., "Methods and Compositions for Inhibiting Tumorigenesis," the content of which is incorporated herein by reference in its entirety). Other examples of biomarkers that are associated with cancers (i.e., that are consistent with or correlate with cancer) can be found at www.cancer.gov/cancertopics/factsheet/detection/tumor-markers, including ALK gene rearrangements in tumors for non-small cell lung cancer and anaplastic large cell lymphoma, alpha-fetoprotein (AFP) in blood for liver cancer and germ cell tumors, beta-2-microglobulin (B2M) in blood, urine, or cerebrospinal fluid for multiple myeloma, chronic lymphocytic leukemia, and some lymphomas, beta-human chorionic gonadotropin (beta-hcG) in urine or blood for choriocarcinoma and testicular cancer, BCR-ABL fusion gene in blood and/or bone marrow for chronic myeloid leukemia, BRAF mutation V600E in tumors for cutaneous melanoma and colorectal cancer, CA15-3/CA27.29 in blood for breast cancer, CA19-9 in blood for pancreatic cancer, gallbladder cancer, bile duct cancer, and gastric cancer, CA-125 in blood for ovarian cancer, calcitonin in blood for medullary thyroid cancer, carcinoembryonic antigen (CEA) in blood for colorectal cancer and breast cancer, CD20 in blood for non-Hodgkin lymphoma, chromogranin A (CgA) in blood for neuroendocrine tumors, chromosomes 3, 7, 17, and 9p21 in urine for bladder cancer, cytokeratin fragments 21-1 in blood for lung cancer, CGFR mutation analysis in tumors for non-small cell lung cancer, estrogen receptor (ER)/progesterone receptor (PR) in tumors for breast cancer, fibrin/fibrinogen in urine for bladder cancer, HE4 in blood for ovarian cancer, HER2/neu in tumors for breast cancer, gastric cancer, and esophageal cancer, immunoglobulins in blood and urine for multiple myeloma and Waldenstrom macroglobulinemia, KIT in tumors for gastrointestinal stromal tumor and mucosal melanoma, KRAS mutation analysis in tumors for colorectal cancer and non-small cell lung cancer, lactate dehydrogenase in blood for germ cell tumors, nuclear matrix protein 22 in urine for bladder cancer, thyroglobulin in tumors for thyroid cancer, urokinase plasminogen activator (uPA) and plasminogen activator inhibitor (PAI-1) in tumors for breast cancer, 5-protein signature (Oval) in blood for ovarian cancer, 21-gene signature (oncotype DX) in tumors for breast cancer, and 70-gene signature (mammaprint) cancer.gov/cancertopics/factsheet/detection/tumor-markers.

In some embodiments, the biomarker comprises PSA. PSA, also known as gamma-seminoprotein or kallikrein-3 (KLK3), is a glycoprotein enzyme encoded in humans by the KLK3 gene. PSA is a member of the kallikrein-related peptidase family. In the methods of the invention, determination or measurement of PSA level in a sample may be made directly by assessment of the amount of nucleic acid (e.g., DNA or mRNA) encoding PSA, PSA polypeptide (PSA gene product), or in the activity of PSA. Examples of PSA measurement methods that may be utilized include but are not limited to those described in Blase A. B. et al., "Five PSA Methods Compared by Assaying Samples with Defined PSA Ratios," *Clinical Chemistry*, May 1997, 43(5):843-845; Gelmini S. et al., "Real-time RT-PCT For The Measurement of Prostate-Specific Antigen mRNA Expression in Benign Hyperplasia and Adenocarcinoma of Prostate," *Clin. Chem.* *Lab. Med.*, 2003 March, 41(3):261-265; and Kalfazade N. et al., "Quantification of PSA mRNA Levels in Peripheral Blood of Patients with Localized Prostate Adenocarcinoma Before, During and After Radical Prostatectomy by Quantitative Real-Time PCR (qRT-PCR)," *Int. Urol., Nephrol.*, 2009, Epub 2008 Jun. 27, 41(2):273-279, which are each incorporated herein by reference in its entirety.

In accordance with the invention, PSA level may be determined by measuring total PSA (tPSA; measure of all PSA in a sample), free PSA (fPSA; amount free, unbound PSA protein), or complex PSA (cPSA; the amount of PSA that is complexed with or bound to other proteins) in a sample. Optionally, determination of PSA level further comprises determining PSA velocity or PSA doubling time. PSA velocity is the rate of change in a subject's PSA level over time, typically expressed as ng/mL per year. PSA doubling time is the period of time over which a subject's PSA level doubles. Pro-PSA refers to several different inactive precursors of PSA. Preferably, the mature, active form of PSA, lacking the leader peptide, is determined. However, pro-PSA may be measured as an alternative, or in addition to, the mature form (Masood A. K. et al., "Evolving Role of Pro-PSA as a New Serum Marker for the Early Detection of Prostate Cancer", *Rev. Urol.*, 2002, 4(4):198-200).

The methods of the invention may comprise assessing the level of PSA in a sample obtained from a subject before, during, and/or after administering the HhP inhibitor to the subject to determine whether the PSA level has subsequently increased, diminished, or remained the same (e.g., in character and/or extent) relative to a reference PSA level.

An assessment can be made of the subject's PSA level one or more times after the initial treatment with the HhP inhibitor. Preferably, an assessment of the subject's PSA level is also made before, during, or immediately after the subject's initial treatment with the HhP inhibitor (e.g., to establish a control or base-line for comparison to a subsequent assessment or assessments post-treatment). This may serve as a PSA reference level. For example, an assessment of PSA level can be made from a sample obtained from the subject before treatment with the HhP inhibitor but after treatment with one or more other modalities such as chemotherapy, immunotherapy, and/or surgery.

In the methods of the invention, the subject's PSA level can be monitored by making multiple assessments after the initial treatment at uniform time intervals (e.g., daily, weekly, monthly, or annually) or at non-uniform time intervals. Monitoring of the subject's PSA level can continue for a pre-determined period of time, for a time determined based on therapeutic outcome, or indefinitely. Preferably, the subject's PSA level is monitored from a time period starting prior to initial treatment with the HhP inhibitor and continuing for a period of time afterward (for example, for a period of at least five years), or indefinitely through the subject's life.

Typically, each assessment will involve obtaining an appropriate biological sample from the subject. The appropriate biological sample may depend upon the particular aspect of the subject's PSA to be assessed (e.g., depending upon the particular assay). For example, in some embodiments, the biological sample will be one or more specimens selected from among whole blood, serum, peripheral blood mononuclear cells (PBMC), and a tissue (e.g., a tumor). Samples for assessments are taken at a time point appropriate to obtain information regarding the PSA at the time of interest. For example, a sample may be taken from the subject from a time prior to administration of the HhP inhibitor and additional samples may be taken from the subject periodically after administration to determine the nature and extent of the PSA levels observed.

The level of PSA can be determined by measuring the level of PSA nucleic acid (DNA or mRNA) or protein using known techniques. For example, immunological monitoring methods (i.e., an immunoassay) may be utilized to determine the level of PSA, such as a competitive or immunometric assay. The assay may be, for example, a radioimmunoassay (MA), immunoradiometric assay (IRMA), enzyme-linked immunosorbent assay (ELISA), dot blot, slot blot, enzyme-linked immunosorbent spot (ELISPOT) assay, Western blot, Northern blot, Southern blot, peptide microarray, or nucleic acid microarray. The level of PSA can be determined using surface plasmon resonance, fluorescence resonance energy transfer, bioluminescence resonance energy transfer, fluorescence quenching fluorescence, fluorescence polarization, mass spectrometry (MS), high-performance liquid chromatography (HPLC), high-performance liquid chromatography/mass spectrometry (HPLC/MS), high-performance liquid chromatography/mass spectrometry/mass spectrometry (HPLC/MS/MS), capillary electrophoresis, rod-gel electrophoresis, or slab-gel electrophoresis. The level of PSA can be determined using RT-PCR, PCR, nucleic acid sequence based amplification assays (NASBA), transcription mediated amplification (TMA), or computerized detection matrix.

Assay standardization can include specific parameters to control for general variability, such as assay conditions, sensitivity and specificity of the assay, any in vitro amplification step involved, positive and negative controls, cutoff values for determining positive and negative test results from subjects' samples, and any statistical analytical methods to be used for test results can be determined and selected by one of ordinary skill in the art.

A reference level of PSA that the determined PSA level of the sample is compared against may be, for example, a level from a sample obtained from the subject at an earlier time point (before or after administration of the HhP inhibitor), or the reference level of PSA may be a statistically calculated level from an appropriate subject population, representing a level that is consistent with a positive (desired) clinical outcome (i.e., the HhP inhibitor exhibits some degree of efficacy for the subject) or that is inconsistent with a positive clinical outcome (i.e., the HhP inhibitor does not exhibit efficacy for the subject). The reference level may be a single value (e.g., a cutoff value), a range, etc. For example, the reference level may be a range such that if the subject's PSA level does not reach the reference level or falls within the range, the subject's PSA level is deemed acceptable and no action need be taken. Conversely, if the subject's PSA level reaches or exceeds the reference level or falls outside the acceptable range, this can indicate that some action should be taken, such as withholding or ceasing treatment with the HhP inhibitor, or reducing the amount of HhP inhibitor administered, and, optionally, administering an alternative treatment, i.e., other than an HhP inhibitor.

The methods of the invention can further include the step of monitoring the subject, e.g., for a change (e.g., an increase or decrease) in one or more of: tumor size; hedgehog levels or signaling; stromal activation; levels of one or more cancer markers; the rate of appearance of new lesions; the appearance of new disease-related symptoms; the size of soft tissue mass, e.g., a decreased or stabilization; quality of life, e.g., amount of disease associated pain; or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same HhP inhibitor, alone or in combination with, the same therapeutic agent, or for additional treatment with additional agents. Generally, a decrease in one or more of the parameters described above is indicative of the improved condition of the subject, although with serum hemoglobin levels, an increase can be associated with the improved condition of the subject.

The methods of the invention can further include the step of analyzing a nucleic acid or protein from the subject, e.g., analyzing the genotype of the subject. In one embodiment, a hedgehog protein, or a nucleic acid encoding a hedgehog ligand and/or an upstream or downstream component(s) of the hedgehog signaling, e.g., a receptor, activator or inhibitor of hedgehog, is analyzed. The elevated hedgehog ligand can be detected in blood, urine, circulating tumor cells, a tumor biopsy or a bone marrow biopsy. The elevated hedgehog ligand can also be detected by systemic administration of a labeled form of an antibody to a hedgehog ligand followed by imaging. In addition to determination of PSA in accordance with the invention, the analysis can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response phenotype or genotype. The nucleic acid or protein can be analyzed at any stage of treatment, but preferably, prior to administration of the HhP inhibitor and/or therapeutic agent, to thereby determine appropriate dosage(s) and treatment regimen(s) of the HhP inhibitor (e.g., amount per treatment or frequency of treatments) for prophylactic or therapeutic treatment of the subject.

In certain embodiments, the methods of the invention further include the step of detecting elevated hedgehog ligand in the subject, prior to, or after, administering a HhP inhibitor to the subject. The elevated hedgehog ligand can be detected in blood, urine, circulating tumor cells, a tumor biopsy or a bone marrow biopsy. The elevated hedgehog ligand can also be detected by systemic administration of a labeled form of an antibody to a hedgehog ligand followed by imaging. The step of detecting elevated hedgehog ligand can include the steps of measuring hedgehog ligand in the patient prior to administration of the other cancer therapy, measuring hedgehog ligand in the patient after administration of the other cancer therapy, and determining if the amount of hedgehog ligand after administration of the other chemotherapy is greater than the amount of hedgehog ligand before administration of the other chemotherapy. The other cancer therapy can be, for example, a therapeutic agent or radiation therapy.

Hedgehog Pathway Signaling Inhibitors

Hh pathway activation begins when the Hh ligand binds to and inhibits the transmembrane receptor Patched1 (Ptch1), allowing the signal transducer Smoothened (Smo) to activate Gli transcription factors and amplify Hh target gene expression. Thus far, all of the nuclear events ascribed to Hh occur through the Gli transcription factors, with Gli1 acting predominantly as an activator, Gli3 acting predominantly as a repressor, and Gli2 possessing both repressive and activator functions.

Any HhP inhibitor may be used in the invention as a monotherapy or in combination regimens with one or more other HhP inhibitors and/or in combination with one or more other therapeutic or prophylactic agents or treatments, such as chemotherapeutic agents, radiation, surgery, and immunotherapy. HhP inhibitors and biological assays and in vivo models that may be employed for the identification and characterization of inhibitors of various members of the HhP are described in Peukert S. and Miller-Moslin K., "Small-Molecule Inhibitors of the Hedgehog Signaling Pathway as Cancer Therapeutics", Chem Med Chem, 2010, 5(4):500-512, Sahebjam, et al., "The Utility of Hedgehog Signaling Pathway Inhibition for Cancer", The Oncologist, 2012, 17:1090-1099; Liu H. et al., "Clinical Implications of Hedgehog Signaling Pathway Inhibitors," Chin. J. Cancer, 2011, 30(1):13-26; Atwood Scott X. et al., "Hedgehog Pathway Inhibition and the Race Against Tumor Evolution," J. Cell Biol., 199(2):193-197; and U.S. Patent Publication No. 20090203713, Beachy P. A. et al., "Hedgehog Pathway Antagonists to Treat Disease," the contents of each of which is incorporated herein by reference in its entirety.

Drug discovery efforts aimed at identifying inhibitors of the Hh signaling pathway have facilitated the development of a multitude of biological assay systems for interrogating Hh pathway activity, including cell-based assays, tissue assays, and at least one in vivo assay, and binding assays have been used to confirm the specific proteins in the pathway being targeted. In addition, animal disease models have been established for a variety of cancer types, including medulloblastoma, basal cell carcinoma (BCC), breast cancer, lymphoma, and chronic myeloid leukemia (CML), as well as pancreatic, prostate, colorectal and small-cell lung cancer (SCLC). These models have been used to evaluate the effects of various small molecule HhP inhibitors on tumor growth and progression.

The Smoothened receptor (Smo) has thus far shown to be the most "druggable" target in the pathway, as demonstrated by the structurally diverse array of both naturally occurring and fully synthetic small molecule Smo inhibitors reported. Efforts are ongoing to identify additional druggable nodes in the pathway, and promising initial results have been demonstrated for targeting the Sonic hedgehog protein (Shh) and the downstream target Gli1 with small molecule inhibitors.

The most common way to target HhP is modulation of Smo. Smo is a G protein-coupled receptor protein encoded by the Smo gene of the HhP. Smo is the molecular target of the teratogen cyclopamine. Antagonists and agonists of Smo have been shown to affect the pathway regulation downstream. The most clinically advanced Smo targeting agents are cyclopamine-competitive. Itraconazole (Sporanox) has also been shown to target Smo through a mechanism distinct from cyclopamine and vismodegib. Itraconazole inhibits Smo in the presence of mutations conferring resistance to vismodegib and other cyclopamine-competitive antagonists such as IPI-926 and LDE-225. Ptch and Gli3 (5E1) antibodies are also a way to regulate the pathway. A downstream effector and strong transcriptional activator siRNA Gli1 has been used to inhibit cell growth and promote apoptosis. Arsenic trioxide (Trisenox) has also been shown to inhibit hedgehog signaling by interfering with Gli function and transcription.

As used herein, the terms "hedgehog inhibitor", "hedgehog pathway inhibitor", "HhP inhibitor", or in most contexts "inhibitor" refer to an agent capable of blocking or reducing cellular responses to the hedgehog signaling pathway, e.g., in cells with an active hedgehog signaling pathway, and more specifically, inhibiting cellular responses, directly or indirectly, to the hedgehog family of secreted growth factors. The hedgehog inhibitor may antagonize hedgehog pathway activity through a number of routes, including, but not limited to, by interfering with the inhibitory effect that Ptch exerts on Smo; by activating Smo without affecting Ptc; by influencing Smo function by directly binding to Smo; and/or by activating the pathway downstream of Smo. Exemplary hedgehog inhibitors may include, but are not limited to, steroidal alkaloids such as cyclopamine and jervine. In some embodiments, the HhP inhibitor antagonizes HhP activity by binding to a component (effector molecule) of the pathway (e.g., a Hedgehog receptor such as Ptch or Smo, or a signaling mediator such as Gli1, Gli2, or Gli3), interfering with the inhibitory effect that a component of the pathway exerts on another component of the pathway, by activating a component of the pathway without affecting another component, by activating a component of the pathway downstream of Smo, or by reducing or eliminating expression of a component of the pathway. In some embodiments, the HhP inhibitor antagonizes HhP activity by binding to Smo, interfering with the inhibitory effect that Ptch exerts on Smo, by activating Smo without affecting Ptch, by activating the pathway downstream of Smo, or by reducing or eliminating expression of Smo. In some embodiments, the HhP inhibitor is cyclopamine-competitive. In some embodiments, the HhP inhibitor is cyclopamine-competitive and the proliferation disorder is lung cancer, basal cell carcinoma, prostate cancer, or other cancer. The HhP inhibitor may be any class of agent or treatment capable of blocking or reducing cellular responses to the HhP and may be, for example, a polypeptide (e.g., protein, peptide, immunoglobulin (antibody or antibody fragment)), a nucleic acid (e.g., antisense molecule, ribozyme, or interfering RNA such as siRNA or shRNA), or a small molecule. The HhP inhibitor may be active upon administration to the subject, and/or active upon metabolic processing or other mechanisms in vivo (i.e., as one or more active metabolites).

Although the term "HhP inhibitor" and its grammatical variants are used herein to refer to agents capable of blocking or reducing cellular responses to the hedgehog signaling pathway, e.g., in cells with an active hedgehog signaling pathway, and more specifically, inhibiting cellular responses, directly or indirectly, to the hedgehog family of secreted growth factors, the invention encompasses use of HhP inhibitors to treat proliferation disorders (e.g., cancer), whether that particular agent's primary mechanism of action in treating the proliferation disorder in question is through the above-described HhP inhibition or through some other mechanism of action, such as inhibition of angiogenesis. For example, itraconazole is an HhP inhibitor and inhibits angiogenesis. In treating some cancers in accordance with the invention, the HhP inhibitor may act by a mechanism completely independent of its HhP inhibition properties. Thus, the identification of an agent as being an HhP inhibitor is not limited to the context in which it is being used, but rather to its ability to inhibit the HhP.

Suitable hedgehog inhibitors for use with the present invention include, for example, those described and disclosed in U.S. Pat. No. 7,230,004, U.S. Patent Application Publication No. 2008/0293754, U.S. Patent Application Publication No. 2008/0287420, U.S. Patent Application Publication No. 2008/0293755, and U.S. Patent Application Publication No. 2008/0019961, the entire disclosures of which are incorporated by reference herein.

Examples of other suitable hedgehog inhibitors also include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354.

Additional examples of HhP inhibitors include, but are not limited to, GDC-0449 (also known as RG3616 or vismodegib) described in, e.g., Von Hoff D. et al., *N. Engl. J. Med.* 2009; 361(12):1164-72; Robarge K. D. et al., *Bioorg. Med. Chem. Lett.,* 2009; 19(19):5576-81; Yauch, R. L. et al., *Science,* 2009, 326: 572-574; Rudin, C. et al., *New England J of Medicine,* 2009, 361-366; BMS-833923 (also known as XL139) described in, e.g., in Siu L. et al., *J. Clin. Oncol.* 2010; 28:15s (suppl; abstr 2501); and National Institute of Health Clinical Trial Identifier No. NCT006701891; LDE-225 described, e.g., in Pan S. et al., *ACS Med. Chem. Lett.,* 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.,* 2009; 329(3):995-1005; 1-piperazinyl-4-arylphthalazines or analogues thereof, described in Lucas B. S. et al., *Bioorg. Med. Chem. Lett.,* 2010; 20(12):3618-22.

HhP inhibitors useful in the current invention can contain a basic functional group, such as amino or alkylamino, and are thus capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately treating the compound in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, besylate, glucoheptonate, lactobionate, and laurylsulphonate salts and the like (see, for example, Berge et al., "Pharmaceutical Salts", *J. Pharm. Sci.,* 1977, 66:1-19).

Pharmaceutically acceptable salts include, but are not limited to, conventional nontoxic salts or quaternary ammonium salts of the compounds, e.g., from non-toxic organic or inorganic acids. For example, such conventional nontoxic salts include, but are not limited to, those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, benzenesulfonic, ethane disulfonic, oxalic, isothionic, and the like.

In other cases, the HhP inhibitors can contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately treating the compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

If administered with another therapeutic agent, the HhP inhibitor and the therapeutic agent can be administered as separate compositions, e.g., pharmaceutical compositions, or administered separately, but via the same route (e.g., both orally or both intravenously), or administered in the same composition, e.g., pharmaceutical composition.

In one embodiment, the HhP inhibitor is administered prior to detection of the proliferation disorder. In another embodiment, the HhP inhibitor is administered after detection of the proliferation disorder. In one embodiment, the proliferation disorder is cancer (prostate cancer, basal cell carcinoma, lung cancer, or other cancer), and the HhP inhibitor is administered prior to detection of the cancer. In another embodiment, the proliferation disorder is cancer (prostate cancer, basal cell carcinoma, lung cancer, or other cancer), and the HhP inhibitor is administered after detection of the cancer.

Some HhP inhibitors may comprise one or more asymmetric centers, and thus can exist in various isomeric forms, i.e., stereoisomers (enantiomers, diastereomers, cis-trans isomers, E/Z isomers, etc.). Thus, HhP inhibitors can be in the form of an individual enantiomer, diastereomer or other geometric isomer, or can be in the form of a mixture of stereoisomers. Enantiomers, diastereomers and other geometric isomers can be isolated from mixtures (including racemic mixtures) by any method known to those skilled in the art, including chiral high pressure liquid chromatography (HPLC) and the formation and crystallization of chiral salts or prepared by asymmetric syntheses; see, for example, Jacques, et al., Enantiomers, Racemates and Resolutions (Wiley Interscience, New York, 1981); Wilen, S. H., et al., *Tetrahedron,* 1977, 33:2725; Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972).

Hedgehog pathway inhibitors are exemplified herein by itraconazole, including pharmaceutically acceptable, salts, prodrugs, isomers, and metabolites thereof. Isomers of itraconazole include each of its stereoisomers (Castro-Puyana M. et al., "Separation and Quantitation of the Four Stereoismers of Itraconazole in Pharmaceutical Formulations by Electrokinetic Chromatography", *Electrophoresis,* 2006, 27(4):887-895; Kunze K. L. et al., "Stereochemical Aspects of Itraconazole Metabolism In Vitro and In Vivo," *Drug Metab. Dispos.,* 2006, Epub 2006 Jan. 13, 34(4):583-590, and as corrected in "Correction to "Stereochemical Aspects of Itraconazole Metabolism In Vitro and In Vivo," *Drug Metab. Dispos.,* 2012, 40(12):2381); Chong C. R. et al., "Inhibition of Angiogenesis by the Antifungal Drug Itraconazole," *ACS Chemical Biology,* 2007, 2(4):263-270; Kim J. et al., "Itraconazole, a Commonly Used Antifungal that Inhibits Hedgehog Pathway Activity and Cancer Growth," *Cancer Cell,* 2010, 17(4):388-399); Patent Publication No. WO/2008/124132, Liu J. et al., entitled "Chirally Pure Isomers of Itraconazole and Inhibitors of Lanosterol 14A-

Demethylase For Use as Angiogenesis Inhibitors"). In some embodiments, the HhP inhibitor comprises a stereoisomer of itraconazole selected from (2R,4S,2'R), (2R,4S,2'S), (2S,4R, 2S'R), or (2S,4R2'S). In some embodiments, the HhP inhibitor comprises an itraconazole analogue in which the sec-butyl side chain has been replaced with one or more moieties, relative to itraconazole. For example, the itraconazole analogue may be one in which the native sec-butyl side chain is replaced with $C_1$-$C_8$ alkyl, $C_2$-$C_8$ alkenyl, or $C_2$-$C_8$ alkynyl, that are straight, branched, or cyclic, and are unsubstituted or substituted one or more times at any position with a $C_1$-$C_8$ alkoxy, $C_6$-$C_{10}$ aryl, $N_3$, OH, Cl, Br, I, F, $C_6$-$C_{10}$ aryl oxy, $C_1$-$C_8$ alkyl carboxy, aryl carboxy, wherein any substituent can be further substituted with any of the foregoing.

In some embodiments, the HhP inhibitor is an azole antifungal drug-containing composition as described in U.S. Patent Application Publication No. 20030225104 (Hayes et al., "Pharmaceutical Compositions for Poorly Soluble Drugs," issued as U.S. Pat. No. 6,881,745 which is incorporated herein by reference in its entirety). In some embodiments, the composition in vivo provides a mean $C_{MAX}$ of at least about 100 ng/ml (e.g., 150 to 250 ng/ml) after administration in the fasted state. In some embodiments, the HhP inhibitor is a composition including an azole antifungal drug, such as itraconazole, and at least one polymer having one or more acidic functional groups. In a particularly preferred form the polymer is a polycarboxylic acid such as a hydroxypropyl methylcellulose phthalate such as that available from Shin-Etsu Chemical Industry Co Ltd as HP-50, HP-55 or HP-55S. In some embodiments, the HhP inhibitor is a composition including an azole antifungal drug, such as itraconazole, and at least one polymer having one or more acidic functional groups, wherein the composition in vivo provides a mean $C_{MAX}$ of at least 100 ng/ml (e.g., 150 to 250 ng/ml). In some embodiments, the HhP inhibitor is a composition including about 100 mg of an azole antifungal drug, such as itraconazole, and optionally at least one polymer having acidic functional groups.

In some embodiments, the HhP inhibitor is the SUBACAP™ formulation of itraconazole. The SUBACAP™ formulation is a solid dispersion wherein itraconazole is associated with acidic molecules and the formulation allows for excellent absorption at pH 5.5-7. Itraconazole release occurs in the intestines; therefore, fed or fasted state does not affect the absorption, nor are there restrictions for achlorhydric patients or patients on proton-pump inhibitor drugs for high acid control.

In some embodiments, an HhP inhibitor such as itraconazole, or a pharmaceutically acceptable salt, prodrug, stereoisomer, or active metabolite thereof, is administered in a SUBA® formulation at a dose in the range of 100 mg to 600 mg per day. In some embodiments, 150 mg of an HhP inhibitor such as itraconazole, or a pharmaceutically acceptable salt, prodrug, stereoisomer, or active metabolite thereof, is administered in a SUBA® formulation two or more times per day. In some embodiments, 200 mg of an HhP inhibitor such as itraconazole, or a pharmaceutically acceptable salt, prodrug, stereoisomer, or active metabolite thereof, is administered in a SUBA® formulation two or more times per day.

Methods of Treatment

One aspect of the invention concerns a method for treating a proliferation disorder in a subject, comprising administering a composition comprising a Hedgehog pathway (HhP) inhibitor to the subject, wherein the composition is administered (preferably, orally) in an effective amount to achieve a plasma trough level of at least about 1,000 ng/mL of the HhP inhibitor.

The method of prognosticating an outcome of prostate cancer treatment and method of determining the efficacy of HhP inhibitor therapy may further comprise administering an HhP inhibitor therapy. Thus, another aspect of the invention concerns a method for treating prostate cancer in a subject, comprising administering Hedgehog pathway (HhP) inhibitor therapy to the subject; and carrying out a method of the invention (i.e., a method of prognosticating an outcome of prostate cancer treatment with a HhP inhibitor therapy, or a method of determining the efficacy of HhP inhibitor therapy).

In treating a proliferation disorder (e.g., prostate cancer, basal cell carcinoma, lung cancer, or other cancer) one or more HhP inhibitors (and compositions containing them) may be administered by any route effective for delivery to the desired tissues, e.g., administered orally, parenterally (e.g., intravenously), intramuscularly, sublingually, buccally, rectally, intranasally, intrabronchially, intrapulmonarily, intraperitoneally, topically, transdermally and subcutaneously, for example. The HhP inhibitors can be formulated for the most effective route of administration. For example, an HhP inhibitor may be administered orally or locally (e.g., by direct injection) to a desired site, such as a precancerous lesion or tumor (e.g., prostate cancer lesion or prostate tumor or other cancer tumor). The amount administered in a single dose may be dependent on the subject being treated, the subject's weight, the manner of administration and the judgment of the prescribing physician. Generally, however, administration and dosage and the duration of time for which a composition is administered will approximate those which are necessary to achieve a desired result.

The selected dosage level of the HhP inhibitor will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of an HhP inhibitor will be that amount of the inhibitor which is the lowest dose effective to produce a therapeutic effect. Such an effective dose will generally depend upon the factors described above. Generally, oral, intravenous and subcutaneous doses of the HhP inhibitor for a subject, when used for the indicated effects, will range from about 0.0001 mg to about 1000 mg per day, or about 0.001 mg to about 1000 mg per day, or about 0.01 mg to about 1000 mg per day, or about 0.1 mg to about 1000 mg per day, or about 0.0001 mg to about 600 mg per day, or about 0.001 mg to about 600 mg per day, or about 0.01 mg to about 600 mg per day, or about 0.1 mg to about 600 mg per day, or about 200 mg to 600 mg per day. The optimal pharmaceutical formulations can be readily determined by one of ordinary skill in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

The subject receiving treatment is any animal in need, including primates, in particular humans, equines, cattle, swine, sheep, poultry, dogs, cats, mice and rats. The subject may be any gender, though some proliferation disorders are gender-specific (e.g., prostate cancer, ovarian cancer).

The HhP inhibitors can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The HhP inhibitors can be administered orally, intravenously, intraperitoneally, topically, transdermally, intramuscularly, subcutaneously, intranasally, sublingually, or by any other route.

Single or multiple administrations of the HhP inhibitor can be carried out with dose levels and patterns being selected by the treating physician, optionally based on the level of a biomarker (e.g., PSA level for prostate cancer) determined in a sample obtained from the subject relative to a reference biomarker level (e.g., reference PSA level).

In some embodiments, the HhP inhibitor is administered with one or more other therapeutic treatments before, during, or after the HhP inhibitor. The HhP inhibitor and the therapeutic agent that is a non-HhP inhibitor can be administered within the same formulation or different formulations. If administered in different formulations, the HhP inhibitor and the therapeutic agent can be administered by the same route or by different routes.

Depending on the intended mode of administration, the inhibitors and therapeutic agents used in the methods described herein may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. Each dose may include an effective amount of a compound used in the methods described herein in combination with a pharmaceutically acceptable carrier and, in addition, may include other medicinal agents, pharmaceutical agents, carriers, adjuvants, diluents, etc.

Liquid pharmaceutically administrable compositions can prepared, for example, by dissolving, dispersing, etc., a compound for use in the methods described herein and optional pharmaceutical adjuvants in an excipient, such as, for example, water, saline aqueous dextrose, glycerol, ethanol, and the like, to thereby form a solution or suspension. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art (see, for example, Remington's Pharmaceutical Sciences, 18th Ed. (1990), Mack Publishing Co., Easton, Pa., the entire disclosure of which is hereby incorporated by reference).

Formulations comprising HhP inhibitors may be presented in unit-dose or multi-dose containers (packs), for example, sealed ampoules and vials, and may be stored in a freeze dried (lyophilized) condition requiring only the condition of the sterile liquid carrier, for example, water for injections, prior to use. Examples of pack types that may be utilized include, but are not limited to, multidose packs (also referred to as reclosables), such as bottles, aerosol packs, and tubes, and unit dose packs (also referred to as non-reclosables), such as ampoules, blister packs pre-filled syringes, vials, sachets, and form/blow-fill-seal (FFS, BFS) in various pack formats. In one embodiment, the itraconazole is in a SUBA® formulation (e.g., SUBACAP™ formulation) presented in a blister pack. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Patients in need of treatment using the methods and compositions of the present invention can be identified using standard techniques known to those in the medical or veterinary professions, as appropriate. In some embodiments, the proliferation disorder to be treated is one characterized by upregulation (elevation) of Hh level and/or HhP signaling above the constitutive level (or normal level for the normal cell type in question). As indicated above, optionally, subjects in need of treatment (or further treatment) of a proliferation disorder such as prostate cancer, basal cell carcinoma, lung cancer, or other cancer, may be selected as an individual particularly suitable for treatment with an HhP inhibitor, based on Hh level or signaling, which may be assessed directly or indirectly by measuring a biomarker (an HhP biomarker) that represents the HhP signal itself or a modulator of the HhP signal (inducer or inhibitor).

Cancer is an example of a proliferation disorder that may be treated and monitored using methods of the invention. The terms "cancer" and "malignancy" are used herein interchangeably to refer to or describe the physiological condition in mammals that is typically characterized by unregulated cell growth. The methods and compositions of the invention can be utilized for early, middle, or late stage disease, and acute or chronic disease. The cancer may be drug-resistant or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer. In some embodiments, the cancer is a hematologic malignancy (for example, multiple myeloma or leukemia). In some embodiments, the cancer is a non-hematologic malignancy.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types that may potentially be treated using the methods and compositions of the present invention are also listed in Table 1.

TABLE 1

Examples of Cancer Types

Acute Lymphoblastic Leukemia, Adult
Acute Lymphoblastic Leukemia, Childhood
Acute Myeloid Leukemia, Adult
Acute Myeloid Leukemia, Childhood
Adrenocortical Carcinoma
Adrenocortical Carcinoma, Childhood
AIDS-Related Cancers
AIDS-Related Lymphoma
Anal Cancer
Astrocytoma, Childhood Cerebellar
Astrocytoma, Childhood Cerebral
Basal Cell Carcinoma
Bile Duct Cancer, Extrahepatic
Bladder Cancer
Bladder Cancer, Childhood
Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt' s Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Hairy Cell Leukemia
Head and Neck Cancer
Hepatocellular (Liver) Cancer, Adult (Primary)
Hepatocellular (Liver) Cancer, Childhood (Primary)
Hodgkin's Lymphoma, Adult
Hodgkin's Lymphoma, Childhood
Hodgkin's Lymphoma During Pregnancy
Hypopharyngeal Cancer
Hypothalamic and Visual Pathway Glioma, Childhood TABLE 1-continued Examples of Cancer Types Intraocular Melanoma
Islet Cell Carcinoma (Endocrine Pancreas)
Kaposi's Sarcoma
Kidney (Renal Cell) Cancer
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer

TABLE 1-continued

Examples of Cancer Types

Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma
Rhabdomyosarcoma, Childhood
Salivary Gland Cancer
Salivary Gland Cancer, Childhood
Sarcoma, Ewing's Family of Tumors
Sarcoma, Kaposi's
Sarcoma, Soft Tissue, Adult
Sarcoma, Soft Tissue, Childhood
Sarcoma, Uterine
Sezary Syndrome
Skin Cancer (non-Melanoma)
Skin Cancer, Childhood
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome
Testicular Cancer
Thymoma, Childhood
Thymoma and Thymic Carcinoma
Thyroid Cancer
Thyroid Cancer, Childhood
Transitional Cell Cancer of the Renal Pelvis and Ureter
Trophoblastic Tumor, Gestational
Unknown Primary Site, Carcinoma of, Adult
Unknown Primary Site, Cancer of, Childhood
Unusual Cancers of Childhood
Ureter and Renal Pelvis, Transitional Cell Cancer
Urethral Cancer
Uterine Cancer, Endometrial
Uterine Sarcoma
Vaginal Cancer
Visual Pathway and Hypothalamic Glioma, Childhood
Vulvar Cancer
Waldenström's Macroglobulinemia
Wilms' Tumor In some embodiments, the proliferation disorder treated and/or monitored using the methods of the invention is prostate cancer. In some embodiments, the prostate cancer is a pre-cancer of the prostate. In some embodiments, the prostate cancer is metastatic. In some embodiments, the prostate cancer is non-metastatic. In some embodiments, the prostate cancer is one that exhibits elevated expression of a HhP member or ligand (i.e., a HhP-associated cancer). In some embodiments, the prostate cancer is castration-resistant. In some embodiments, the prostate cancer is non-castration resistant. In some embodiments, the prostate cancer is metastatic, castration-resistant prostate cancer. In some embodiments, the prostate cancer is non-metastatic, castration-resistant prostate cancer.

In some embodiments, the proliferation disorder treated and/or monitored using the methods of the invention is skin cancer, such as melanoma, or a non-melanoma, such as basal cell carcinoma (BCC). Thus, in some embodiments, the proliferation disorder treated and/or monitored using the methods of the invention is BCC, which is a nonmelanocytic skin cancer (i.e., an epithelial tumor) and is the most common form of skin cancer. In some embodiments, the BCC is a type selected from among nodular BCC, cystic BCC, cicatricial BCC, infiltrative BCC, micronodular BCC, superficial BCC, pigmented BCC, Jacobi ulcer, fibroepithelioma of Pinkus, polyoid basal-cell carcinoma, pore-like BCC, or aberrant BCC. In some embodiments, the BCC is sporadic BCC. In some embodiments, the BCC is hereditary BCC. In some embodiments, the subject has a BCC tumor equal to or greater than 4 mm.

In some embodiments, the proliferation disorder is lung cancer (stage I, stage II, stage IIIa, stage IIIb, or stage IV). In some embodiments, the lung cancer is a non-small cell lung cancer (NSCLC), such as squamous cell carcinoma, non-squamous cell carcinoma, large cell carcinoma, and adenocarcinoma. In some embodiments, the lung cancer is small cell lung cancer (SCLC). In some embodiments, the lung cancer is non-squamous cell lung carcinoma. In some embodiments, the lung cancer is mesothelioma (e.g., malignant pleural mesothelioma). In some embodiments, the lung cancer is late-stage metastatic NSCLC.

Optionally, one or more tests are performed before and/or after treatment of the lung cancer, such as bone scan, chest x-ray, complete blood count (CDC), CT scan, liver function tests, magnetic resonance imaging (MRI), positron emission tomography (PET), sputum test, and thoracentesis. Optionally, a biopsy may be obtained before and/or after treatment of the lung cancer (e.g., bronchoscopy with biopsy, CT-scan directed needle biopsy, endoscopic esophageal ultrasound with biopsy, mediastinoscopy with biopsy, open lung biopsy, pleural biopsy, and video assisted thoracoscopy).

In some embodiments, the proliferation disorder to be treated is prostate cancer e.g., non-metastatic castrate resistant prostate cancer or other prostate cancer. In some embodiments, the prostate cancer is treated by administering an HhP inhibitor such as itraconazole, or a pharmaceutically acceptable salt, prodrug, stereoisomer, or active metabolite thereof, at a dose in the range of 100 mg to 600 mg per day. In some embodiments, the prostate cancer is treated by administering 200 mg of an HhP inhibitor such as itraconazole, or a pharmaceutically acceptable salt, prodrug, stereoisomer, or active metabolite thereof, two or more times per day. Preferably, the HhP inhibitor such as itraconazole, or a pharmaceutically acceptable salt, prodrug, stereoisomer, or active metabolite thereof, is orally administered in a SUBA® formulation.

In some embodiments, the subject being treated for prostate cancer has undergone androgen deprivation therapy, undergoes androgen deprivation therapy concurrently with the HhP inhibitor treatment, or both. The goal of androgen deprivation therapy is to reduce androgen levels in the body or to prevent androgen from reaching prostate cancer cells. Examples of treatments/agents for androgen deprivation therapy that may be utilized include, but are not limited, to orchiectomy (surgical castration), luteinizing hormone-releasing hormone (LHRH) analogs (e.g., leuprolide, goserelin, triptorelin, or histrelin), luteinizing hormone-releasing hormone (LHRH) antagonists (e.g., degarelix and abiraterone), anti-androgens (flutamide, bicalutamide, nilutamide, and enzalutamide), and other androgen-suppressing drugs (e.g., ketoconazole).

In some embodiments, the proliferation disorder to be treated is basal cell carcinoma (BCC). In some embodiments, the BCC is treated by administering an HhP inhibitor such as itraconazole, or a pharmaceutically acceptable salt, prodrug, stereoisomer, or active metabolite thereof, at a dose in the range of 100 mg to 600 mg per day. In some embodiments, the BCC is treated by administering 150 mg of an HhP inhibitor such as itraconazole, or a pharmaceutically acceptable salt, prodrug, stereoisomer, or active metabolite thereof, two or more times per day. Preferably, the HhP inhibitor such as itraconazole, or a pharmaceutically acceptable salt, prodrug, stereoisomer, or active metabolite thereof, is orally administered in a SUBA® formulation. In some embodiments, the subject being treated for BCC has a tumor equal to or greater than 4 mm.

In some embodiments, the proliferation disorder to be treated is lung cancer, e.g., late stage metastatic non-squamous non-small cell lung cancer or other lung cancer. In some embodiments, the lung cancer is treated by administering an HhP inhibitor such as itraconazole, or a pharmaceutically acceptable salt, prodrug, stereoisomer, or active metabolite thereof, at a dose in the range of 100 mg to 600 mg per day. In some embodiments, the lung cancer is treated by administering 200 mg of an HhP inhibitor such as itraconazole, or a pharmaceutically acceptable salt, prodrug, stereoisomer, or active metabolite thereof, two or more times per day. Preferably, the HhP inhibitor such as itraconazole, or a pharmaceutically acceptable salt, prodrug, stereoisomer, or active metabolite thereof, is orally administered in a SUBA® formulation. Optionally, the method further comprises administration of an antifolate agent, such as pemetrexed, with or without a platinum-based agent, such as cisplatin as described in Combination Treatments. For example, without limitation, 300 mg/m$^2$-700 mg/m$^2$ of the antifolate agent and 25 mg/m$^2$-125 mg/m$^2$ of the platinum-based agent may be administered intravenously. In some embodiments, 500 mg/m$^2$ pemetrexed and 75 mg/m$^2$ cisplatin are administered intravenously.

It has been demonstrated that HhP inhibitors (e.g., itraconazole) are capable of delaying or inhibiting tumor cell growth. Using the methods of the invention, the HhP inhibitors can be administered locally at the site of a tumor (e.g., by direct injection) or remotely from the site (e.g., systemically). As used herein, the term "tumor" refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MM), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site.

Combination Treatments

According to the method of the subject invention, an HhP inhibitor can be administered to a subject by itself, or co-administered with one or more other agents such as an HhP inhibitor, or a different agent or agents. In some embodiments, the additional agent is one or more anti-cancer agents. Anti-cancer agents include but are not limited to the chemotherapeutic agents listed in Table 2.

Co-administration can be carried out simultaneously (in the same or separate formulations) or consecutively with the additional agent administered before and/or after one or more HhP inhibitors. Furthermore, HhP inhibitors can be administered to a subject as adjuvant therapy. For example, one or more HhP inhibitors can be administered to a patient in conjunction with one or more chemotherapeutic agents.

Thus, the HhP inhibitor(s), whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the HhP inhibitor, or act towards preventing any potential side effects which may be posed as a result of administration of these agents. The HhP inhibitor can be conjugated to a therapeutic agent, as well.

In some embodiments, two or more HhP inhibitors are administered to the subject simultaneously in the same or different formulations, or sequentially. The HhP inhibitors may act on the same member of the HhP, whether in similar or distinct manners, or on different members of the pathway. For example, it may be desirable to administer HhP inhibitors that inhibit the HhP pathway at different points in the pathway or by different mechanisms. For example, while both itraconazole and vismodegib target Smo, they differ in the way they bind and act on the receptor, inhibiting the HhP by different mechanisms of action. Vismodegib acts as a cylcopamine-competitive antagonist of the Smo receptor, causing the transcription factors Gli1 and Gli2 to remain inactive, which inhibits the expression of tumor mediating genes within the HhP. In contrast, itraconazole inhibits activation of the HhP by targeting Smo at a site distinct from that of cyclopamine mimics currently in development. The Smo protein can generally be activated by its translocation to the primary cilium and/or by changing its configuration. Vismodegib works on Smo effectively by ensuring that the protein does not change its configuration, whereas itraconazole works by preventing its translocation. These distinctions are supported by the ability of these two drugs to synergize. Accordingly, in some embodiments, one or more additional HhP inhibitors are administered and the additional HhP inhibitor differs from the first HhP inhibitor in its mechanism of action by which it inhibits the HhP (e.g., itraconazole, or a pharmaceutically acceptable salt, prodrug, stereoisomer, or active metabolite of itraconazole, and vismodegib, or a pharmaceutically acceptable salt, prodrug, stereoisomer, or active metabolite of vismodegib).

Additional agents that can be co-administered to target cells in vitro or in vivo, such as in a subject, in the same or as a separate formulation, include those that modify a given biological response, such as immunomodulators. The additional agents may be, for example, small molecules, polypeptides (proteins, peptides, or antibodies or antibody fragments), or nucleic acids (encoding polypeptides or inhibitory nucleic acids such as antisense oligonucleotides or interfering RNA). For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. In one embodiment, the methods and compositions of the invention incorporate one or more anti-cancer agents, such as cytotoxic agents, chemotherapeutic agents, anti-signaling agents, and anti-angiogenic agents.

As used herein, the term "anti-cancer agent" refers to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). In one embodiment, the anti-cancer agent administered before, during, or after administration of the HhP inhibitor is a different HhP inhibitor. Anti-cancer agents include but are not limited to the chemotherapeutic agents listed in Table 2.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Examples of chemotherapeutic agents that may be used in conjunction with the Hhp inhibitors are listed in Table 2. In some embodiments, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 2

| Examples of Chemotherapeutic Agents |
|---|
| 13-cis-Retinoic Acid |
| 2-Amino-6-Mercaptopurine |
| 2-CdA |
| 2-Chlorodeoxyadenosine |
| 5-fluorouracil |
| 5-FU |
| 6-TG |
| 6-Thioguanine |
| 6-Mercaptopurine |
| 6-MP |
| Accutane |
| Actinomycin-D |
| Adriamycin |

TABLE 2-continued

| Examples of Chemotherapeutic Agents |
|---|
| Adrucil |
| Agrylin |
| Ala-Cort |
| Aldesleukin |
| Alemtuzumab |
| Alitretinoin |
| Alkaban-AQ |
| Alkeran |
| All-transretinoic acid |
| Alpha interferon |
| Altretamine |
| Amethopterin |
| Amifostine |
| Aminoglutethimide |
| Anagrelide |
| Anandron |
| Anastrozole |
| Arabinosylcytosine |
| Ara-C |
| Aranesp |
| Aredia |
| Arimidex |
| Aromasin |
| Arsenic trioxide |
| Asparaginase |
| ATRA |
| Avastin |
| BCG |
| BCNU |
| Bevacizumab |
| Bexarotene |
| Bicalutamide |
| BiCNU |
| Blenoxane |
| Bleomycin |
| Bortezomib |
| Busulfan |
| Busulfex |
| C225 |
| Calcium Leucovorin |
| Campath |
| Camptosar |
| Camptothecin-11 |
| Capecitabine |
| Carac |
| Carboplatin |
| Carmustine |
| Carmustine wafer |
| Casodex |
| CCNU |
| CDDP |
| CeeNU |
| Cerubidine |
| cetuximab |
| Chlorambucil |
| Cisplatin |
| Citrovorum Factor |
| Cladribine |
| Cortisone |
| Cosmegen |
| CPT-11 |
| Cyclophosphamide |
| Cytadren |
| Cytarabine |
| Cytarabine liposomal |
| Cytosar-U |
| Cytoxan |
| Dacarbazine |
| Dactinomycin |
| Darbepoetin alfa |
| Daunomycin |
| Daunorubicin |
| Daunorubicin hydrochloride |
| Daunorubicin liposomal |
| DaunoXome |
| Decadron |
| Delta-Cortef |
| Deltasone |

TABLE 2-continued

| Examples of Chemotherapeutic Agents |
|---|
| Denileukin diftitox |
| DepoCyt |
| Dexamethasone |
| Dexamethasone acetate |
| dexamethasone sodium phosphate |
| Dexasone |
| Dexrazoxane |
| DHAD |
| DIC |
| Diodex |
| Docetaxel |
| Doxil |
| Doxorubicin |
| Doxorubicin liposomal |
| Droxia |
| DTIC |
| DTIC-Dome |
| Duralone |
| Efudex |
| Eligard |
| Ellence |
| Eloxatin |
| Elspar |
| Emcyt |
| Epirubicin |
| Epoetin alfa |
| Erbitux |
| Erwinia L-asparaginase |
| Estramustine |
| Ethyol |
| Etopophos |
| Etoposide |
| Etoposide phosphate |
| Eulexin |
| Evista |
| Exemestane |
| Fareston |
| Faslodex |
| Femara |
| Filgrastim |
| Floxuridine |
| Fludara |
| Fludarabine |
| Fluoroplex |
| Fluorouracil |
| Fluorouracil (cream) |
| Fluoxymesterone |
| Flutamide |
| Folinic Acid |
| FUDR |
| Fulvestrant |
| G-CSF |
| Gefitinib |
| Gemcitabine |
| Gemtuzumab ozogamicin |
| Gemzar |
| Gleevec |
| Lupron |
| Lupron Depot |
| Matulane |
| Maxidex |
| Mechlorethamine |
| Mechlorethamine Hydrochlorine |
| Medralone |
| Medrol |
| Megace |
| Megestrol |
| Megestrol Acetate |
| Melphalan |
| Mercaptopurine |
| Mesna |
| Mesnex |
| Methotrexate |
| Methotrexate Sodium |
| Methylprednisolone |
| Mylocel |
| Letrozole |
| Neosar |

TABLE 2-continued

| Examples of Chemotherapeutic Agents |
|---|
| Neulasta |
| Neumega |
| Neupogen |
| Nilandron |
| Nilutamide |
| Nitrogen Mustard |
| Novaldex |
| Novantrone |
| Octreotide |
| Octreotide acetate |
| Oncospar |
| Oncovin |
| Ontak |
| Onxal |
| Oprevelkin |
| Orapred |
| Orasone |
| Oxaliplatin |
| Paclitaxel |
| Pamidronate |
| Panretin |
| Paraplatin |
| Pediapred |
| PEG Interferon |
| Pegaspargase |
| Pegfilgrastim |
| PEG-INTRON |
| PEG-L-asparaginase |
| Phenylalanine Mustard |
| Platinol |
| Platinol-AQ |
| Prednisolone |
| Prednisone |
| Prelone |
| Procarbazine |
| PROCRIT |
| Proleukin |
| Prolifeprospan 20 with Carmustine implant |
| Purinethol |
| Raloxifene |
| Rheumatrex |
| Rituxan |
| Rituximab |
| Roveron-A (interferon alfa-2a) |
| -Rubex |
| Rubidomycin hydrochloride |
| Sandostatin |
| Sandostatin LAR |
| Sargramostim |
| Solu-Cortef |
| Solu-Medrol |
| STI-571 |
| Streptozocin |
| Tamoxifen |
| Targretin |
| Taxol |
| Taxotere |
| Temodar |
| Temozolomide |
| Teniposide |
| TESPA |
| Thalidomide |
| Thalomid |
| TheraCys |
| Thioguanine |
| Thioguanine Tabloid |
| Thiophosphoamide |
| Thioplex |
| Thiotepa |
| TICE |
| Toposar |
| Topotecan |
| Toremifene |
| Trastuzumab |
| Tretinoin |
| Trexall |
| Trisenox |
| TSPA |

TABLE 2-continued

| Examples of Chemotherapeutic Agents |
|---|
| VCR |
| Velban |
| Velcade |
| VePesid |
| Vesanoid |
| Viadur |
| Vinblastine |
| Vinblastine Sulfate |
| Vincasar Pfs |
| Vincristine |
| Vinorelbine |
| Vinorelbine tartrate |
| VLB |
| VP-16 |
| Vumon |
| Xeloda |
| Zanosar |
| Zevalin |
| Zinecard |
| Zoladex |
| Zoledronic acid |
| Zometa |
| Gliadel wafer |
| Glivec |
| GM-CSF |
| Goserelin |
| granulocyte—colony stimulating factor |
| Granulocyte macrophage colony stimulating factor |
| Halotestin |
| Herceptin |
| Hexadrol |
| Hexalen |
| Hexamethylmelamine |
| HMM |
| Hycamtin |
| Hydrea |
| Hydrocort Acetate |
| Hydrocortisone |
| Hydrocortisone sodium phosphate |
| Hydrocortisone sodium succinate |
| Hydrocortone phosphate |
| Hydroxyurea |
| Ibritumomab |
| Ibritumomab Tiuxetan |
| Idamycin |
| Idarubicin |
| Ifex |
| IFN-alpha |
| Ifosfamide |
| IL-2 |
| IL-11 |
| Imatinib mesylate |
| Imidazole Carboxamide |
| Interferon alfa |
| Interferon Alfa-2b (PEG conjugate) |
| Interleukin-2 |
| Interleukin-11 |
| Intron A (interferon alfa-2b) |
| Leucovorin |
| Leukeran |
| Leukine |
| Leuprolide |
| Leurocristine |
| Leustatin |
| Liposomal Ara-C |
| Liquid Pred |
| Lomustine |
| L-PAM |
| L-Sarcolysin |
| Meticorten |
| Mitomycin |
| Mitomycin-C |
| Mitoxantrone |
| M-Prednisol |
| MTC |
| MTX |
| Mustargen |
| Mustine |

TABLE 2-continued

| Examples of Chemotherapeutic Agents |
|---|
| Mutamycin |
| Myleran |
| Iressa |
| Irinotecan |
| Isotretinoin |
| Kidrolase |
| Lanacort |
| L-asparaginase |
| LCR |
| Pemetrexed |

In some embodiments, an antifolate agent (e.g., a pyrimidine-based antifolate agent), such as Pemetrexed, is administered to the subject, before, during, or after administration of the HhP inhibitor. Pemetrexed is a synthetic pyrimidine-based antifolate. Pemetrexed is also known as LY231514 and (2S)-2-{[4-[2-(2-amino-4-oxo-1,7-dihydropyrrolo[2,3-d]pyrimidin-5-yl)ethyl]benzoyl]amino}pentanedioic acid, and is marked under the brand name N-[4-2-(2-Amino-4,7-dihydro-4-oxo-1H-pyrrolo[2,3-d]pyrimidin-5-yl)ethyl]benzoyl]-1-glutamic acid disodium salt (CAS Number: 150399-23-8). Pemetrexed binds to and inhibits the enzyme thymidylate synthase (TS), which catalyzes the methylation of 2'-deoxyuridine-5'-monophosphate (dUMP) to 2'-deoxythymidine-5'-monophosphate (dTMP), an essential precursor in DNA synthesis.

In some embodiments, a platinum-based agent (coordination complex of platinum) is administered to the subject before, during, or after administration of the HhP inhibitor. As a class, platinum-based agents are believed to act by causing crosslinking of DNA as a monoadduct, interstrand crosslinks, intrastrand crosslinks, or DNA protein crosslinks, resulting in inhibited DNA repair. In some embodiments, the platinum-based agent is carboplatin, cisplatin, or oxaliplatin, satraplatin, picoplatin, nedaplatin, and triplatin.

Addition of an HhP inhibitor to a lung cancer treatment regimen including an antifolate such as pemetrexed can significantly increase the subject's survival time (see Rudin et al., "Phase 2 Study of Pemetrexed and Itraconazole as Second-Line Therapy for Metastatic Nonsquamous Non-Small-Cell Lung Cancer," J. Thorac. Oncol., 2013, 8(5): 619-623, which is incorporated herein by reference in its entirety). In some embodiments of the methods of the invention, the proliferation disorder to be treated is non-squamous NSCLC and the subject is orally administered a SUBA® formulation of itraconazole (e.g., 100 mg to 600 mg per day of a SUBA® formulation), or a pharmaceutically acceptable salt, prodrug, stereoisomer, or active metabolite thereof, two or more times per day. Optionally, the subject is also administered an antifolate agent, such as pemetrexed, with or without a platinum-based agent, such as cisplatin by any appropriate route. For example, without limitation, 300 mg/m$^2$-700 mg/m$^2$ of the antifolate agent and 25 mg/m$^2$-125 mg/m$^2$ of the platinum-based agent may be administered intravenously. In some embodiments, 500 mg/m$^2$ pemetrexed and 75 mg/m$^2$ cisplatin are administered intravenously.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Experimental controls are considered fundamental in experiments designed in accordance with the scientific method. It is routine in the art to use experimental controls in scientific experiments to prevent factors other than those being studied from affecting the outcome.

All patents, patent applications, provisional applications, and publications referred to or cited herein, supra or infra, are incorporated by reference in their entirety, including all figures and tables, to the extent they are not inconsistent with the explicit teachings of this specification.

EXEMPLIFIED EMBODIMENTS

Embodiment 1

A method for treating a proliferation disorder in a subject, comprising administering a composition comprising a Hedgehog pathway (HhP) inhibitor to the subject, wherein the composition is administered in an effective amount to achieve a plasma trough level of at least about 1,000 ng/mL of the HhP inhibitor.

Embodiment 2

The method of embodiment 1, wherein the HhP inhibitor comprises itraconazole, or a pharmaceutically acceptable salt, prodrug, stereoisomer, or active metabolite thereof.

Embodiment 3

The method of embodiment 2, wherein the composition comprises a SUBA® formulation of itraconazole, or a pharmaceutically acceptable salt, prodrug, stereoisomer, or active metabolite thereof; and wherein the SUBA® formulation is orally administered at a dose in the range of 100 mg to 600 mg itraconazole per day.

Embodiment 4

The method of embodiment 2, wherein the HhP inhibitor therapy comprises administration of a capsule or powder of 50 mg of the itraconazole, or a pharmaceutically acceptable salt, prodrug, stereoisomer, or active metabolite thereof, twice per day.

Embodiment 5

The method of embodiment 2, wherein the SUBA® formulation is a SUBA-CAP™ formulation.

Embodiment 6

The method of any preceding embodiment, wherein the composition is administered in an effective amount to achieve a plasma trough level of at least 1,000 ng/mL of the HhP inhibitor.

Embodiment 7

The method of any preceding embodiment, wherein the composition is administered in an effective amount to achieve a plasma trough level of at least about 1,000 ng/mL of the HhP inhibitor after about 4 weeks of initiation of treatment with the HhP inhibitor.

Embodiment 8

The method of any preceding embodiment, wherein the composition is administered in an effective amount to achieve a plasma trough level of at least about 1,000 ng/mL of the HhP inhibitor within about 2 weeks after initiation of treatment, and to maintain the plasma trough level of at least about 1,000 ng/mL of the HhP inhibitor for the duration of the treatment.

Embodiment 9

The method of any preceding embodiment, further comprising measuring the plasma level of the HhP inhibitor, or a metabolite thereof, in the subject one or more times.

Embodiment 10

The method of embodiment 9, wherein said measuring is carried out one or more times about 4 weeks after initiation of treatment with the HhP inhibitor.

Embodiment 11

The method of any preceding embodiment, further comprising measuring the plasma level of the HhP inhibitor, or a metabolite thereof, one or more times in a period of time from about 4 weeks to about 12 weeks.

Embodiment 12

The method of embodiment 11, further comprising increasing a subsequent dose of the HhP inhibitor if the plasma trough level of at least about 1,000 ng/mL of the HhP inhibitor is not maintained.

Embodiment 13

The method of embodiment 11, further comprising reducing a subsequent dose of an HhP inhibitor if the plasma trough level at about 4 weeks is at least 1000 ng/mL and the patient is experiencing one or more side effects.

Embodiment 14

The method of any preceding embodiment, wherein the HhP inhibitor is administered at least once daily.

Embodiment 15

The method of any preceding embodiment, wherein the HhP inhibitor is administered at least twice daily.

Embodiment 16

The method of any preceding embodiment, wherein the proliferation disorder is cancer.

Embodiment 17

The method of embodiment 16, wherein the cancer is lung cancer.

Embodiment 18

The method of embodiment 16, wherein the cancer is basal cell carcinoma (BCC).

Embodiment 19

The method of embodiment 16, wherein the cancer is prostate cancer.

Embodiment 20

The method of embodiment 16, wherein the cancer is prostate cancer and said method further comprises comparing the level of prostate-specific antigen (PSA) in a sample obtained from the subject following administration of the HhP inhibitor with a reference level of PSA, and wherein the level of PSA in the sample compared to the reference level of PSA is prognostic for an outcome of treatment with the HhP inhibitor.

Embodiment 21

The method of embodiment 20, wherein a PSA level increase of less than about 25% relative to the PSA level at initiation of HhP inhibitor treatment is indicative of efficacy and a PSA level increase of about 25% or greater is indicative of a lack of efficacy.

Embodiment 22

The method of embodiment 20 or 21, wherein the sample is obtained from the subject within 4 to 12 weeks after initiation of HhP inhibitor therapy.

Embodiment 23

The method of embodiment 20 or 21, wherein the method further comprises obtaining the sample from the subject after said administering.

Embodiment 24

The method of embodiment 20 or 21, wherein the method further comprises maintaining HhP inhibitor therapy if the measured level of PSA is indicative of efficacy.

Embodiment 25

The method of embodiment 20 or 21, wherein the method further comprises ceasing treatment with the HhP inhibitor if the measured level of PSA is indicative of a lack of efficacy.

Embodiment 26

The method of embodiment 25, further comprising administering a treatment for the prostate cancer other than an HhP inhibitor.

Embodiment 27

The method of embodiment 25, wherein the treatment comprises one or more from among radiation therapy, hormone therapy, chemotherapy, immunotherapy, surgery, cryosurgery, high-intensity focused ultrasound, and proton beam radiation therapy.

Embodiment 28

The method of embodiment 20 or 21, wherein the method further comprises increasing the dose of the HhP inhibitor and/or frequency of dose of the HhP inhibitor if the measured level of PSA is indicative of a lack of efficacy.

Embodiment 29

The method of embodiment 20 or 21, wherein the method further comprises decreasing the dose of the HhP inhibitor and/or frequency of dose of the HhP inhibitor if the measured level of PSA is indicative of efficacy but the subject is experiencing one or more adverse effects.

Embodiment 30

The method of embodiment 20 or 21, wherein the PSA level is the level of total PSA (free (unbound) PSA and bound PSA).

Embodiment 31

The method of embodiment 20 or 21, wherein the PSA level is PSA doubling time.

Embodiment 32

The method of embodiment 20 or 21, wherein PSA protein level is measured.

Embodiment 33

The method of embodiment 32, wherein the PSA protein level is measured by radioimmunoassay (MA), immunoradiometric assay (IRMA), enzyme-linked immunosorbent assay (ELISA), dot blot, slot blot, enzyme-linked immunosorbent spot (ELISPOT) assay, Western blot, peptide microarray, surface plasmon resonance, fluorescence resonance energy transfer, bioluminescence resonance energy transfer, fluorescence quenching fluorescence, fluorescence polarization, mass spectrometry (MS), high-performance liquid chromatography (HPLC), high-performance liquid chromatography/mass spectrometry (HPLC/MS), high-performance liquid chromatography/mass spectrometry/mass spectrometry (HPLC/MS/MS), capillary electrophoresis, rod-gel electrophoresis, or slab-gel electrophoresis.

Embodiment 34

The method of embodiment 20 or 21, wherein PSA DNA or mRNA level is measured.

Embodiment 35

The method of embodiment 34, wherein the PSA mRNA level is measured by Northern blot, Southern blot, nucleic acid microarray, polymerase chain reaction (PCR), real time-PCR (RT-PCR), nucleic acid sequence based amplification assay (NASBA), or transcription mediated amplification (TMA).

Embodiment 36

The method of embodiment 20 or 21, wherein PSA activity level is measured.

Embodiment 37

The method of embodiment 20 or 21, wherein the sample is a serum sample.

Embodiment 38

The method of any one of embodiments 20 to 37, wherein the method further comprises obtaining the sample from the subject.

Embodiment 39

The method of any preceding embodiment, further comprising monitoring the proliferation disorder in the subject, wherein a lack of clinical response in the proliferation disorder to the treatment is indicative that the plasma trough level of the HhP inhibitor should be increased further above about 1000 ng/mL, and wherein the occurrence of a clinical response and a plasma trough level of the HhP inhibitor substantially higher than about 1000 ng/mL indicates that one or more subsequent doses of the HhP inhibitor can be reduced.

Embodiment 40

The method of any preceding embodiment, further comprising monitoring the proliferation disorder in the subject, wherein a lack of clinical response in the proliferation disorder to the treatment, after about four weeks of said administering, is indicative of a need to increase the dose, and/or frequency of the dose, of the HhP inhibitor.

Embodiment 41

The method of any preceding embodiment, further comprising monitoring the proliferation disorder in the subject, wherein the occurrence of a clinical response in the proliferation disorder to the treatment, after about four weeks of said administering, is indicative of a need to decrease the dose, and/or frequency of the dose, of the HhP inhibitor.

Embodiment 42

The method of any one of embodiments 39-41, wherein said monitoring comprises visual inspection, palpation, imaging, assaying the presence, level, or activity of one or more biomarkers associated with the proliferation disorder in a sample obtained from the subject, or a combination of two or more of the foregoing.

Embodiment 43

The method of embodiment 42, wherein the one or more biomarkers comprise Gli1, Gli2, Gli3, or a combination of two or more of the foregoing.

Embodiment 44

The method of any one of embodiments 39-43, wherein said monitoring comprises monitoring at least one of the following parameters: tumor size, rate of change in tumor size, hedgehog levels or signaling, appearance of a new tumor, rate of appearance of new tumors, change in a symptom of the proliferation disorder, appearance of a new symptom associated with the proliferation disorder, quality of life (e.g., amount of pain associated with the proliferation disorder), or a combination of two or more of the foregoing.

Embodiment 45

The method of embodiment 20 or 21, wherein the method further comprises monitoring the PSA level in the subject, comprising comparing the PSA level in multiple samples with the reference level of PSA, wherein the samples are obtained from the subject over time, following HhP inhibitor treatment.

Embodiment 46

The method of any preceding embodiment, further comprising administering eplerenone or other mineralocorticoid inhibitor, or pemetrexed or other antifolate, or cisplatin or other platinum-based chemotherapeutic agent, or a combination of two or more of the foregoing, to the subject.

Embodiment 47

The method of embodiment 46, wherein the subject is suffering from an adverse effect selected from hypertension, peripheral edema, and hypokalemia, and wherein the mineralocorticoid inhibitor is administered in an amount effective to treat the adverse effect.

Embodiment 48

The method of any preceding embodiment, wherein the HhP inhibitor is a purified stereoisomer of itraconazole (non-racemic mixture), or an itraconazole analogue in which the sec-butyl side chain has been replaced with one or more moieties, relative to itraconazole.

Embodiment 49

The method of any preceding embodiment, wherein the subject has a fungal infection.

Embodiment 50

The method of any one of embodiments 1 to 48, wherein the subject does not have a fungal invention.

Embodiment 51

The method of any one of embodiments 1 to 49, wherein the subject has a fungal infection selected from Blastomycosis, Histoplasmosis, Candidiasis, and Aspergillosis.

Embodiment 52

The method of any one of embodiments 1 to 48, wherein the subject does not have a fungal infection selected from among Blastomycosis, Histoplasmosis, Candidiasis, and Aspergillosis.

Embodiment 53

The method of any preceding embodiment, wherein the subject has received no prior chemotherapy to treat the proliferation disorder.

Embodiment 54

The method of any preceding embodiment, wherein the subject is administered no steroid during the duration of the treatment.

Embodiment 55

The method of any preceding embodiment, wherein the subject is administered no agent that interacts with CYP3A4 during the duration of the treatment.

Embodiment 56

The method of any preceding embodiment, wherein the duration of treatment with the HhP inhibitor is in the range of about 4 weeks to about 24 weeks.

Embodiment 57

The method of any preceding embodiment, wherein the HhP inhibitor targets the Smoothened protein of the HhP pathway.

Embodiment 58

The method of any preceding embodiment, wherein the HhP inhibitor is cyclopamine-competitive.

Embodiment 59

The method of any preceding embodiment wherein the HhP inhibitor is cyclopamine-competitive and the proliferation disorder comprises prostate cancer.

Embodiment 60

The method of embodiment 59, wherein the proliferation disorder is prostate cancer and said method further comprises comparing the level of prostate-specific antigen (PSA) in a sample obtained from the subject following administration of the HhP inhibitor with a reference level of PSA, and wherein the level of PSA in the sample compared to the reference level of PSA is prognostic for an outcome of treatment with the HhP inhibitor.

Embodiment 61

The method of embodiment 60, wherein a PSA level increase of less than about 25% relative to the PSA level at initiation of HhP inhibitor treatment is indicative of efficacy and a PSA level increase of about 25% or greater is indicative of a lack of efficacy.

Embodiment 62

A method of prognosticating an outcome of prostate cancer treatment with a Hedgehog pathway (HhP) inhibitor therapy in a subject, comprising comparing the level of prostate-specific antigen (PSA) in a sample obtained from the subject following HhP inhibitor therapy with a reference level of PSA, wherein the level of PSA in the sample compared to the reference level of PSA is prognostic for an outcome of treatment with the HhP inhibitor.

Embodiment 63

The method of embodiment 62, wherein the reference level is the PSA level in the subject at initiation of HhP inhibitor therapy.

Embodiment 64

A method of determining the efficacy of Hedgehog pathway (HhP) inhibitor therapy for prostate cancer in a human subject, comprising measuring prostate-specific antigen (PSA) level in a sample obtained from the subject following initiation of HhP inhibitor therapy, wherein a measured PSA level compared to a first reference PSA level at initiation of HhP inhibitor therapy is indicative of efficacy, and wherein a measured PSA level compared to a second reference PSA level is indicative of a lack of efficacy.

Embodiment 65

The method of embodiment 62 or 64, wherein a PSA level increase of less than about 25% relative to the PSA level at initiation of HhP inhibitor therapy is indicative of efficacy and a PSA level increase of about 25% or greater is indicative of a lack of efficacy.

Embodiment 66

The method of embodiment 62 or 64, wherein the HhP inhibitor is orally administered in an effective amount to achieve a plasma trough level of at least about 1,000 ng/mL of the HhP inhibitor.

Embodiment 67

The method of embodiment 62 or 64, wherein the HhP inhibitor is orally administered in an effective amount to achieve a plasma trough level of at least 1,000 ng/mL of the HhP inhibitor.

Embodiment 68

The method of embodiment 62 or 64, wherein the HhP inhibitor therapy comprises oral administration of the HhP inhibitor at a dose in the range of 100 mg to 600 mg per day.

Embodiment 69

The method of embodiment 62 or 64, wherein the HhP inhibitor targets the Smoothened protein of the HhP pathway.

Embodiment 70

The method of embodiment 62 or 64, wherein the HhP inhibitor is cyclopamine-competitive.

Embodiment 71

The method of embodiment 62 or 64, wherein the HhP inhibitor comprises itraconazole, or a pharmaceutically acceptable salt, prodrug, stereoisomer, or active metabolite thereof.

Embodiment 72

The method of embodiment 62 or 64, wherein the HhP inhibitor comprises a SUBA® formulation (e.g., a SUBA-CAP™ formulation) of itraconazole.

Embodiment 73

The method of embodiment 62 or 64, wherein the HhP inhibitor comprises a SUBA® formulation of itraconazole, and wherein the HhP inhibitor therapy comprises administration of the SUBA® formulation at a dose or itraconazole in the range of 100 mg to 600 mg per day.

Embodiment 74

The method of any one of embodiments 71-73, wherein the HhP inhibitor therapy comprises administration of a capsule or powder of 50 mg of the HhP inhibitor twice per day.

Embodiment 75

The method of any preceding embodiment, wherein the HhP inhibitor therapy comprises administration of the HhP inhibitor intravenously or locally (e.g., by direct injection) at the site of a prostate cancer lesion or tumor.

Embodiment 76

The method of embodiment 62 or 64, wherein the sample is obtained from the subject within 4 to 12 weeks after initiation of HhP inhibitor therapy.

Embodiment 77

The method of embodiment 62 or 64, wherein the method further comprises administering the HhP inhibitor to the subject, and obtaining the sample from the subject after said administering.

Embodiment 78

The method of embodiment 62 or 64, wherein the method further comprises maintaining HhP inhibitor therapy if the measured level of PSA is indicative of efficacy.

Embodiment 79

The method of embodiment 62 or 64, wherein the method further comprises withholding HhP inhibitor therapy if the measured level of PSA is indicative of a lack of efficacy.

Embodiment 80

The method of embodiment 79, further comprising administering a treatment for the prostate cancer other than an HhP inhibitor.

Embodiment 81

The method of embodiment 80, wherein the treatment comprises one or more from among radiation therapy, hormone therapy, chemotherapy, immunotherapy, surgery, cryosurgery, high-intensity focused ultrasound, and proton beam radiation therapy.

Embodiment 82

The method of embodiment 62 or 64, wherein the method further comprises increasing the dose of the HhP inhibitor and/or frequency of dose of the HhP inhibitor if the measured level of PSA is indicative of a lack of efficacy.

Embodiment 83

The method of embodiment 62 or 64, wherein the method further comprises decreasing the dose of the HhP inhibitor and/or frequency of dose of the HhP inhibitor if the measured level of PSA is indicative of efficacy but the subject is experiencing one or more side effects

Embodiment 84

The method of embodiment 62 or 64, wherein the PSA level is the level of total PSA (free (unbound) PSA and bound PSA).

Embodiment 85

The method of embodiment 62 or 64, wherein the PSA level is PSA doubling time.

Embodiment 86

The method of embodiment 62 or 64, wherein PSA protein level is measured.

Embodiment 87

The method of embodiment 86, wherein the PSA protein level is measured by radioimmunoassay (MA), immunoradiometric assay (IRMA), enzyme-linked immunosorbent assay (ELISA), dot blot, slot blot, enzyme-linked immunosorbent spot (ELISPOT) assay, Western blot, peptide microarray, surface plasmon resonance, fluorescence resonance energy transfer, bioluminescence resonance energy transfer, fluorescence quenching fluorescence, fluorescence polarization, mass spectrometry (MS), high-performance liquid chromatography (HPLC), high-performance liquid chromatography/mass spectrometry (HPLC/MS), high-performance liquid chromatography/mass spectrometry/mass spectrometry (HPLC/MS/MS), capillary electrophoresis, rod-gel electrophoresis, or slab-gel electrophoresis.

Embodiment 88

The method of embodiment 62 or 64, wherein PSA DNA or mRNA level is measured.

Embodiment 89

The method of embodiment 88, wherein the PSA mRNA level is measured by Northern blot, Southern blot, nucleic acid microarray, polymerase chain reaction (PCR), real time-PCR (RT-PCR), nucleic acid sequence based amplification assay (NASBA), or transcription mediated amplification (TMA).

Embodiment 90

The method of embodiment 62 or 64, wherein PSA activity level is measured.

Embodiment 91

The method of embodiment 62 or 64, wherein the sample is a serum sample.

Embodiment 92

The method of embodiment 62 or 64, wherein the method further comprises obtaining the sample from the subject.

Embodiment 93

The method of embodiment 62, wherein the method comprises monitoring the PSA level in the subject, comprising comparing the PSA level in multiple samples with the reference level of PSA, wherein the samples are obtained from the subject over time, following HhP inhibitor therapy.

Embodiment 94

The method of embodiment 64, wherein the method comprises monitoring the PSA level in the subject, comprising measuring the PSA level in multiple samples obtained from the subject over time, following HhP inhibitor therapy.

Embodiment 95

A method for treating prostate cancer in a subject, comprising administering Hedgehog pathway (HhP) inhibitor therapy to the subject; and carrying out the method of any one of embodiments 62 to 94.

Embodiment 96

A method for determining a dose of HhP inhibitor suitable for administration to a subject for treatment of prostate cancer, comprising measuring a PSA level in a sample obtained from the subject; and determining an effective dose of HhP inhibitor based on comparison of the measured PSA level to a reference level of PSA.

Embodiment 97

The method of embodiment 95 or 96, wherein the HhP inhibitor is cyclopamine-competitive.

Embodiment 98

The method of any preceding embodiment, wherein the proliferation disorder is prostate cancer, wherein the composition comprises a SUBA® formulation of itraconazole, or a pharmaceutically acceptable salt, prodrug, stereoisomer, or active metabolite thereof, and wherein the SUBA® formulation is orally administered at a dose in the range of 100 mg to 600 mg per day.

Embodiment 99

The method of embodiment 18, wherein the composition comprises a SUBA® formulation of itraconazole, or a pharmaceutically acceptable salt, prodrug, stereoisomer, or active metabolite thereof, and wherein the SUBA® formulation is orally administered at a dose in the range of 100 mg to 600 mg per day.

Embodiment 100

The method of embodiment 17, wherein the composition comprises a SUBA® formulation of itraconazole, or a pharmaceutically acceptable salt, prodrug, stereoisomer, or active metabolite thereof, wherein the SUBA® formulation is orally administered at a dose in the range of 100 mg to 600 mg per day, and wherein the method further comprises administering an antifolate and a platinum-based chemotherapeutic agent to the subject.

Embodiment 101

The method of embodiment 1, further comprising monitoring the proliferation disorder in the subject, wherein a lack of clinical response in the proliferation disorder to the treatment, after about four weeks of said administering, is indicative of a need to increase the dose of the HhP inhibitor, or increase the frequency of the dose of the HhP inhibitor, or administer an additional HhP inhibitor that inhibits the HhP by a different mechanism than the previously administered HhP inhibitor, or a combination of two or more of the foregoing.

Embodiment 102

The method of embodiment 1, 62, 64, 95, or 96, wherein the HhP inhibitor is cyclopamine-competitive.

Embodiment 103

The method of embodiment 1, 62, 64, 95, or 96, wherein the HhP inhibitor is non-cyclopamine-competitive.

Embodiment 104

The method of embodiment 1, further comprising, prior to said administering, selecting the subject for treatment, wherein said selecting comprises:
measuring a biomarker in a sample obtained from the subject, wherein the biomarker is directly or indirectly representative of HhP signaling, and
comparing the measured biomarker level to a reference level to determine the presence or absence of elevated HhP signaling, wherein the presence of elevated HhP signaling indicates that the subject should be treated.

Embodiment 105

The method of embodiment 104, wherein the biomarker is an HhP ligand or a glioma-associated oncogene homolog (Gli) transcription factor (e.g., Sonic hedgehog (SHH), desert hedgehog (DHH), Indian hedgehog (DHH), Gli1, Gli2, Gli3, or a combination or two or more of the foregoing).

Embodiment 106

The method of embodiment 1, further comprising monitoring the proliferation disorder in the subject, wherein said monitoring comprises:
measuring a biomarker in a sample obtained from the subject after said administering, wherein the biomarker is directly or indirectly representative of HhP signaling, and
comparing the measured biomarker level to a reference level to determine whether HhP signaling has increased, decreased, or has not changed after said comparing, wherein an increase or no change in HhP signaling indicates a need to modify the treatment by increasing the dose of the HhP inhibitor, or increasing the frequency of the dosing of the HhP inhibitor, or administering an additional HhP inhibitor before, during or after the currently administered HhP inhibitor, or a combination of two or more of the foregoing;

and wherein a decrease in HhP signaling indicates that the HhP inhibitor dose, frequency of HhP inhibitor dose, and choice of HhP inhibitor currently being administered are satisfactory and may proceed.

Embodiment 107

The method of embodiment 106, wherein the additional HhP inhibitor and HhP inhibitor currently being administered inhibit the HhP by different mechanisms of action.

Embodiment 108

The method of embodiment 107, wherein the biomarker is an HhP ligand or a glioma-associated oncogene homolog (Gli) transcription factor (e.g., Sonic hedgehog (SHH), desert hedgehog (DHH), Indian hedgehog (DHH), Gli1, Gli2, Gli3, or a combination of two or more of the foregoing).

Definitions

In order that the present disclosure may be more readily understood, certain terms are first defined. Additional definitions are set forth throughout the detailed description.

As used herein, the term "plasma trough level" refers to the concentration of an agent (e.g., a HhP inhibitor) in plasma immediately before the next dose, or the minimum concentration of the agent between two doses.

As used herein, the terms "proliferation disorder", "cell proliferation disorder", "proliferative disorder", "cell proliferative disorder", "condition characterized by undesirable cell proliferation", and grammatical variations thereof refer to any pathological or non-pathological physiological condition characterized by aberrant or undesirable proliferation of at least one cell, including but not limited to conditions characterized by undesirable or unwanted or aberrant cell proliferation, conditions characterized by undesirable or unwanted or aberrant cell survival, and conditions characterized by deficient or aberrant apoptosis. The term "cell proliferation" and grammatical variations thereof, is understood to encompass both an increase in the number of cells as a result of cell division, as well as an increase in the total mass of cells as a result of cell growth, e.g., by growth of daughter cells after mitosis. An example of a proliferation disorder is cancer, e.g., undesirable or unwanted or aberrant proliferation and survival of cancer cells such as cells associated with prostate cancer, lymphoma, myeloma, sarcoma, leukemia, or other neoplastic disorders disclosed elsewhere herein and known to one of skill in the art. Proliferation disorders include pre-cancerous or pre-malignant conditions (e.g., morphologically identifiable lesions that precede invasive cancers), intraepithelial neoplasia (e.g., prostatic IEN and cervical IEN), atypical adenomatous hyperplasia, colorectal polyps, basal cell nevus syndrome, actinic keratosis, Barrett's esophagus, atrophic gastritis, and cervical dysplasia. Examples of non-cancerous proliferation disorders include smooth muscle cell proliferation, systemic sclerosis, cirrhosis of the liver, adult respiratory distress syndrome, idiopathic cardiomyopathy, lupus erythematosus, retinopathy, (e.g., diabetic retinopathy or other retinopathies), cardiac hyperplasia, reproductive system associated disorders such as benign prostatic hyperplasia and ovarian cysts, pulmonary fibrosis, endometriosis, fibromatosis, hamartomas, lymphangiomatosis, sarcoidosis and desmoid tumors. Non-cancerous proliferation disorders also include hyperproliferation of cells in the skin such as psoriasis and its varied clinical forms, Reiter's syndrome, *pityriasis rubra pilaris*, hyper-proliferative variants of disorders of keratinization (e.g., actinic keratosis, senile keratosis), scleroderma, seborrheic keratoses, intraepidermal nevi, common warts, benign epithelial tumors, and the like.

The terms "cancer" and "malignancy" are used herein interchangeably to refer to or describe the physiological condition in mammals that is typically characterized by unregulated cell growth. The term encompasses dysplasia, carcinoma in situ (CIS), and carcinoma. The cancer may be metastatic or non-metastatic.

As used herein, the term "prostate cancer" refers to cancer or pre-cancer of the prostate, including adenocarcinoma and small cell carcinoma. The term encompasses prostatic intra-epithelial neoplasia (PIN) and carcinoma in situ of the prostate. Typically, the prostate cancer will be one that exhibits elevated expression of a Hedgehog pathway member or ligand (i.e., a Hedgehog pathway-associated cancer). The prostate cancer may be metastatic or non-metastatic. The prostate cancer may be castration-resistant or non-castration resistant. In some embodiments, the prostate cancer is metastatic, castration-resistant prostate cancer. In some embodiments, the prostate cancer is non-metastatic, castration-resistant prostate cancer.

As used herein, the term "Gli" refers to any one of the Gli1, Gli2 or Gli3 proteins, or a combination of two or more of the foregoing. "gli" refers to the nucleic acid encoding the Gli proteins, and gli1, gli2 and gli3 are the genes encoding the Gli1, Gli2 and Gli3 proteins.

As used herein, the articles "a" and "an" refer to one or to more than one (e.g., to at least one) of the grammatical object of the article. For example, "an HhP inhibitor" encompasses one or more HhP inhibitors, "a sample" encompasses one or more samples, etc.

As used herein, the term "or" is used herein to mean, and is used interchangeably with, the term "and/or", unless context clearly indicates otherwise.

As used herein, the terms "about" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, the terms "patient", "subject", and "individual" are used interchangeably and are intended to include males of the human and non-human animal species. For example, the subject may be a human or an animal model.

As used herein, and unless otherwise specified, the terms "treat," "treating" and "treatment" contemplate an action that occurs while a subject has cancer (as therapy), or before the subject has cancer (as prophylaxis), which reduces the severity of the cancer, retards or slows the progression of the cancer, or prevents the cancer. Thus treatment with HhP inhibitors may prevent or manage cancer.

As used herein, unless otherwise specified, the terms "prevent," "preventing", and "prevention" contemplate an action that occurs before a subject begins to suffer from the regrowth of the cancer and/or which inhibits or reduces the severity of the cancer, or delays its onset.

As used herein, and unless otherwise specified, the terms "manage," "managing" and "management" encompass preventing the recurrence of the cancer in a subject who has already suffered from the cancer, and/or lengthening the time that a subject who has suffered from the cancer remains in remission. The terms encompass modulating the threshold, development and/or duration of the cancer, or changing the way that a patient responds to the cancer.

As used herein, and unless otherwise specified, a "therapeutically effective amount" of a compound (e.g., an HhP inhibitor) is an amount sufficient to provide a therapeutic benefit in the treatment or management of the proliferation disorder (e.g., cancer), or to delay or minimize one or more symptoms associated with the proliferation disorder. A therapeutically effective amount of a compound means an amount of therapeutic agent, alone or in combination with other therapeutic agents, which provides a therapeutic benefit in the treatment or management of the proliferation disorder. The term "therapeutically effective amount" can encompass an amount that improves overall therapy, reduces or avoids symptoms or causes of the proliferation disorder, or enhances the therapeutic efficacy of another therapeutic agent.

As used herein, and unless otherwise specified, a "prophylactically effective amount" of a compound (e.g., a HhP inhibitor) is an amount sufficient to prevent regrowth of the proliferation disorder (e.g., cancer), or one or more symptoms associated with the proliferation disorder, or prevent its recurrence. A prophylactically effective amount of a compound means an amount of the compound, alone or in combination with other therapeutic agents, which provides a prophylactic benefit in the prevention of the proliferation disorder. The term "prophylactically effective amount" can encompass an amount that improves overall prophylaxis or enhances the prophylactic efficacy of another prophylactic agent.

As used herein, the term "efficacy" in the context of HhP inhibitory therapy refers to the ability of the therapy (as monotherapy or in combination therapy with another HhP inhibitor or other agent that is not an HhP inhibitor) to alleviate one or more symptoms of the proliferation disorder (e.g., cancer), diminish the extent of disease, stabilize (i.e., not worsening) the state of the disease, delay or slow disease progression, amelioration or palliation of the disease state, remission (whether partial or total), whether detectable or undetectable, tumor regression, inhibit tumor growth, inhibit tumor metastasis, reduce cancer cell number, inhibit cancer cell infiltration into peripheral organs, increase progression free survival, improve progression free survival, improve time to disease progression (TTP), improve response rate (RR), prolonged overall survival (OS), prolong time-to-next-treatment (TNTT), or prolong time from first progression to next treatment, or a combination of two or more of the foregoing.

As used herein, the terms "anticancer agent," "conventional anticancer agent," or "cancer therapeutic drug" refer to any therapeutic agents (e.g., chemotherapeutic compounds and/or molecular therapeutic compounds), radiation therapies, or surgical interventions, used in the treatment of cancer (e.g., in mammals). HhP inhibitors may be administered with a therapeutic agent, such as an anticancer agent.

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

As used herein, the term "solvate" refers to an HhP inhibitor having either a stoichiometric or non-stoichiometric amount of a solvent associated with the compound. The solvent can be water (i.e., a hydrate), and each molecule of inhibitor can be associated with one or more molecules of water (e.g., monohydrate, dihydrate, trihydrate, etc.). The solvent can also be an alcohol (e.g., methanol, ethanol, propanol, isopropanol, etc.), a glycol (e.g., propylene glycol), an ether (e.g., diethyl ether), an ester (e.g., ethyl acetate), or any other suitable solvent. The hedgehog inhibitor can also exist as a mixed solvate (i.e., associated with two or more different solvents).

We claim:

1. A method for treating prostate cancer in a subject that has undergone androgen deprivation therapy, is concurrently undergoing androgen deprivation therapy, or both, comprising orally administering a composition comprising a solid dispersion of a Hedgehog pathway (HhP) inhibitor and a polycarboxylic acid polymer, to the subject, wherein the HhP inhibitor comprises itraconazole, or a pharmaceutically acceptable salt, prodrug, stereoisomer, or active metabolite thereof, and wherein: (a) the composition is orally administered in an effective amount to achieve a plasma trough level of at least about 1,000 ng/mL of the HhP inhibitor, or (b) the composition is orally administered at a dose in the range of 100 mg to 600 mg HhP inhibitor per day.

2. The method of claim 1, wherein the HhP inhibitor comprises itraconazole, or a pharmaceutically acceptable salt or stereoisomer thereof.

3. The method of claim 1, wherein the composition is orally administered at a dose in the range of 100 mg to 600 mg of HhP inhibitor per day.

4. The method of claim 2, wherein said orally administering comprises oral administration of a capsule or powder of 50 mg of the itraconazole, or a pharmaceutically acceptable salt or stereoisomer thereof twice per day.

5. The method of claim 3, wherein the composition is in the form of a capsule.

6. The method of claim 1, wherein the composition is orally administered in an effective amount to achieve a plasma trough level of at least 1,000 ng/mL of the HhP inhibitor.

7. The method of claim 1, wherein the composition is administered in an effective amount to achieve a plasma trough level of at least about 1,000 ng/mL of the HhP inhibitor after about 4 weeks of initiation of treatment with the HhP inhibitor.

8. The method of claim 1, wherein the composition is administered in an effective amount to achieve a plasma trough level of at least about 1,000 ng/mL of the HhP inhibitor within about 2 weeks after initiation of treatment, and to maintain the plasma trough level of at least about 1,000 ng/mL of the HhP inhibitor for the duration of the treatment.

9. The method of claim 1, further comprising measuring the plasma level of the HhP inhibitor, or a metabolite thereof, in the subject one or more times.

10. The method of claim 9, wherein said measuring is carried out one or more times about 4 weeks after initiation of treatment with the HhP inhibitor.

11. The method of claim 1, further comprising measuring the plasma level of the HhP inhibitor, or a metabolite thereof, one or more times in a period of time from about 4 weeks to about 12 weeks.

12. The method of claim 11, further comprising increasing a subsequent dose of the HhP inhibitor if the plasma trough level of at least about 1,000 ng/mL of the HhP inhibitor is not maintained.

13. The method of claim 11, further comprising reducing a subsequent dose of an HhP inhibitor if the plasma trough level at about 4 weeks is at least 1000 ng/mL and the patient is experiencing one or more side effects.

14. The method of claim 1, wherein the prostate cancer is metastatic, castration-resistant prostate cancer.

15. The method of claim 1, further comprising measuring the level of prostate-specific antigen (PSA) in a sample obtained from the subject and determining PSA doubling time.

16. The method of claim 1, further comprising monitoring the proliferation disorder in the subject, wherein a lack of clinical response in the proliferation disorder to the treatment is indicative that the plasma trough level of the HhP inhibitor should be increased further above about 1000 ng/mL, and wherein the occurrence of a clinical response and a plasma trough level of the HhP inhibitor substantially higher than about 1000 ng/mL indicates that one or more subsequent doses of the HhP inhibitor can be reduced.

17. The method of claim 1, further comprising monitoring the proliferation disorder in the subject, wherein a lack of clinical response in the proliferation disorder to the treatment, after about four weeks of said administering, is indicative of a need to increase the dose of the HhP inhibitor, or increase the frequency of the dose of the HhP inhibitor, or administer an additional HhP inhibitor that inhibits the HhP by a different mechanism than the previously administered HhP inhibitor, or a combination of two or more of the foregoing.

18. The method of claim 1, wherein the prostate cancer is non-metastatic castration-resistant prostate cancer.

19. The method of claim 1, further comprising administering docetaxel to the subject.

20. The method of claim 1, further comprising administering prednisone or prednisolone to the subject.

* * * * *

UNITED STATES PATENT AND TRADEMARK OFFICE
CERTIFICATE OF CORRECTION

PATENT NO. : 10,363,252 B2  
APPLICATION NO. : 15/966844  
DATED : July 30, 2019  
INVENTOR(S) : Nicholas J. Virca and Francis E. O'Donnell, Jr.

Page 1 of 1

It is certified that error appears in the above-identified patent and that said Letters Patent is hereby corrected as shown below:

In the Specification

Column 3,
Line 12, "<1=25%" should read --</=25%--.

Column 6,
Line 57, "(MA)," should read --(RIA),--.

Column 14,
Line 11, "(MM)," should read --(MRI),--.

Column 18,
Line 19, "(MA)," should read --(RIA),--.

Column 21,
Line 9, "(MA)," should read --(RIA),--.

Column 52,
Line 31, "(MA)," should read --(RIA),--.

Signed and Sealed this
Fourth Day of August, 2020

Andrei Iancu
*Director of the United States Patent and Trademark Office*